United States Patent
Brzustowicz et al.

(10) Patent No.: US 8,110,348 B2
(45) Date of Patent: Feb. 7, 2012

(54) METHODS AND COMPOSITIONS FOR THE DIAGNOSIS AND TREATMENT OF SCHIZOPHRENIA

(76) Inventors: Linda M. Brzustowicz, Madison, NJ (US); Bonnie L. Firestein-Miller, Hillsborough, NJ (US)

( * ) Notice: Subject to any disclaimer, the term of this patent is extended or adjusted under 35 U.S.C. 154(b) by 173 days.

(21) Appl. No.: 12/263,939

(22) Filed: Nov. 3, 2008

(65) Prior Publication Data
US 2009/0215877 A1  Aug. 27, 2009

Related U.S. Application Data

(63) Continuation-in-part of application No. 11/814,906, filed as application No. PCT/US2006/002771 on Jan. 26, 2006.

(60) Provisional application No. 60/647,261, filed on Jan. 26, 2005, provisional application No. 61/001,684, filed on Nov. 3, 2007.

(51) Int. Cl.
*C12Q 1/00* (2006.01)
*C12Q 1/68* (2006.01)
*C12N 5/00* (2006.01)
*C12N 5/0793* (2010.01)
*G01N 33/53* (2006.01)

(52) U.S. Cl. ............. 435/4; 435/325; 435/368; 435/7.1; 435/6.1

(58) Field of Classification Search ................. None
See application file for complete search history.

(56) References Cited

FOREIGN PATENT DOCUMENTS
| WO | WO 99/37768 | * | 7/1999 |
| WO | WO02098900 | * | 12/2002 |

OTHER PUBLICATIONS

Zaks-Makhina et al. Mol Pharm 65: 214-219, 2004.*

* cited by examiner

*Primary Examiner* — Daniel E Kolker
*Assistant Examiner* — Aditi Dutt
(74) *Attorney, Agent, or Firm* — Dann, Dorfman, Herrell & Skillman; Kathleen D. Rigaut

(57) ABSTRACT

Compositions and methods relating to the diagnosis and treatment of neuropsychiatric disorders, such as schizophrenia, schizoaffective disorders, and bipolar disorders are disclosed. Also provided are methods for screening therapeutic agents having efficacy for the treatment of such disorders.

5 Claims, 26 Drawing Sheets

Figure 6
A
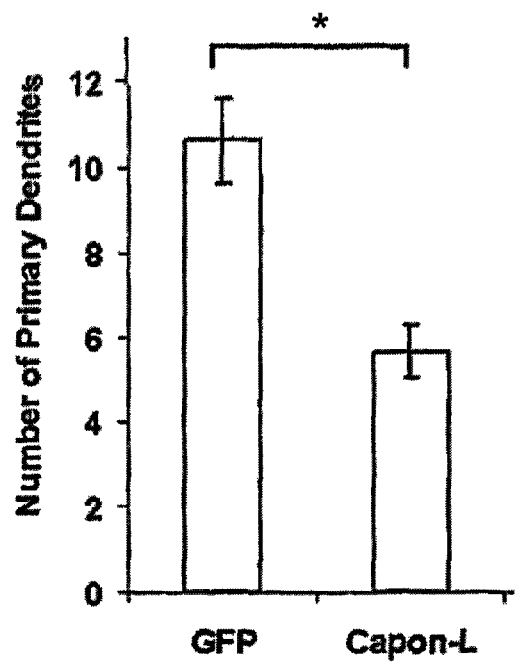
B
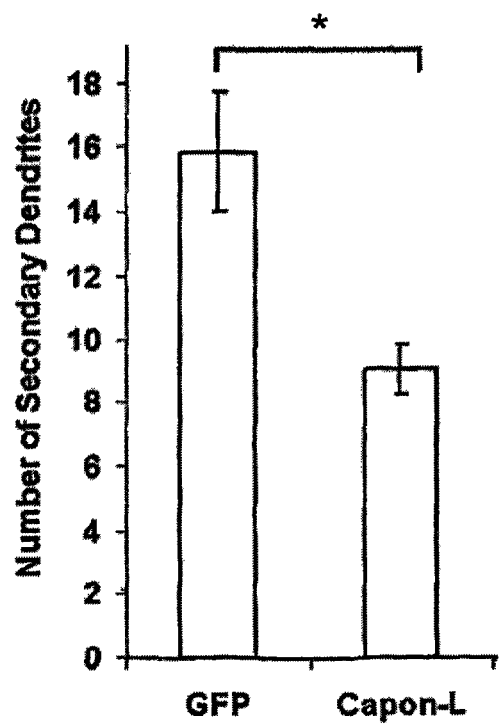

Figure 7

Promoter Sequence of
NOS1AP-L (SEQ ID NO: 25)

TGGCTTTGACACTGGCTTGACTGGTTACTTTCCGAGATTTTGGAGTTAGCCATGTATATAACAGCTGTC
CTGCAGCTCTACCTATGGTCTGTTTTCACAGATACTTGGTCACGAACTGGTCCTCCTATAGCTCCTT
TATTTGCATATCTTGCACCGTTCAGAAACTGAACACATAGGACACAACCCTTCCATTACCCGATATCTG
CCAAGATGGAGATAATTAGGCAACTTTCTCCAAAACTGTTGATGTAAAGGAGAAAAGTGACTAGGCCC
CTTCTTARCAATAGGCAAATTGAGCTCCAGCATTTACTAAGATGGAACCATAATACGCTGGCCGGAAA
TAACTCGGAAGCTCATTTTGTCCATACCCAGTGTAGACAGTCAAGAATATAAAAATGTTCTGGATTCT
CTTGTCCTTAGTACTCCTTTCTGCCTTCCCATTCTACAAGGCTGATGGCTTTTAAATGTTAAAACCC
TCCCTAAAGGCACCCCATAAGCCCTATTACACAAGTCACATACAGAACAAAAAGCGCTAAGATAGTCCT
CCATTTGGGCGCAGTCTTGCCTTCTGAGAAAGGGACTCTGAGAATTAATGAGGGCCAGATCTGGGAT
ATCTGGGACAAGAGACTGGGCTGGTAAACACGAAAACAATAAAACAATAAACACGGCCCCTCCCCC
TCTCCAAAACAAAAACAAAAACTTCAAGGCCCATCAGTAGCTCCGGCTCAGAATT
TGACCGTTAAAAAAGGAACTAGGCTGAGCTAGGGCCACCTCAGATCCCGGCAGTCTGGGCCGGGGCG
AAGTTGCCGGCTCGCGCGGCGCGGGCCAGGCCGGGGCCGGACTCTCCGGGACTTTCACCT
GCTCKGCTGGCAGCCGCGGCCAGCCGCGGGGCGGGACCCGGCCCGTTCGGGCCAAGCCCCACCGCT
GCGGTGCCGTTCCACTGCTCTGGGGCGCGCAGCCGCCGGCCAGTCCCGCTCCCGCCACTCCTCCTAGC
CCCCCCCGGCAGGCCGCCGCCCAGCCGCCGCCAGGGCTCGCGTGCCCGGAGGGTCCGCCAGGCCC
CGGCAGGAATTGCGGACCACAGCGCGCTCGCGCGCCATCAGTCCCTGCCGCCTCCAGCCCCGC
CTCGGCACCGCTCCGCGCCCAGCTCCAGTCTCCCCGGGTCTCGCCAGCCCCTTCCTGCCAGCCCCG
CACGCGTCGCCGCGCCCCAGCTCCAGTCTCCCCGGGTCTCGCCAGCCCCTTCCTGCCAGCCCCG
CCTCCGAAGGAGCGGGTCCGCCGCGGTAACCATGCCTAGCAAAACCA

Figure 8A

NOS1AP-L (SEQ ID NO: 1)

SEQ ID No. 1

>CAPON full-length
TTCTTCTTCGTCCCGGGCGGTGCGTTCCACTGCTCTGGGGCCGGCGCCGCGCCCAGTCC
CGCTTCGGGCCGCAAGCCCCACCGCTCCCCTCCCCGGGCAGGGGCGCCGCGCAGCCCGC
TCCCGCCGCCACCTCCTCCCCTGCCGCCCTCCTAGCCGGCAGGAATTGCGCGACCACAG
CGCCGCTCGCGTCGCCCGCATCAGCTCAGCCCGCTGCCGCTCGGCCCTCGGCACCGCTC
CGGGTCCGGCCGCCGCGGCCAGGGCTCCCCCTGCCCAGCGCTCCCAGGCCCCGCCAC
GCGTCGCCGCGCCCAGCTCCAGTCTCCCCTCCCCGGGGTCTCGCCAGCCCCTTCCTGCA
GCCGCCGCCTCCGAAGGAGCGGGTCCGCCGCGGGTAACCATGCCTAGCAAAACCAAGTA
CAACCTTGTGGACGATGGGCACGACCTGCGGATCCCCTTGCACAACGAGGACGCCTTCC
AGCACGGCATCTGCTTTGAGGCCAAGTACGTAGGAAGCCTGGACGTGCCAAGGCCCAAC
AGCAGGGTGGAGATCGTGGCTGCCATGCGCCGGATACGGTATGAGTTTAAAGCCAAGAA
CATCAAGAAGAAGAAAGTGAGCATTATGGTTTCAGTGGATGGAGTGAAAGTGATTCTGA
AGAAGAAGAAAAAGAAAAAGGAATGGACGTGGGATGAGAGCAAGATGCTGGTGATGCAG
GACCCCATCTACAGGATCTTCTATGTCTCTCATGATTCCCAAGACTTGAAGATCTTCAG
CTATATCGCTCGAGATGGTGCCAGCAATATCTTCAGGTGTAACGTCTTTAAATCCAAGA
AGAAGAGCCAAGCTATGAGAATCGTTCGGACGGTGGGCAGGCCTTTGAGGTCTGCCAC
AAGCTGAGCCTGCAGCACACGCAGCAGAATGCAGATGGCCAGGAAGATGGAGAGAGTGA
GAGGAACAGCAACAGCTCAGGAGACCCAGGCCGCCAGCTCACTGGAGCCGAGAGGGCCT
CCACGGCCACTGCAGAGGAGACTGACATCGATGCGGTGGAGGTCCCACTTCCAGGGAAT
GATGTCCTGGAATTCAGCCGAGGTGTGACTGATCTAGATGCTGTAGGGAAGGAAGGAGG
CTCTCACACAGGCTCCAAGGTTTCGCACCCCCAGGAGCCCATGCTGACAGCCTCACCCA
GGATGCTGCTCCCTTCTTCTTCCTCGAAGCCTCCAGGCCTGGGCACAGAGACACCGCTG
TCCACTCACCACCAGATGCAGCTCCTCCAGCAGCTCCTCCAGCAGCAGCAGCAGCAGAC
ACAAGTGGCTGTGGCCCAGGTACACTTGCTGAAGGACCAGTTGGCTGCTGAGGCTGCGG
CGCGGCTGGAGGCCCAGGCTCGCGTGCATCAGCTTTTGCTGCAGAACAAGGACATGCTC
CAGCACATCTCCCTGCTGGTCAAGCAGGTGCAAGAGCTGGAACTGAAGCTGTCAGGACA
GAACGCCATGGGCTCCCAGGACAGCTTGCTGGAGATCACCTTCCGCTCCGGAGCCCTGC
CCGTGCTCTGTGACCCCACGACCCCTAAGCCAGAGGACCTGCATTCGCCGCCGCTGGGC
GCGGGCTTGGCTGACTTTGCCCACCCTGCGGGCAGCCCCTTAGGTAGGCGCGACTGCTT
GGTGAAGCTGGAGTGCTTTCGCTTTCTTCCGCCCGAGGACACCCCGCCCCAGCGCAGG
GCGAGGCGCTCCTGGGCGGTCTGGAGCTCATCAAGTTCCGAGAGTCAGGCATCGCCTCG
GAGTACGAGTCCAACACGGACGAGAGCGAGGAGCGCGACTCGTGGTCCCAGGAGGAGCT
GCCGCGCCTGCTGAATGTCCTGCAGAGGCAGGAACTGGGCGACGGCCTGGATGATGAGA
TCGCCGTGTAGGTGCCGAGGGCGAGGAGATGGAGGCGGCGGCGTGGCTGGAGGGGCCGT
GTCTGGCTGCTGCCCGGGTAGGGGATGCCCAGTGAATGTGCACTGCCGAGGAGAATGCC
AGCCAGGGCCCGGGAGAGTGTGAGGTTTCAGGAAAGTATTGAGATTCTGCTTTGGAGGG
TAAAGTGGGGAAGAAATCGGATTCCCAGAGGTGAATCAGCTCCTCTCCTACTTGTGACT
AGAGGGTGGTGGAGGTAAGGCCTTCCAGAGCCCATGGCTTCAGGAGAGGGTCTCTCTCC
AGGACTGCCAGGCTGCTGGAGGACCTGCCCCTACCTGCTGCATCGTCAGGCTCCCACGC
TTTGTCCGTGATGCCCCCCTACCCCCTCACTCTCCCGTCTCCATGGTCCCGACCAGGA
AGGGAAGCCATCGGTACCTTCTCAGGTACTTTGTTTCTGGATATCACGATGCTGCGAGT

Figure 8A (Cont.)

```
TGCCTAACCCTCCCCCTACCTTTATGAGAGGAATTCCTTCTCCAGGCCCTTGCTGAGAT
TGTAGAGATTGAGTGCTCTGGACCGCAAAAGCCAGGCTAGTCCTTGTAGGGTGAGCATG
GAATTGGAATGTGTCACAGTGGATAAGCTTTTAGAGGAACTGAATCCAAACATTTTCTC
CAGCCGGACATTGAATGTTGCTACAAAGGGAGCCTTGAAGCTTTAACATGGTTCAGGCC
CTTGGTGTGAGAGCCCAGGGGGAGGACAGCTTGTCTGCTGCTCCAAATCACTTAGATCT
GATTCCTGTTTTGAAAGTCCTGCCCTGCCTTCCTCCTGCTGTAGCCCAGCCCATCTAA
ATGGAAGCTGGGAATTGCCCCTCACCTCCCCTGTGTCCTGTCCAGCTGAAGCTTTTGCA
GCACTTTACCTCTCTGAAAGCCCCAGAGGACCAGAGCCCCCAGCCTTACCTCTCAACCT
GTCCCCTCCACTGGGCAGTGGTGGTCAGTTTTTACTGC
```

Figure 8B

NOS1AP-L Protein (SEQ ID NO: 2)

```
Met Pro Ser Lys Thr Lys Tyr Asn Leu Val Asp Asp Gly His Asp Leu
 1           5                  10                  15
Arg Ile Pro Leu His Asn Glu Asp Ala Phe Gln His Gly Ile Cys Phe
            20                  25                  30
Glu Ala Lys Tyr Val Gly Ser Leu Asp Val Pro Arg Pro Asn Ser Arg
            35                  40                  45
Val Glu Ile Val Ala Ala Met Arg Arg Ile Arg Tyr Glu Phe Lys Ala
 50                  55                  60
Lys Asn Ile Lys Lys Lys Val Ser Ile Met Val Ser Val Asp Gly
 65                  70                  75                  80
Val Lys Val Ile Leu Lys Lys Lys Lys Lys Lys Glu Trp Thr Trp
                     85                  90                  95
Asp Glu Ser Lys Met Leu Val Met Gln Asp Pro Ile Tyr Arg Ile Phe
            100                 105                 110
Tyr Val Ser His Asp Ser Gln Asp Leu Lys Ile Phe Ser Tyr Ile Ala
            115                 120                 125
Arg Asp Gly Ala Ser Asn Ile Phe Arg Cys Asn Val Phe Lys Ser Lys
 130                 135                 140
Lys Lys Ser Gln Ala Met Arg Ile Val Arg Thr Val Gly Gln Ala Phe
 145                 150                 155                 160
Glu Val Cys His Lys Leu Ser Leu Gln His Thr Gln Gln Asn Ala Asp
            165                 170                 175
Gly Gln Glu Asp Gly Glu Ser Glu Arg Asn Ser Asn Ser Ser Gly Asp
            180                 185                 190
Pro Gly Arg Gln Leu Thr Gly Ala Glu Arg Ala Ser Thr Ala Thr Ala
            195                 200                 205
Glu Glu Thr Asp Ile Asp Ala Val Glu Val Pro Leu Pro Gly Asn Asp
 210                 215                 220
Val Leu Glu Phe Ser Arg Gly Val Thr Asp Leu Asp Ala Val Gly Lys
 225                 230                 235                 240
Glu Gly Gly Ser His Thr Gly Ser Lys Val Ser His Pro Gln Glu Pro
            245                 250                 255
Met Leu Thr Ala Ser Pro Arg Met Leu Leu Pro Ser Ser Ser Ser Lys
            260                 265                 270
Pro Pro Gly Leu Gly Thr Glu Thr Pro Leu Ser Thr His His Gln Met
            275                 280                 285
Gln Leu Leu Gln Gln Leu Leu Gln Gln Gln Gln Gln Thr Gln Val
 290                 295                 300
Ala Val Ala Gln Val His Leu Leu Lys Asp Gln Leu Ala Ala Glu Ala
 305                 310                 315                 320
Ala Ala Arg Leu Glu Ala Gln Ala Arg Val His Gln Leu Leu Leu Gln
            325                 330                 335
Asn Lys Asp Met Leu Gln His Ile Ser Leu Leu Val Lys Gln Val Gln
            340                 345                 350
Glu Leu Glu Leu Lys Leu Ser Gly Gln Asn Ala Met Gly Ser Gln Asp
            355                 360                 365
Ser Leu Leu Glu Ile Thr Phe Arg Ser Gly Ala Leu Pro Val Leu Cys
 370                 375                 380
Asp Pro Thr Thr Pro Lys Pro Glu Asp Leu His Ser Pro Pro Leu Gly
 385                 390                 395                 400
Ala Gly Leu Ala Asp Phe Ala His Pro Ala Gly Ser Pro Leu Gly Arg
            405                 410                 415
Arg Asp Cys Leu Val Lys Leu Glu Cys Phe Arg Phe Leu Pro Pro Glu
            420                 425                 430
Asp Thr Pro Pro Pro Ala Gln Gly Glu Ala Leu Leu Gly Gly Leu Glu
            435                 440                 445
Leu Ile Lys Phe Arg Glu Ser Gly Ile Ala Ser Glu Tyr Glu Ser Asn
            450                 455                 460
Thr Asp Glu Ser Glu Glu Arg Asp Ser Trp Ser Gln Glu Glu Leu Pro
 465                 470                 475                 480
Arg Leu Leu Asn Val Leu Gln Arg Gln Glu Leu Gly Asp Gly Leu Asp
                     485                 490                 495
Asp Glu Ile Ala Val
            500
```

Figure 8C

NOS1AP-S (SEQ ID NO: 3)

```
SEQ ID No. 3 (AY841899)
ctatgaccaa atgtatgggg cttttccca cacaccaagc aagcaagcag ttctgcagag61
ggcacacagt gtcctctaac tcagtttgat tctgatacta tctacctgga aacagcatca121
gatcccacag tttgagggct caatcccaca agactttccc ccatttcaga caccaatcac181
aagtaatagt ttgtcaccta cacctctgac caagtggcta taaattggtg ttcccactac241
cctctccttg gactcaactg atttgctaga gcaactgaca gaactcagga aaacaactac301
atttactggt ttattttaaa ggatattata aggatacca atgaacacca gatggaagag361
atgcataggg cagggtctgt gggaaggatg gcagagctcc catgccctcc caacgtgcac421
caccctccag gaacctctaa atgttcagct gcccggcagc tccccacacc cagtccttt481
gagttttaa tggaggcttt attatgtagg catgattgat tacatcattg gccactggtg541
attagtttaa cttttagcac ctcatctcct ggaggttggg gcgtgtggact gaaaaatcct601
atcctctaat cataccttgg totgtcctgt gagcagccc catcccgaag cttccagggg661
ttccccaacc actaatcatc taataagcat acaaaagaca ctcttaccac tctggagatc721
tcaagggttt ggggagctat atgtcaggaa acagggatga agaccaaaca tgtatttcac781
tgtatcacac ctgttctcac cctccccag atcttctctc aattaatatg agacaaaaaa841
atgagtctga ctccttgacc aaaatatcag ttctgtcctt agcagcttta tggaggacag901
atttagttta aattccttag gcattatgcc cctgtggctc cactccatca gaaatagggt961
caacggcaag gtcagggcct ccaatctggg caagagggag gcagccacgg tatccacaag1021
tgtaattctc tgagtgctgg ttgctgggag gggcacaccc tgggccagca agtcacttgg1081
ccaaggggtgg ccaactgtga ggtagcactg ccctttactc cctaaaaaaa tgtgaatctc1141
tttggagcaa actcctcttc agaaatttga gcactgttt totgagcaag ggaatcagct1201
aatgcttttg actcccatc catcttcctg catcctagtc cccacctctcc tgcccccact1261
caactggctc tgtctttacc cacaccatgg tttggtaca agaacaccct tttcccata1321
agctacattg gtccaggcaa taaaaattca ttagttcct ttcttcaggg gccttctgaa1381
atgctccctg gagaactctt tattccctc tttgcacaag aatcacatat gtgtgaacac1441
tggtattggc cttctaactc agttctca aacagggtc ctggtctggt tgcccctgtc1501
tcctcccact gagtttatc tccacataag tattgctcac caagaacaga gctgttgaca1561
ccactgggcc tcaagcatgc tgaatgcatt gctgccaact gctctgcctt aagaaggttg1621
gaaactgatg agggtgccac aaattgttca cctcagccct tctgggctgg ttggaggagg1681
```

Figure 8C (Cont.)

```
ccctctcatg aatcagtcag caaatgtttg accoctacca ggtggtcctg gtaatatgtg1741
gtatgaatca tggtcctaga tgtctgccat agcaaataaa aaaggaagac agggaaagaa1801
gctgtcgcct acagagtggc ttgatgacag ctgcctcact aatttaaaaa gccatgtgta1861
gtgcttccta tttctcacta tgtttgggtg agtgggagag ggagaaagat tatatgggct1921
tcgttgtgac actgttctta gccagtgggt caatagatga gttttggttt tgtttttag1981
aagacaggat gagaagagag tgccccctto cacctccatc atggcatgcc atgtagqtg2041
ctgaaggagt tctctaagca gggatggagc accgtgcgtg tgtgtgtgta tatgtgcacg2101
tgtgtgtgta cgtgtgtgtg tgtggcaggt ctagagggtc gatggctctt tcctgcctct2161
tgcccttggt atgggtacct tagtgatgca tcatggcact cccttaggac acacagcttc2221
gcagtgccag tgaacccaac ccttttggct cctcctctgg aatgataagc ccagatgccc2281
atgctgcccg tgaaggcgtt cttcttgaac tgaatgtgga gggcatctct ggtccaqgcc2341
atctgccagt gactctcatg tgcattcatg tccctctctt ctctctgtcc tgtcttctct2401
gccgctgcct cttctctgca ggtacacttg ctgaaggacc agttggctgc tgaggctgcg2461
gcgcggctgg aggccaaggc tcgcgtgcat cagcttttgc tgcagaacaa ggacatgctc2521
cagcacatct ccctgctggt caagcaggtg caagagctgg aactgaagct gtcaggacag2581
aacgccatgg gctcccagga cagcttgctg gagatcaacc tccgctccgg agccctgccc2641
gtgctctgtg acccacgac ccctaagcca gaggacatgc attggccgcc gctgggcgcg2701
ggcttggctg actttgccca cctgcgggc agcccttag gtaggcgcga ctgcttggtg2761
aagctggagt gctttgctt tcttccgccc gaggacacc cgcccccage gcagggcgag2821
gcgctcctgg ggggtctgga gctcatcaag ttccgagagt caggcatcgc ctcggagtac2881
gagtccaaca cggacgagag cgaggagcgc gactgtggt ccaggagga gctgccgcgc2941
ctgctgaatg tcctgcagag gcaggaactg ggcgacggcc tggatgatga gatgccgtg3001
taggtgccga gggcgaggag atggaggcgg cggcgtgget ggagggcgtg tgtctggctg3061
ctgcccggqt aggggatgcc cagtgaatgt gcactgccga ggagaatgcc agccagggcc3121
cqggagagtg tgaggtttca ggaaagtatt gagattctgc tttggagggt aaagtgggga3181
agaaatcgga ttccagagg tgaatcagct cctctcctac ttgtgactag agggtggtgg3241
aggtaaggcc ttccagagcc catggcttca ggagagggtc tctctccagg actgccagge3301
tgctggagga cctgcccctca cctgctgcat cgtcaggcto ccacgctttg tcgtgatgc3361
cccctaccc cctcactctc ccgtctcca tgtcccgac caggaaggga agccatccgt3421
accttctcag gtactttgtt tctggatatc acgatgctgc gagttgccta acccctcccc3481
taccttctatg agaggaattc cttctccagg cccttgctga gattgtagag attgagtgct3541
ctggaccgca aaagccagge tagtccttgt agggtgagca tggaattgga atgtgtcaca3601
gtggataagc ttttagagga actgaatcca aacattttct ccagccggac attgaatgtt3661
gctacaaagg gagccttgaa gctttaacat ggttcaggcc cttggtgtga gagccaggg3721
ggaggacage ttgtctgctg ctccaaatca cttagatctg attcctgttt tgaaagtcct3781
gccctgcctt cctcctgcct gtagcccage ccatctaaat ggaagctgg aattgcccct3841
cacctcccct gtgtcctgtc cagctgaagc tttgcagca cttacctct ctgaaagccc3901
cagaggacca gagccccag cctacctct caacctgtcc cctccactgg gcagtggtgg3961
tcagttttta ctgcaaaaaa aaaaaagaa aaagagaaa gaaaaaag aatgaatgca4021
agctgatagc tgagactgtg agactgtttt tgtccactct tctgaatcac tgccacttgg4081
gtcagggacc acagccattg ccacccttgg cccatctctc tggtgcgtg ccttgagcac4141
acatataaaa agtgccatgt gcaattgtct tatcttttat gatctaggct ttgctaggg4201
atcactactc cttaacggc tggctgggc gatgaggaaa agctcctttg ctctgtaag4261
gccataagtg gctgttaaca gattttcaaa tgcctgaaga gattgctgag acctgctaga4321
gtcatatgtt cggggaatta agtctttatc ctagacaaca aggtacagat gcaaactgca4381
gtgttattgg aggqtcaatc ggcaaggata tgattatccc aaaatggagt tcatcgaccc4441
tagcttcct ttagattata tataaataaa agtgcagtcc tcttctaatg gccacagttg4501
gttttcttgt agccagaaa gtccaaatta aaqgaaataa attcagtttt atgttagcct4561
tccttggtgc atcagggtgt cagtggaat aggatcaggt ggtgtgtgtg tgtgtgtttt4621
gtgtgtgtgt gtacacatgt gtttatatat acatgtgtga gggaaagtgt gtacatatat4681
gtaggattgt aaccagacgg aaaagaatga ggatctccag ggtgtttgaa tcagcaacag4741
atttgtgttt tctaacatgc atttagttgg agaggcatgg ttctgtttgt tttgtttga4801
tctaatttgc cattggaaat aggtacagtt acacagagaa ggaagaacca ggaaagtgag4861
atccatgaaa ctaaatgagc agctgtcaga atccagtgtg gctgagccta cctagcttat4921
gaaatctaac ccagggttcc ctgagtccaa gaccacttag attattaaga ttttgaaagt4981
ccagaggagt gaaagtctg ttttctgacg taagccggag ctgaggataa agccagaggc5041
```

Figure 8C (Cont.)

```
cagtggatta ggtgtatgga atgtggatgg agagggcttg tgtgggatgt ggccagggag5101
tgggtgagga aggccgcttc taaatggcct gtaaaaactt gagattggat agacgaaagg5161
aaatggagaa attaaagaat tggagaaact agttatctgt gttgctgact ttgggaccca5221
tccaagactc ctgcctttgg ggtgttccat ggtggtttct tcctgcctgg gcgccaccct5281
ttccccagtt caggccctcc ctggaggact agtttgtgta ttggcatcct cccagtgga5341
cccaaaccag cgcatacttg gtgtgtggag atgggagaca aaggacagat ctaggagcct5401
tgaaggatca ccagccaccg accctccatc agggccaact gggcaggaaa gggaacattg5461
cagacctgat ttcccgacga tgtcaccctg tcctccctcc ttgcttcttg ctctgctaac5521
tcaactctgc cttcctcttt ttcattcttc tactctgcc
```

Figure 8D

NOS1AP-S PROTEIN (SEQ ID NO: 4)

SEQ ID No. 4 (AAW57298)
mslsslcpvf saaasslqvh llkdqlaaea aarleagarv hqlllqnkdm lqhisllvkq 61
vqelelkisg qnamgsqdsl leitfrsgal pvlcdpttpk pedlhspplg agladfahpa 121
gsplgrrdcl vklecfrflp pedtpppagg eallggleli kfresgiase yesntdesee 181
rdswsqeelp rllnvlgrqe lgdglddeia v Figure 17
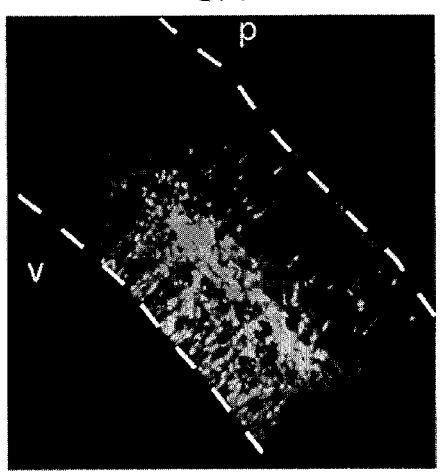
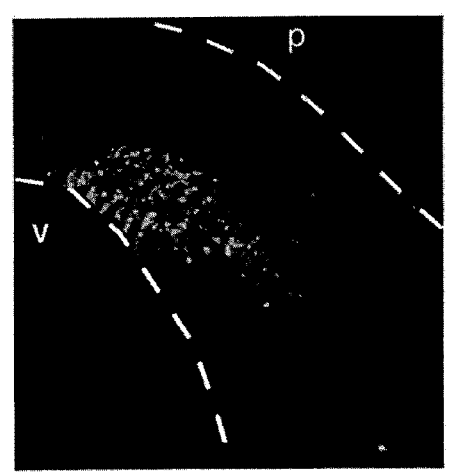
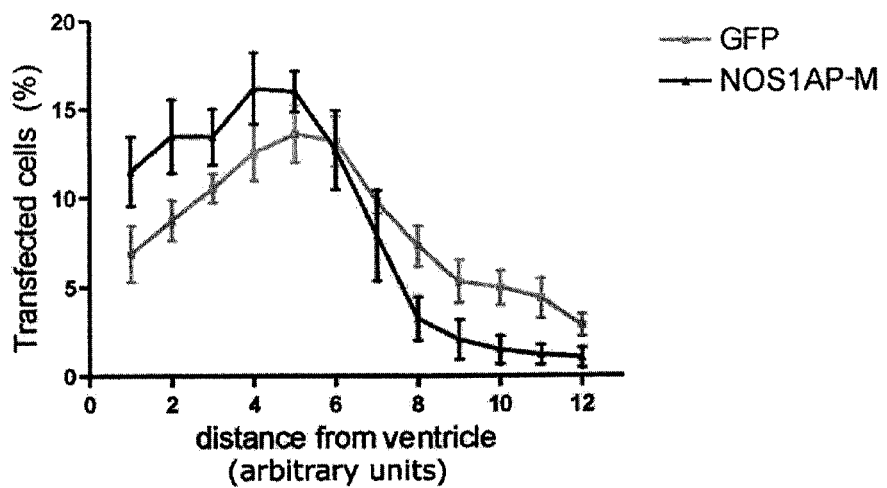

METHODS AND COMPOSITIONS FOR THE DIAGNOSIS AND TREATMENT OF SCHIZOPHRENIA

PRIORITY CLAIMS

This application is a continuation-in-part Application of U.S. patent application Ser. No. 11/814,906, filed Sep. 9, 2008, which was filed under 35 U.S.C. §371 and claims priority to PCT/US06/02771, filed Jan. 26, 2006, which in turn claims priority to U.S. Provisional Application 60/647,261, filed Jan. 26, 2005. This application also claims priority under 35 U.S.C. §119(e) to U.S. Provisional Patent Application 61/001,684, filed Nov. 3, 2007. Each of the foregoing applications is incorporated by reference herein.

GOVERNMENT RIGHTS

Pursuant to 35 U.S.C. §202(c) it is acknowledged that the U.S. Government has certain rights in the invention described herein, which was made in part with funds from the National Institutes of Health, Grant Numbers: R01 MH62440 and K25 AA015346.

FIELD OF THE INVENTION

The present invention relates generally to the diagnosis and treatment of neuropsychiatric disorders, such as schizophrenia, schizoaffective disorders and bipolar disorders.

BACKGROUND OF THE INVENTION

Several publications and patent documents are cited throughout the specification in order to describe the state of the art to which this invention pertains. Each of these citations is incorporated herein by reference as though set forth in full.

Schizophrenia is a serious neuropsychiatric illness estimated to affect 1.3% of the adult population in the United States (Report of the Surgeon General on Mental Health, 1999). The Diagnostic and Statistical Manual-IIIR and IV (DSM-IIIR and DSM-IV) criteria used to diagnose schizophrenia are well known to the skilled artisan. Age of onset is typically between age 15 and 25 for men, and between age 25 and 35 for women. The symptoms typically develop over weeks to months, with a prodromal period preceding the onset of acute psychotic symptoms. The disease is chronic, characterized by episodes of worsening symptoms with active psychosis, followed by periods of relative recovery marked by significant residual impairment. Current treatment is purely symptomatic, with no cure.

The lifetime risk for schizophrenia is 1.5 percent. Risk factors for schizophrenia include a history of schizophrenia in first-degree relatives, birth during the late winter months, and birth trauma. Patients with schizophrenia have substantial amounts of physical and psychological disability, as well as occupational difficulties, with disability equivalent to quadriplegia during periods of worsened symptoms (Report of the Surgeon General on Mental Health, 1999).

Schizoaffective disorder is a related syndrome characterized by the same disability and psychotic symptoms, but with the added feature of prevalent symptoms of mood disturbance. DSM-IIIR and DSM-IV diagnostic criteria are also available to assist in diagnosing this disorder. The lifetime prevalence of schizoaffective disorder is 0.5 to 0.8 percent.

A genetic component for schizophrenia has long been suggested. Family, twin and adoption studies have demonstrated that schizophrenia is predominantly genetic, with a high heritability (McGuffin et al., Br. J. Psychiatry 164:593, 1994). Segregation analyses have failed to clearly support a single model of inheritance, with the suggestion of at least several, possibly interacting, susceptibility loci (Risch, Hum. Genet. 46:222, 1990). Schizophrenia and schizoaffective disorder are often observed within the same family, suggesting that the two disorders may share a common genetic etiology.

Bipolar disorder, another type of neuropsychiatric disorder, is also known as manic-depressive illness and is also described and characterized in DSM-IIIR and DSM-IV. It involves cycles of mania and depression. Signs and symptoms of mania include: extreme irritability and distractibility; excessive euphoric feelings; a sustained period of behavior that is different from the usual behavior; increased energy activity, restlessness, racing thoughts and rapid talking; decreased need for sleep; unrealistic beliefs in one's abilities and powers; uncharacteristically poor judgment; increased sexual drive; abuse of drugs, particularly cocaine, alcohol and sleeping medications; obnoxious, provocative or intrusive behavior and denial that anything is wrong. Signs and symptoms of depression include: persistent sad, anxious or empty mood; feeling of hopelessness or pessimism; feeling of guilt, worthlessness or helplessness; loss of interest or pleasure in ordinary activities; decreased energy, a feeling of fatigue or of being "slowed down"; difficulty concentrating, remembering and making decisions; restlessness and irritability; sleep disturbances; loss of appetite and weight, or weight gain; chronic pain or other persistent bodily symptoms that are not caused by physical disease; and thoughts of death or suicide. Most people with manic-depressive illness can be helped with treatment. However, manic-depressive illness, which is currently diagnosed by symptoms alone, is often not recognized by the patient, relatives, friends and even physicians. If left untreated, bipolar disorder tends to worsen, and the person experiences episodes of full-fledged mania and clinical depression.

Neuropsychiatric disorders, such as schizophrenia, attention deficit disorders, schizoaffective disorders, bipolar disorders and unipolar disorders, differ from neurological disorders in that anatomical or biochemical pathologies are readily detectable for the latter but not the former. Largely as a result of this difference, drugs which have been used to treat individuals with neuropsychiatric disorders, including lithium salts, valproic acid and carbamazepine, have not been predictably effective in treatment regimens across a variety of patients. Treatment regimens are further complicated by the fact that clinical diagnosis currently relies on clinical observation and subjective reports. Identification of the anatomical or biochemical defects which result in neuropsychiatric disorders is needed in order to effectively identify these disorders and to allow the design and administration of effective therapeutics for these disorders. Indeed, there is growing evidence that the episodes of severe psychotic symptoms may lead to irreversible decrements in long-term functioning. Current clinical trials have begun to treat individuals in the prodromal phase, with hopes of limiting the ultimate disability caused by these illnesses. Unfortunately, the diagnosis of neuropsychiatric disorders, such as schizophrenia, attention deficit disorders, schizoaffective disorders, bipolar disorders and unipolar disorders, cannot be accurately made during the prodromal phase. Additionally, the treatments carry a significant risk of serious side effects thus currently limiting this early intervention strategy to individuals known to be at extremely high risk for developing one of these disorders.

Identification of genes associated neuropsychiatric disorders would greatly facilitate the diagnosis and treatment of these illnesses. It is an object of the present invention to provide materials, methods and kits which will aid the clinician in diagnosing and treating such mental disorders. Other objects of the invention are compositions, methods, and kits which will facilitate the identification of pharmaceuticals useful in treating neuropsychiatric disorders.

SUMMARY OF THE INVENTION

In accordance with the present invention, methods for assessing test compounds for schizophrenia-related protein modulating activities are provided. The schizophrenia-related proteins of the present invention include NOS1AP-L of SEQ ID NO: 2 and a short form of the same protein, hereinafter referred to as NOS1AP-S, having the sequence of SEQ ID NO: 4. Exemplary methods comprise: a) providing a host cell expressing a nucleic acid encoding NOS1AP-L or NOS1AP-S protein; b) contacting the host cell with a compound suspected of modulating the NOS1AP protein activity; and c) determining the extent of the modulation, if any. Also in one embodiment of the present invention, the host cells may be neurons, and more particularly, hippocampal neurons. NOS1AP protein activity can include, without limitation, disruption of dendrite outgrowth and branching, and changes in nitric oxide production upon stimulation of the NMDA receptor. Agents can also be screened in such host cells for their capacity to modulate NOS1AP mRNA and/or protein production levels.

In accordance with the present invention, it has been determined that patients suffering from neuropsychiatric disorders overexpress NOS1AP when compared to normal controls. Thus, another screening method of the invention entails operably linking the promoter region of NOS1AP to a nucleic acid encoding a reporter gene and identifying agents which affect the expression level of the reporter. In a particularly preferred embodiment, the promoter is shown in FIG. 7. The promoter will be also be modified to include certain SNPs previously identified to be associated with the onset of schizophrenia. The modified promoters will also be assessed in such reporter assays.

In yet another aspect of the present invention, methods for assessing test compounds having binding affinity for NOS1AP-L and/or NOS1AP-S protein are provided. An exemplary assay comprises providing the NOS1AP-L or NOS1AP-S protein in purified form; b) contacting the purified NOS1AP protein with a compound suspected of binding the NOS1AP protein; and c) determining the extent of complex formation between said test compound and NOS1AP protein, if any.

In yet another aspect of the present invention, methods for diagnosing susceptibility to a neuropsychiatric disorder, e.g., schizophrenia, schizoaffective disorder and/or bipolar disease in a patient are provided. Such methods comprise determining the expression level of NOS1AP-L (SEQ ID NO: 1) and/or NOS1AP-S (SEQ ID No. 3) or the proteins encoded thereby in a patient, wherein an elevated expression level of NOS1AP in the patient compared to that in normal healthy subjects is indicative of susceptibility to schizophrenia.

Methods for treating neuropsychiatric disorders by administering to a patient an effective amount of an antagonist specific for NOS1AP protein (SEQ ID NO: 2 or SEQ ID No. 4) are disclosed. Such antagonists can include, without limitation, an anti-sense oligonucleotide specific for the NOS1AP-L or the NOS1AP-S gene and/or a SiRNA molecule effective for down-regulating production of NOS1AP. Representative neuropsychiatric disorders which can be treated using the methods disclosed herein include, without limitation, schizophrenia, schizoaffective disorder, and bipolar disorder. Exemplary antagonists which disrupt NOS1AP protein activity can include antibodies immunologically specific for the NOS1AP-S protein described herein. Such agents can also include pharmacological compounds identified using the screening assays disclosed herein.

In yet another aspect of the invention, methods for identifying a compound which inhibits NOS1AP-NOS1AP binding protein complex formation are provided. Such methods comprise incubating said NOS1AP or functional fragment thereof and said binding protein in the presence and absence of said compound under conditions suitable for protein complex formation to occur, and determining whether the complex formation is decreased in the presence of said compound when compared to complex formation in the absence of said compound, wherein a decrease in NOS1AP-NOS1AP binding protein complex formation in the presence of said compound indicates that the compound is an inhibitor of NOS1AP-NOS1AP binding protein complex formation.

Another aspect of the invention optionally provides a siRNA specific to NOS1AP-L comprising SEQ ID NO: 22, as well as methods for increasing dendrite branching, comprising delivering an inhibitory construct comprising SEQ ID NO: 22 to a cell.

In yet another embodiment, methods of treating a neuropsychiatric disorder in a patient are provided comprising administering an effective amount of a compound capable of inhibiting the activity of carboxypeptidase E in a patient.

BRIEF DESCRIPTION OF THE DRAWINGS

FIG. 1A shows the genomic organization of NOS1AP. Exons are represented by numbered boxes; 5' and 3' UTR are represented by half-height boxes. FIG. 1B shows the NOS1AP transcripts. 5' and 3' UTR are represented by shaded boxes, exons by white boxes. FIG. 1C shows the predicted NOS1AP proteins. The PTB domain is shaded light grey, and the PDZ-binding domain is shaded black.

FIGS. 6A and 6B are graphs showing that the overexpression of NOS1AP full-length (SEQ ID NO: 1, indicated by "NOS1AP-L") results in decreased number of primary and secondary dendrites in hippocampal neurons. *p<0.05 and **p<0.01 by nonparametric ANOVA (Kruskal-Wallis) followed by Dunn's Multiple Comparison Test.

FIG. 7 shows the promoter sequence of NOS1AP-L. (SEQ ID NO: 25)

FIGS. 8A-D shows the nucleic acid and amino acid sequences of NOS1AP-L, SEQ ID NOS: 1 and 2 (FIGS. 8A and 8B respectively). The Figures also shows the nucleic acid and amino acid sequences of NOS1AP-S, SEQ ID NOS: 3 and 4 (FIGS. 8C and 8D respectively).

FIG. 17 shows overexpression of NOS1AP-M results in neuronal migration defect in vivo. A, plasmids encoding GFP-NOS1AP-M or GFP were electroporated into cells lining the lateral ventricular wall at E16 and analyzed at E18. In control, some positive cells are migrating to the cortical plate. However, NOS1AP-M overexpression resulted in very few neurons positioned in the cortical plate. V=ventricle, P=pial surface. B, bin distribution of migration distance from v to p. The cortical mantle was divided into twelve equally spaced bins, and percentage of cells in each bin was represented. In control, approximately 17% of cells were positioned in the upper four bins, whereas NOS1AP-M overexpression resulted in few than 6% in upper bins. n=4 for GFP and n=5 for NOS1AP M, more than 900 cells per condition. Graph plot mean±SEM. p=0.0276 for NOS1AP-M vs. GFP data shown in B by Kolmogorov-Smirnov (chi-squared+8.563).

DETAILED DESCRIPTION OF THE INVENTION

Figure 1:
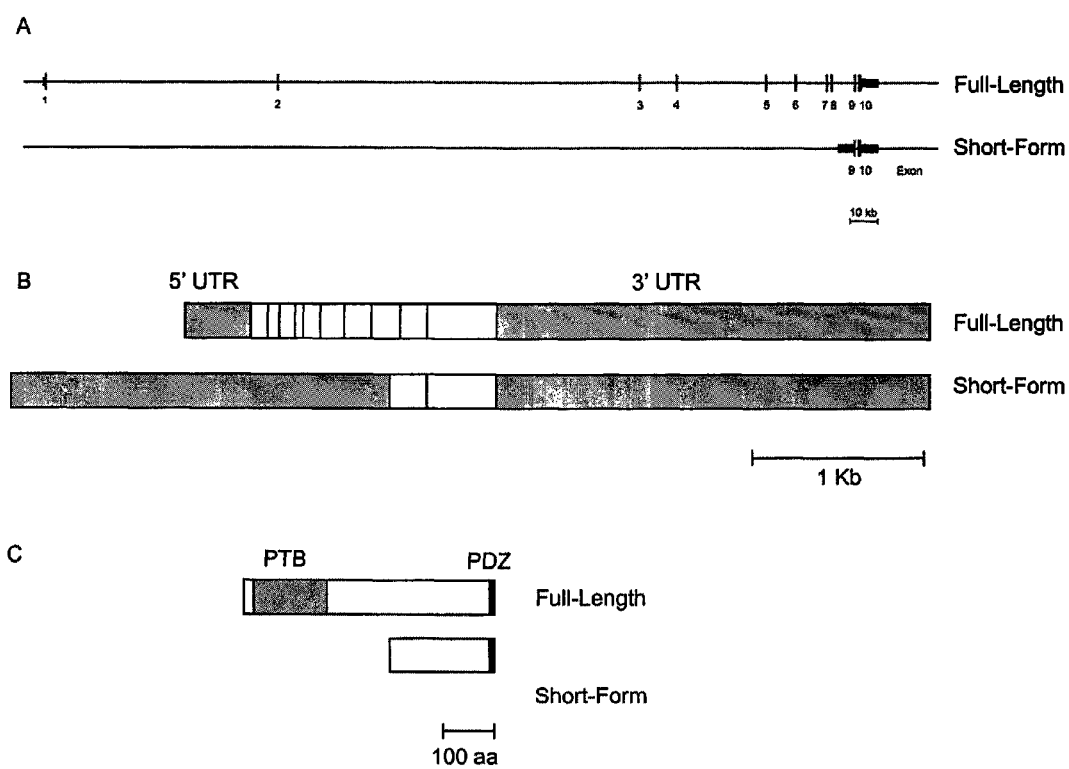
FIGS. 1A-1C are diagrams illustrating the gene structure, isoforms and protein functional domains of NOS1AP. The terms CAPON and NOS1AP are used interchangeably herein as they refer the same protein.

Several prior independent studies have reported the linkage of markers from chromosome 1q22 to schizophrenia. Within this linkage region, the present inventors identified significant linkage disequilibrium (LD) between schizophrenia and markers within the gene for carboxyl-terminal PDZ ligand of neuronal nitric oxide synthase (NOS1AP, GenBank Accession No. NM_014697, also known in the art as CAPON). Prior sequencing of the 10 exons of NOS1AP, however, failed to reveal a coding mutation associated with illness. The present invention is related to the discovery of two NOS1AP isoforms, "NOS1AP full-length" (SEQ ID No. 1) which encodes a full-length NOS1AP Protein (SEQ ID No. 2) and "NOS1AP short-form (NOS1AP-S)" (SEQ ID No. 3) which encodes a short-form NOS1AP protein (NOS1AP-S) (SEQ ID No. 4). Compared to the previously disclosed NOS1AP gene (GenBank Accession No. NM_014697), NOS1AP full-length (SEQ ID NO. 1) of the present invention contains an additional 60 bp of 5' untranslated region (UTR) and lacks the first 15 bp of sequence present in the fourth exon of the previously disclosed NOS1AP (GenBank Accession No. NM_014697), while NOS1AP-S (SEQ ID No. 3) of the present invention contains the last two exons of the previously disclosed NOS1AP (GenBank Accession No. NM_014697) and parts of the intron preceding the penultimate exon, and additional 3' UTR sequences. The present inventors have discovered that the expression of NOS1AP-S (SEQ ID No. 3) is significantly increased (p<0.05) in both schizophrenia and bipolar disorder. Furthermore, this increased expression is significantly associated (p<0.005) with genotype at the three single-nucleotide polymorphisms (SNPs) previously identified as being in linkage disequilibrium with schizophrenia. Expression of NOS1AP full-length (SEQ ID No. 1) appears to be sensitive to treatment with antipsychotic medication, but is significantly (p<0.005) elevated in individuals with bipolar disorder and no history of antipsychotic exposure. These results provide support for the role of NOS1AP-L and NOS1AP-S in the etiology of schizophrenia, and provide new evidence implicating this gene in the etiology of bipolar disorder as well. In addition, the outgrowth and branching of dendrites is inhibited when hippocampal neurons are transfected with cDNA encoding either NOS1AP full-length (SEQ ID No. 1) or NOS1AP-S (SEQ ID No. 3). This provides an exemplary model system for screening agents which impact NOS1AP activity, thereby identifying pharmaceuticals useful in the prevention and treatment of neuropsychiatric disorders.

I. DEFINITIONS

The following definitions are provided to facilitate an understanding of the present invention:

"Linkage" describes the tendency of genes, alleles, loci or genetic markers to be inherited together as a result of their location on the same chromosome, and is measured by percent recombination (also called recombination fraction, or $\theta$) between the two genes, alleles, loci or genetic markers. The closer two loci physically are on the chromosome, the lower the recombination fraction will be. Normally, when a polymorphic site from within a disease-causing gene is tested for linkage with the disease, the recombination fraction will be zero, indicating that the disease and the disease-causing gene are always co-inherited. In rare cases, when a gene spans a very large segment of the genome, it may be possible to observe recombination between polymorphic sites on one end of the gene and causative mutations on the other. However, if the causative mutation is the polymorphism being tested for linkage with the disease, no recombination will be observed.

"Centimorgan" is a unit of genetic distance signifying linkage between two genetic markers, alleles, genes or loci, corresponding to a probability of recombination between the two markers or loci of 1% for any meiotic event.

"Linkage disequilibrium" or "allelic association" means the preferential association of a particular allele, locus, gene or genetic marker with a specific allele, locus, gene or genetic marker at a nearby chromosomal location more frequently than expected by chance for any particular allele frequency in the population.

An "oligonucleotide" can be DNA or RNA, and single- or double-stranded. Oligonucleotides can be naturally occurring or synthetic, but are typically prepared by synthetic means.

The term "primer" refers to an oligonucleotide capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is preferably a single-stranded oligonucleotide. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term "primer" may refer to more than one primer, particularly in the case where there is some ambiguity in the information regarding one or both ends of the target region to be amplified. For instance, if a region shows significant levels of polymorphism or mutation in a population, mixtures of primers can be prepared that will amplify alternate sequences. A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in an ELISA), biotin, or haptens and proteins for which antisera or monoclonal antibodies are available. A label can also be used to "capture" the primer, so as to facilitate the immobilization of either the primer or a primer extension product, such as amplified DNA, on a solid support.

"Chromosome 1 set" means the two copies of chromosome 1 found in somatic cells or the one copy in germ line cells of a patient or family member. The two copies of chromosome 1 may be the same or different at any particular allele, including alleles at or near the schizophrenia locus. The chromosome 1 set may include portions of chromosome 1 collected in chromosome 1 libraries, such as plasmid, yeast, or phage libraries, as described in Sambrook et al., Molecular Cloning, 2nd Edition, and in Mandel et al., Science 258:103-108 (1992).

"Penetrance" is the percentage of individuals with a defective gene who show some symptoms of a trait resulting from that defect. Expressivity refers to the degree of expression of the trait (e.g., mild, moderate or severe).

"Polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair. Polymorphic markers suitable for use in the invention include restriction fragment length polymorphisms, variable number of tandem repeats (VNTR's), hypervariable regions, minisatellites, dinucleotide repeats, trinucleotide repeats, tetranucleotide repeats, and other microsatellite sequences.

"Restriction fragment length polymorphism" (RFLP) means a variation in DNA sequence that alters the length of a restriction fragment as described in Botstein et al., Am. J. Hum. Genet. 32:314-331 (1980). The restriction fragment length polymorphism may create or delete a restriction site, thus changing the length of the restriction fragment. For example, GAATTC is the DNA sequence, together with its complementary strand, CTTAAG which comprises the recognition and cleavage site of the restriction enzyme EcoRI. Replacement of any of the six nucleotides on either strand of DNA with a different nucleotide destroys the EcoRI site. This RFLP can be detected by, for example, amplification of a target sequence including the polymorphism, digestion of the amplified sequence with EcoRI, and size fractionation of the reaction products on an agarose or acrylamide gel. If the only EcoRI restriction enzyme site within the amplified sequence is the polymorphic site, the target sequences comprising the restriction site will show two fragments of predetermined size, based on the length of the amplified sequence. Target sequences without the restriction enzyme site will only show one fragment, of the length of the amplified sequence. Similarly, the RFLP can be detected by probing an EcoRI digest of Southern blotted DNA with a probe from a nearby region such that the presence or absence of the appropriately sized EcoRI fragment may be observed. RFLP's may be caused by point mutations which create or destroy a restriction enzyme site, VNTR's, dinucleotide repeats, deletions, duplications, or any other sequence-based variation that creates or deletes a restriction enzyme site, or alters the size of a restriction fragment.

"Variable number of tandem repeats" (VNTR's) are short sequences of nucleic acids arranged in a head to tail fashion in a tandem array, and found in each individual, as described in Wyman et al., Proc. Nat. Acad. Sci. 77:6754-6758 (1980). Generally, the VNTR sequences are comprised of a core sequence of at least 16 base pairs, with a variable number of repeats of that sequence. Additionally, there may be variation within the core sequence, Jefferys et al., Nature 314:67-72 (1985). These sequences are highly individual, and perhaps unique to each individual. Thus, VNTR's may generate restriction fragment length polymorphisms, and may additionally serve as size-based amplification product differentiation markers.

"Microsatellite sequences" comprise segments of at least about 10 base pairs of DNA consisting of a variable number of tandem repeats of short (1-6 base pairs) sequences of DNA (Clemens et al., Am. J. Hum. Genet. 49:951-960 1991). "Microsatellite sequences" are generally spread throughout the chromosomal DNA of an individual. The number of repeats in any particular tandem array varies greatly from individual to individual, and thus, microsatellite sequences may serve to generate restriction fragment length polymorphisms, and may additionally serve as size-based amplification product differentiation markers.

A "marker" is referred to as fully "informative" for a particular individual if the configuration of alleles observed in the family allow for the unambiguous determination of parental origin of the alleles of a child. For example, if the mother has a "1" and "2" allele, while the father has a "3" and "4" allele, then it is possible to unambiguously assign the parental origin of alleles in each of the four possible combinations in the children (1-3, 1-4, 2-3, 2-4). A marker is partially informative when unambiguous determination of parental origin is possible for only certain children. For example, if both parents have a "1" and "2" allele, then the parental origins of the alleles may be unambiguously determined for children with the genotypes 1-1 and 2-2, but not for the children with the genotype 1-2. If one parent is homozygous for a marker, the marker will be only partially informative, and the inheritance from that parent cannot be traced. If the marker is homozygous in both parents, the marker is fully uninformative for the transmission from them to their children, even though their children may be heterozygous and thus informative for the transmission of that marker to the next generation.

A "binding complex" used herein refers to the complex formed between NOS1AP protein and a test compound. The test compound may be an antibody, a protein peptide, or any other molecule which exhibits binding affinity for NOS1AP-S or NOS1AP-L.

As used herein, "shRNA" or short hairpin RNA, or small hairpin RNA is an RNA molecule that contains a sense strand, antisense strand, and a short loop sequence between the sense and antisense fragments. shRNA can be cloned into a vector, allowing for expression by a pol III type promoter. The expressed shRNA is then exported into the cytoplasm where it is processed by dicer into siRNA which then get incorporated into the siRNA induced silencing complex (RISC). Typically, shRNA molecules consist of short complementary sequences separated by a small loop sequence wherein one of the sequences is complimentary to the gene target as provided in U.S. Application Publication No. 20050032733.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting NOS1AP or CPE mRNA may be between 10-35 nucleotides in length.

The terms "agent" and "compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the SNP containing nucleic acids described herein or their encoded proteins. Agents are evaluated for potential biological activity by inclusion in screening assays described herein.

The term "modulate" as used herein refers increasing/promoting or decreasing/inhibiting. For example, the term modulate refers to the ability of a compound or test agent to interfere with or inhibit signaling or binding activity of a gene or protein of the present invention. Preferably the modulation is an inhibition of protein binding, for example, between NOS1AP and CPE.

II. METHODS OF TREATMENT AND IDENTIFYING NEW DRUGS

The discovery of novel NOS1AP isoforms, i.e., NOS1AP-L and NOS1AP-S genes (SEQ ID NOS: 1 and 3 respectively), facilitates the development of new therapeutic agents and methods of treatment for neuropsychiatric disorders, such as schizophrenia, schizoaffective disorders and bipolar disorders.

The provision of NOS1AP-L and NOS1AP-S proteins encoded by the newly discovered NOS1AP variants facilitates the development of screening assays to identify NOS1AP binding or interacting molecules and/or other agents or test compounds that interact with the same and design of agents that agonize or antagonize this interaction. These methods allow for the identification of compounds or agents which modulate (i.e., inhibit or promote) NOS1AP binding with NOS1AP binding proteins. Such agents include monoclonal antibodies against NOS1AP protein, fragments of NOS1AP protein that compete with the NOS1AP protein for binding, and synthetic peptides or analogs thereof selected from random combinatorial libraries. See, e.g., Ladner et al., U.S. Pat. No. 5,223,409 (1993) (incorporated by reference in its entirety herein). Therapeutic agents can also include transcription factors, and the like, which regulate expression of the NOS1AP gene as described hereinbelow.

Additionally, inhibitors of protein interactions or protein function could be utilized to treat patients, for example, patients with schizophrenia, schizoaffective disorder and bipolar disorder. Thus, an optional feature of the invention is the use of compounds or agents with the ability to inhibit the function of a protein. For example, the invention may optionally include the feature of administering known inhibitors of CPE, such as, ϵ-aminocaproic acid and Guanidinoethylmercaptosuccinic Acid (GEMSA), both described in U.S. Pat. No. 7,176,008, bromoacetyl-D-arginine as described in (J. Cell. Biochem. (1988) 38(4):279-289), DL-2-mercaptomethyl-3-guanidinoethyldiiopropanoic acid (MGTA) and p-chloromercuriphenylsulfonate as described in (Immunol. Reviews (1998) 161:129-141), and carboxypeptidase inhibitors described in U.S. Pat. No. 6,489,319.

III. METHODS OF DIAGNOSIS AND DIAGNOSTIC KITS

The present discovery that NOS1AP-L (SEQ ID NO: 1) and NOS1AP-S (SEQ ID No. 3) are overexpressed in patients having schizophrenia or bipolar disease, provides additional means for diagnosing such patients. Such diagnosis may be accomplished by providing one or more oligonucleotides that bind specifically to a segment of NOS1AP-L or NOS1AP-S mRNA, thereby assessing the expression levels of NOS1AP gene. The diagnosis may also be accomplished by providing one or more agents, such as an antibody (monoclonal or polyclonal), that bind specifically to NOS1AP protein, thereby assessing the production levels of NOS1AP protein. In a preferred embodiment, antibodies immunologically specific for the NOS1AP-S protein are provided. Such antibodies have utility for detection and subcellular localization of the NOS1AP-S protein described herein.

The present invention also includes kits for the practice of the methods of the invention. The kits comprise a vial, tube, or any other container which contains one or more oligonucleotides, which hybridizes to a segment of NOS1AP-S mRNA. The kits may include positive or negative control reactions or markers, molecular weight size markers for gel electrophoresis, and the like. The kits usually include labeling or instructions indicating the suitability of the kits for diagnosing neuropsychiatric disorders and indicating how the oligonucleotides are to be used for that purpose. The term "label" is used generically to encompass any written or recorded material that is attached to, or otherwise accompanies the diagnostic at any time during its manufacture, transport, sale or use.

It has been proposed that altered regulation of NOS1AP gene in utero may be associated with the later development of schizophrenia. Accordingly, methods are provided herein for isolating fetal cells present in maternal circulation, performing PCR, and assessing such cells for altered levels of NOS1AP nucleic acid production, an elevation in NOS1AP gene expression relative to normal control fetal cells being indicative of a predisposition to the development of neuropsychiatric disorders. Thus, a kit of the invention may include the necessary reagents for isolating fetal cells from the maternal circulation (See WO/2002/077604) and primers for amplifying NOS1AP-L and/or NOS1AP-S.

It is also possible to determine NOS1AP-L or NOS1AP-S levels in olfactory neurons isolated from adult patients. See Feron et al. (1998) "New Techniques for Biopsy and Culture of Human Olfactory Epithelial Neurons" in Arch. Otolaryngol. Head Neck Surg. 124:861. A demonstrable elevation in NOS1AP-S or NOS1AP-L in such neurons would provide a positive indicator of an increased risk of developing schizophrenia.

Additionally, Segalat et al. report that NOS1AP expression can also be assessed using muscle tissue. See "Segalat et al. (2004) NOS1AP expression in skeletal muscle is regulated by position, repair, NOS activity and dystrophy. Accordingly, muscle biopsies may be obtained from patients at risk and NOS1AP expression levels assessed.

IV. USES OF NOS1AP NUCLEIC ACID

The nucleic acids encoding the NOS1AP-L and NOS1AP-S genes may be used as research tools to identify other genes or proteins that are involved in the maintenance and promotion of neuropsychiatric disorders. For example, the sequence information in the NOS1AP gene may be used to advantage to identify and characterize other genes of varying degrees of relation to the genes of the invention thereby enabling further characterization of the aberrant neural cellular processes associated with neuropsychiatric disorders. Additionally, the nucleic acids encoding NOS1AP gene(s) may be used to identify genes encoding proteins that interact with NOS1AP protein e.g., by the "interaction trap" technique), which should further accelerate identification of the components involved in the progression of neuropsychiatric disorders.

Nucleic acid molecules, or fragments thereof, encoding NOS1AP genes, for example, may also be utilized to control the production of NOS1AP protein, thereby regulating the amount of protein available to participate in the maintenance and progression of the neuropsychiatric state. Antisense oligonucleotides corresponding to essential processing sites in NOS1AP mRNA molecules may be utilized to inhibit protein production in targeted cells. Alternatively, SiRNA molecules based on the coding sequences can be prepared and assessed for the ability to down regulate NOS1AP production. Such siRNA molecules can be obtained from Dharmacon. Alterations in the physiological amount of NOS1AP protein may dramatically affect the activity of other protein factors involved in the maintenance and progression of neuropsychiatric disorders.

The nucleic acids encoding the NOS1AP genes disclosed herein may be cloned into expression systems which may be used as screening tools to identify compounds that modulate protein activity. Modulation of such activity, for example, may be assessed by measuring alterations in NOS1AP activities in the presence of the test compound. Test compounds can also be assessed for the induction and/or suppression of expression of other nucleic acids and proteins that are involved in the maintenance and promotion of neuropsychiatric disorders.

V. NOS1AP PROTEINS AND ANTIBODIES

Purified NOS1AP proteins, or fragments thereof, may be used to produce polyclonal or monoclonal antibodies which also may serve as sensitive detection reagents for the presence and accumulation of such proteins (or complexes containing such protein) in mammalian cells. Recombinant techniques enable expression of fusion proteins containing part or all of NOS1AP proteins of the invention. The full length protein or fragments of the protein may be used to advantage to generate an array of monoclonal antibodies specific for various epitopes of NOS1AP-L and NOS1AP-S proteins, for example, thereby providing even greater sensitivity for detection of other variants in cells.

Polyclonal or monoclonal antibodies immunologically specific for the NOS1AP protein of the invention may be used in a variety of assays designed to detect and quantitate the protein. Such assays include, but are not limited to: (1) flow cytometric analysis; (2) immunochemical detection/localization of NOS1AP protein in cells derived from the brain, muscle cells, fetal neuronal cells in maternal circulation and/or olfactory neuronal cells in various stages of neuronal differentiation; and (3) immunoblot analysis (e.g., dot blot, Western blot) of extracts from various cells. Additionally, as described above, antibodies specific for the NOS1AP-S protein can be used for purification of such proteins and any associated subunits (e.g., affinity column purification, immunoprecipitation).

In accordance with the present invention, the NOS1AP gene has been localized to a specified region on chromosome 1 and encodes an alternatively spliced variant of the NOS1AP gene. It appears likely that mutations in the promoter or 5' UTR region or the coding sequence of the NOS1AP-L or NOS1AP-S genes are associated with the neuropsychiatric phenotype. In one aspect of the invention, the promoter and coding sequence of the NOS1AP-L gene isolated from brain cells will be screened for mutations. See FIG. 7. Such screening should effectively identify genetic changes associated with altered expression levels of the NOS1AP gene. The promoter fragment or 5' UTR of the NOS1AP gene, employed in drug screening assays may either be free in solution, affixed to a solid support or within a cell. One method of drug screening utilizes eukaryotic or prokaryotic host cells which are stably transformed with recombinant polynucleotides expressing the polypeptide, a fragment thereof, or a NOS1AP gene promoter/reporter gene construct, preferably in competitive binding assays. Such cells, either in viable or fixed form, can be used for standard binding assays. One may determine, for example, formation of complexes between a NOS1AP polypeptide or promoter and the agent being tested, or examine the degree to which the formation of a complex between a NOS1AP polypeptide or fragment and a known ligand is interfered with by the agent being tested.

Another technique for drug screening provides high throughput screening for compounds having suitable binding affinity to the NOS1AP-L or NOS1AP-S promoter or the encoded NOS1AP polypeptides and is described in detail in Geysen, PCT published application Wo 84/03564, published on Sep. 13, 1984. Briefly stated, large numbers of different, small peptide test compounds are synthesized on a solid substrate, such as plastic pins or some other surface. The peptide test compounds are reacted with NOS1AP gene promoter disclosed herein or NOS1AP polypeptide and washed. Bound NOS1AP gene promoter or polypeptide is then detected by methods well known in the art.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, one first determines the three-dimensional structure of a protein of interest (e.g., NOS1AP-L or NOS1AP-S protein) or, for example, of NOS1AP protein-substrate complex, by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides (e.g., NOS1AP-L or NOS1AP-S protein) may be analyzed by an alanine scan (Wells, 1991) Meth. Enzym. 202:390-411. In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from chemically or biologically produced banks of peptides. Selected peptides would then act as the pharmacore.

Thus, one may design drugs which have, e.g., improved NOS1AP polypeptide activity or stability or which act as inhibitors, agonists, antagonists, etc. of the NOS1AP polypeptide activity. By virtue of the availability of cloned the NOS1AP sequences described herein, sufficient amounts of NOS1AP polypeptide may be made available to perform such analytical studies as x-ray crystallography. In addition, the knowledge of NOS1AP protein sequence provided herein will guide those employing computer modeling techniques in place of, or in addition to x-ray crystallography.

In a particularly preferred embodiment of the invention, the promoter region of the NOS1AP gene is cloned upstream of a reporter gene. See FIG. 7. Reporter genes suitable for this purpose include, without limitation, beta galactosidase, luciferase, chloramphenicol acetyltransferase, and green fluorescent protein. Methods for operably linking the coding regions for the reporter genes to NOS1AP promoter sequence or 5' UTRs are well known to those of ordinary skill in the art. In an alternative embodiment, SNPs previously associated with schizophrenia can be introduced into the promoter sequence provided herein and their effects on NOS1AP expression level and protein activity assessed.

Following introduction of such DNA constructs into recipient host cells, the cells may be contacted with agents suspected of affecting NOS1AP activity. Agents capable of altering expression levels of the reporter gene may prove efficacious in regulating the expression of the NOS1AP gene, thereby having therapeutic advantage in the treatment of neuropsychiatric disorders or other disorders where altered expression of the NOS1AP gene plays a role.

VI. PHARMACEUTICALS AND PEPTIDE THERAPIES

The discovery of the NOS1AP gene facilitates the development of pharmaceutical compositions useful for treatment and diagnosis of those syndromes and conditions associated with neuropsychiatric disorders. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

From the foregoing discussion, it can be seen that nucleic acids encoding the NOS1AP proteins described herein, expression vectors for producing the same, and antibodies immunologically specific for the protein of the invention can be used to detect the expression the NOS1AP gene and alter NOS1AP protein accumulation for purposes of assessing the genetic and protein interactions involved in the development and progression of neuropsychiatric disorders.

The detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody or a biotin/avidin ligand binding arrangement, as is known in the art. The immunodetection methods of the present invention have evident utility in the diagnosis of neuropsychiatric disorders. Here, a biological or clinical sample suspected of containing either the encoded protein or peptide or corresponding antibody is used. However, these embodiments also have applications to non-clinical samples, such as in the titering of antigen or antibody samples, in the selection of hybridomas, and the like. In the clinical diagnosis or monitoring of patients with neuropsychiatric disorders, the detection of NOS1AP antigens, or an increase in the levels of such antigens, in comparison to the levels in a corresponding biological sample from a normal subject may be indicative of a patient with neuropsychiatric disorders. The basis for such a diagnostic methods lies, in part, with the finding that presence of the NOS1AP nucleic acid is associated with the neuropsychiatric disorder phenotype. By extension, it may be possible that this nucleic acid produces elevated levels of encoded NOS1AP protein for example, which may prove useful as a neuropsychiatric marker. Cell lines expressing the nucleic acids encoding NOS1AP protein or variants thereof may be used in screening methods to identify agents, which modulate their function.

In one broad aspect, the present invention encompasses kits for use in detecting expression of NOS1AP proteins in brain tissues, most preferably in neuronal tissue. Such a kit may comprise one or more pairs of primers for amplifying nucleic acids corresponding to the NOS1AP genes described herein. The kit may further comprise samples of total mRNA derived from tissue of various physiological states, for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting cells in a biological sample comprising oligonucleotide probes effective to bind with high affinity to NOS1AP mRNA in a Northern blot assay and containers for each of these probes. In a further embodiment, the invention encompasses a kit for use in detecting NOS1AP-S proteins in cells comprising antibodies specific for NOS1AP-S proteins.

The following examples are provided to illustrate various embodiments of the present invention. They are not intended to limit the invention in any way.

Example I

The NOS1AP gene (GenBank Accession No. NM_014697) has been previously identified as an attractive candidate for schizophrenia susceptibility. NOS1AP was first identified in the rat as a neuronal nitric oxide synthase (nNOS) binding protein, capable of disrupting the association of nNOS with the postsynaptic density scaffolding proteins PSD93 and PSD95 through the binding of the C-terminus of NOS1AP to nNOS (Jaffrey et al. 1998). The interaction between nNOS and PSD93 and PSD95 is important in targeting nNOS to the postsynaptic N-methyl-D-aspartate (NMDA) receptor complex, and facilitates the tight coupling between activation of the NMDA receptor and nNOS, allowing nNOS activation by $Ca^{++}$ influx through the NMDA receptor, producing NMDA receptor-mediated nNO release into the synaptic structures (Brenman et al. 1996a; Brenman et al. 1996b). This places NOS1AP at the site of NMDA glutamate neurotransmission, long proposed to be involved in schizophrenia (reviewed in Coyle et al. 2003). NOS1AP can also serve as an nNOS adaptor protein, with the N-terminus either binding to a direct target of NO-mediated activation by S-nitrosylation (Fang et al. 2000) or to Synapsin (Jaffrey et al. 2002), resulting in the localization of nNOS to the presynaptic terminals.

Sequencing of the coding region of NOS1AP in individuals from the Canadian linkage sample has failed to identify any coding mutations associated with illness (Brzustowicz et al. 2004), consistent with current results for other candidate genes for schizophrenia (Harrison and Owen 2003). NOS1AP has a large, approximately 300 kb, genomic extent, only 1.5 kb of which represents coding sequence. Therefore there are many potential sites for regulatory sequences that could be disrupted and lead to altered gene expression. In the present invention, a human cDNA library was screened to identify possible alternative splice forms of NOS1AP. The expression of NOS1AP by quantitative RT-PCR was investigated in the Stanley Array Collection (Torrey et al. 2000), derived from post-mortem tissue from the dorsolateral prefrontal cortex (DLPFC) of individuals with schizophrenia, bipolar disorder, and psychiatrically normal controls.

Materials and Methods

I. Identification and Characterization of NOS1AP Transcripts:

A human fetal brain arrayed cDNA library (Origene Technologies, Catalog Number LLFB-1001) was screened using the supplier's protocol by PCR amplification using primers from NOS1AP exon 10 (Ex10-F: AAATCAACAACCT-TGCCTAACG (SEQ ID No. 5), Ex10-R: GAAAGCACTC-CAGCTTCACC(SEQ ID No. 6)). Individual positive clones were sequenced using a CEQ 8000 (Beckman Coulter). Transcripts were further characterized by 3' and 5' RACE, performed with RACE-ready cDNA from human brain (Ambion). For each reaction a pair of nested PCR primers were designed from full-length and short-form 5' UTR sequences (5RACEL: GAAGGCGTCCTCGTTGTGCAAGG (SEQ ID No. 7)/5RACELn: TTGTGCAAGGGGATCCGCAGGTCG (SEQ ID No. 8), 5RACES: TTAGAGGTTCCTG-GAGGGTGGTGC (SEQ ID No. 9)/5RACESn: TTGAGTC-CAAGGAGAGGGTAGTGG (SEQ ID No. 10)) and 3'UTR sequence (3RACE1: AATGAATGCAAGCTGATAGCT-GAGACTG (SEQ ID No. 11)/3RACE1n: TGAATCACTGC-CACTTGGGTCAGG (SEQ ID No. 12), 3RACE2: AGAAG-GAAGAACCAGGAAAGTGAGATCC (SEQ ID No. 13)/3RACE2n: ATCCAGTGTGGCTGAGCCTACCTAGC (SEQ ID No. 14), and 3RACE3: ATGTGGATG-GAGAGGGCTTGT (SEQ ID No. 15)/3RACE3n: GTGAG-GAAGGCCGCTTCTAAAT (SEQ ID No. 16)) and were used in conjunction with a set of universal nested primers (supplied). Products were cloned into TOPO TA cloning vector (Invitrogen) and sequenced using a CEQ 8000 (Beckman Coulter).

II. Human Postmortem Samples:

RNA and DNA samples from the Stanley Array Collection of the Stanley Brain Collection (Torrey et al. 2000) were analyzed. This is a collection of biomaterials derived from post-mortem brain specimens from 35 individuals with schizophrenia, 35 individuals with bipolar disorder, and 35 psychiatrically normal controls. Diagnoses were made by two senior psychiatrists, using DSM-IV criteria, based on medical records, and when necessary, telephone interviews with family members. Diagnoses of unaffected controls were based on structured interviews by a senior psychiatrist with family member(s) to rule out Axis I diagnoses.

Specimens were collected, with informed consent from next-of-kin, by participating medical examiners between January 1995 and June 2002. The specimens were all collected, processed, and stored in a standardized way. Exclusion criteria for all specimens included: 1) significant structural brain pathology on post-mortem examination by a qualified neuropathologist, or by pre-mortem imaging; 2) History of significant focal neurological signs pre-mortem; 3) History of central nervous system disease that could be expected to alter gene expression in a persistent way; 4) Documented IQ<70; or 5) Poor RNA quality. RNA integrity and purity were determined with an Agilent 2100 Bioanalyzer. Degradation was defined as a shift in the RNA size distribution towards smaller fragments and a decrease in fluorescence signal of ribosomal peaks. Additional exclusion criteria for unaffected controls included age less than 30 (thus, still in the period of maximum risk) and substance abuse within one year of death or evidence of significant alcohol-related changes in the liver.

DNA and RNA from Brodmann's area 46 (DLPFC) was available for all subjects. Genotyping and expression analyses were conducted with the samples coded to keep investigators blind to diagnostic status. After the blind was broken, diagnostic status and a range of clinical variables were provided for analysis. These included gender, race, age at time of death, age of onset, post-mortem interval (PMI), brain pH, total brain weight, hemisphere used for RNA extraction, smoking status at time of death (coded as non-smoking for individuals who smoked previously but had quit), antipsychotic status at time of death, and lifetime antipsychotic exposure in fluphenazine milligram equivalents. In addition, lifetime alcohol and substance use were each rated on a scale of 0 to 5 using the categories "little or none", "social", "moderate past", "moderate present", "heavy past", and "heavy present". Overall, the sample was 66% male, with an average age at death of 44 years (S.D. 8.9, range of 19 to 64), and was predominantly Caucasian (97%), with one African American subject with bipolar disorder, one Native American subject with bipolar disorder, and one Hispanic individual with schizophrenia. Smoking status at time of death was available for 67 subjects, with 72% of the sample smokers. Lifetime alcohol use estimates were available on all but one subject, with 57% of the sample reporting no, little, or social use, 17% reporting past or present moderate use, and 26% reporting past or present heavy use. Lifetime substance use estimates were available on all but two subjects, with 65% of the sample reporting no, little, or social use, 16% reporting past or present moderate use, and 19% reporting past or present heavy use. The average age of onset for the schizophrenia group was 21.3 years (S.D. 6.1, range of 9 to 34) and for the bipolar group was 25.1 years (S.D. 9.1, range of 14 to 48). Further information about the Stanley Array Collection is available from the Stanley Medical Research Institute.

III. RNA Quantification:

Total RNA (5 μg) was treated with the DNA-free Kit (Ambion) in accordance with the manufacturer's procotol to eliminate DNA contamination. The resulting DNase-treated RNA was used in a 40 μl reverse transcriptase reaction to synthesize cDNA following the SuperScript II First-Strand cDNA Synthesis protocol (Invitrogen), including optional RNaseOUT treatment. Samples were then quantified using real-time PCR. The previously described primer pair NN05224/NN05225 (HUGE database clone KIAA0464) was used for quantification of full-length NOS1AP (Ohara et al. 1997; Kikuno et al. 2004). This primer pair produces a 338 bp product that spans the boundary of exons 7 and 8. The primers specific for NOS1AP-S were designed using Primer Express Software Version 2.0 (Applied Biosystems). The forward primer (Short-F: CATTCATGTCCCTCTCT-TCTCTC (SEQ ID No. 17)) is located in the 5' UTR that is unique to the short form transcript, the reverse primer (Short-R: AATGCAGGTCCTCTGGCTTAG (SEQ ID No. 18)) is located within exon 10, and the pair produces a 321 bp product that spans the boundary of exons 9 and 10. The housekeeping gene beta-actin was used as reference gene to normalize the total RNA input. The forward (beta-actin-F: CATCCTCACCCTGAAGTACCC (SEQ ID No. 19)) and reverse (beta-actin-R: GAGAAGATGACCCAGATCAT-GTTT (SEQ ID No. 20)) primers produce a 184 bp product that spans the boundary of exons 3 and 4. Real time PCR analysis was conducted using 1 μl of a 1:5 dilution of cDNA, 0.1 μM of each primer, and 5 μl Sybr Green Master Mix (Applied Biosystems) in a total reaction volume of 10 μl in a 384 well plate on an ABI Prism 7900HT sequence detector system (Applied Biosystems). Samples were initially warmed to 50° C. for 2 minutes followed by activation of the AmpliTaq Gold DNA polymerase by heating to 95° C. for 10 minutes. PCR amplification was performed with 40-50 cycles of 95° C. for 30s, 58° C. (full-length experiments) or 61° C. (short-form experiments) for 40s, and 72° C. for 1 minute. Each real-time PCR assay was repeated three times. The standard curve used for determining the relative quantity of each isoform in each sample was constructed by the amplification of serial dilutions of pooled brain cDNA. In each experiment, the $R^2$ value of the standard curve was greater than 0.98 and the no-template control produced no detectable signal. Dissociation curve analysis was conducted on all PCR products to assure that only a single product was present in the reaction. Real-time PCR data acquisition and analysis were performed using SDS v2.0 software (Applied Biosystems).

IV. SNP Genotyping:

DNA samples from the Stanley Array Collection were genotyped for rs1415263, rs4145621, and rs2661818 by a primer extension strategy (Pyrosequencing) using the automated PSQ HS96A platform as described in Brzustowicz et al. 2004.

V. Statistical Analyses:

RNA amounts were quantified by the ABI Relative Quantitation of Gene Expression protocol (Applied Biosystems). The results from three repeat assays were averaged to produce a single mean quantity value for each mRNA for each subject. The quantity values of the target gene were then normalized over the quantity values of the reference gene (beta-actin) to produce normalized expression quantities. These are unitless measures of the relative amount of transcript that is present in each individual.

Normalized expression quantities and subject variables were analyzed with SAS v8.2 for UNIX software (SAS Institute Inc.). Most potentially confounding variables were tested for correlation with NOS1AP expression using all subjects, although exposure to antipsychotics (either as a dichotomous trait or a quantitative estimate of total lifetime exposure) was examined only in subjects with bipolar disorder or schizophrenia. Normally distributed variables (age at death, post-mortem interval, brain pH, and brain weight) were tested with Pearson's product moment correlation, dichotomous variables (gender, brain hemisphere analyzed, smoking status at time of death, and history of exposure to antipsychotic medication) with point biserial correlation, and ranked variables (lifetime alcohol use and lifetime substance abuse) with Spearman's correlation. Quantitative lifetime antipsychotic exposure was tested with Pearson's product moment correlation after log transformation to normalize the distribution of the data. The relationship between gene expression levels and diagnostic group was analyzed by point biserial correlation, and the relationship between gene expression levels and age of onset within the bipolar and schizophrenia groups was tested with Pearson's product moment correlation. The relationship between genotype and NOS1AP expression was analyzed by Spearman's rank correlation, with the heterozygotes ranked between the homozygotes.

SNPs were analyzed for association to schizophrenia and bipolar disorder using Fisher's exact test. Two by two tables were constructed comparing the frequency of the two alleles for each SNP in cases from a single diagnostic category versus controls. Since three SNPs that had demonstrated significant association to schizophrenia in a prior study (Brzustowicz et al. 2004) were tested, one-sided p-values reflecting association of the alleles previously found to be associated with schizophrenia are reported.

Results

I. Identification and Characterization of Two Human NOS1AP Isoforms:

Screening of a human fetal brain cDNA library resulted in the isolation of four distinct clones. Three clones ("NOS1AP full-length", having the sequence of SEQ ID No. 1) contain inserts of approximately 2.5 kb, corresponding to exons 1-10, as previously described in the NCBI reference sequence for NOS1AP (GenBank Accession No. NM_014697), except that exon 4 from these clones was missing the first 15 bp listed in the reference sequence. These transcripts are predicted to produce a 501 amino acid full-length NOS1AP protein (SEQ ID No. 2) which contains an in-frame deletion of the 5 amino acids sequence Glu-Leu-Leu-Leu-Leu (SEQ ID No. 21), when compared to the NOS1AP protein previously disclosed (GenBank Accession No. NP_055512). The fourth clone ("NOS1AP short-form", having the sequence of SEQ ID No. 3) contains an insert of 4 kb with a unique 5' UTR corresponding to genomic sequence from intron 8, followed by exons 9 and 10, and a 3' UTR longer than that contained by the other clones or in the reference sequence. This transcript is predicted to produce a 211 amino acid protein (SEQ ID No. 4), including 18 novel amino acids at the amino terminus, and will contain the NOS1AP PDZ-binding domain.

The previously undescribed transcript of NOS1AP-S was further characterized by 5' and 3' RACE. The 5' UTR was 2,367 bp, while the longest 3' RACE product ended 2,556 bp downstream of the stop codon. From these results, the total length of the short-form mRNA was calculated to be 5,559 bp. Due to the much longer 5' and 3' UTRs, the NOS1AP transcript encoding NOS1AP-S protein (SEQ ID No. 4) is actually significantly longer than the transcript that encodes the full-length protein (SEQ ID No. 2). The gene, transcripts, and predicted protein structures of the two forms are shown in FIG. 1.

Figure 2:
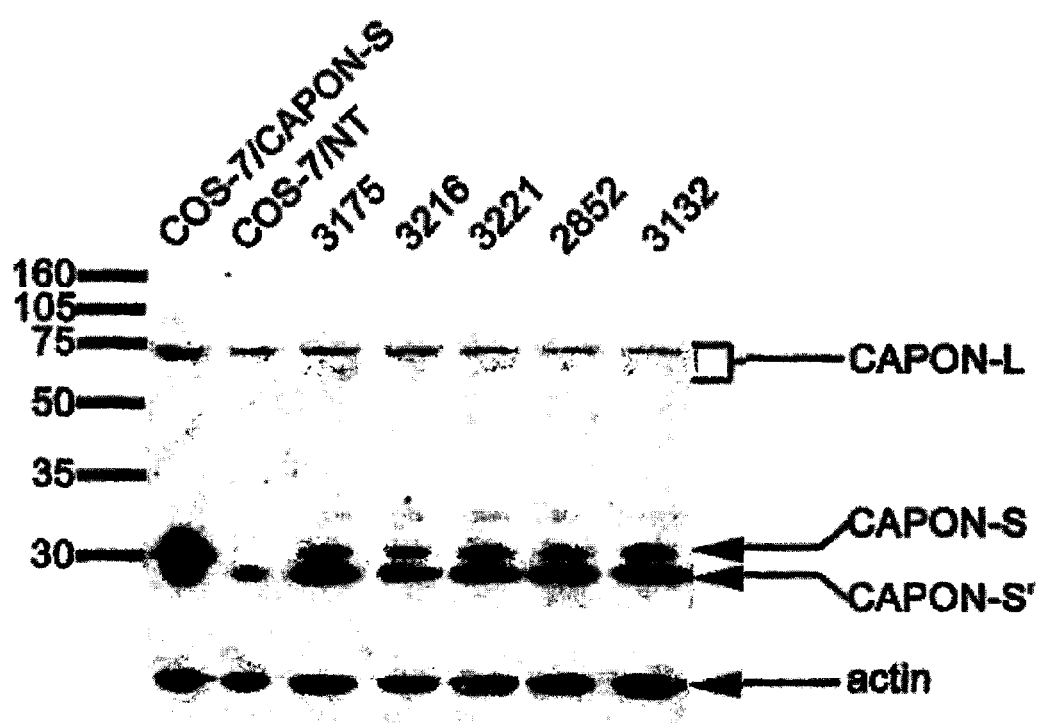
FIG. 2 is a Western Blot of NOS1AP protein isoforms in DLPFC (dorsolateral prefrontal cortex) from normal control individuals. Tissue from Brodmann's area 46 (DLPFC) from five individuals was homogenized in TEE. Proteins were resolved by SDS-PAGE and transferred to PVDF membrane. Blots were probed with rabbit polyclonal antibodies to NOS1AP and actin, and proteins were detected using chemiluminescence. Band intensities for NOS1AP-L (NOS1AP full-length), NOS1AP-S(NOS1AP short-form), and NOS1AP-S+NOS1AP-S' were calculated and normalized to the intensities of the corresponding actin bands. Untransfected COS-7 cells expressing NOS1AP-L and NOS1AP-S' (CPS-7/NT) and COS-7 cells expressing recombinant NOS1AP-S(COS-7/NOS1AP-S) were used as controls for these proteins. NOS1AP-L appears to include multiple bands, possibly due to phosphorylation.

Protein and total RNA were extracted from Brodmann's area 46 (DLPFC) of postmortem samples from five normal controls, COS-7 cells that had been transfected with cDNA encoding NOS1AP-S protein (SEQ ID No. 4), and untransfected COS-7 cells that normally express the full-length NOS1AP protein (SEQ ID No. 2). Western blots of these samples were probed with a rabbit polyclonal antibody raised against the carboxyl terminus of NOS1AP. This antibody is predicted to interact with both the full-length and short-form of NOS1AP, since the antigen used to generate the antibody is in the carboxyl termini of both forms. Bands were observed at the expected sizes, near the 75 kDa marker for the full-length protein and near the 30 kDa marker for the short-form (FIG. 2). There appears to be two smaller forms of the full-length NOS1AP (SEQ ID No. 2) (NOS1AP-L bracket, FIG. 2), which could be due to posttranslational modification (i.e., phosphorylation) of NOS1AP. For example, analysis by software designed to identify potential sites for phosphorylation by protein kinase C identified five such sites in the full-length NOS1AP sequence (SEQ ID No. 2). The NOS1AP-S (SEQ ID No. 4) appears as a doublet, although the presence of the lower band (NOS1AP-S') in untransfected COS-7 cells may indicate that this band is caused by recognition by the NOS1AP antibody of a cross-reacting protein. The appearance of the higher band (NOS1AP-S) in the transfected cells, which clearly comigrates with a band in human brain tissue, indicates that the short-form transcript is translated into a protein of the expected size in DLPFC.

As protein samples were not available for the Stanley Array Collection samples, the correlation between protein and RNA expression was tested using the normal control brain samples to determine if RNA levels could be used as a reasonable indicator of protein expression for NOS1AP. NOS1AP protein levels were quantified from Western blot image analysis and were normalized to levels of actin protein, while RNA levels were quantified by reverse-transcription real-time PCR normalized to levels of ACTB (beta-actin). For full-length NOS1AP (SEQ ID No. 2), the correlation between protein and RNA levels was significant ($p=0.019$) with $r=0.94$. For NOS1AP-S (SEQ ID No. 4), the correlation was also significant ($p=0.0049$) with $r=0.97$ between the RNA and protein levels of the S band, which corresponds to the size of the cloned NOS1AP product. While it seems likely that the S' band represents a cross-reacting protein, given its presence in untransfected COS-7 cells, it is possible that it could represent a modified form of the short-form protein (SEQ ID No. 4). Considering the NOS1AP-S product as the sum of the S and S' bands, the correlation with RNA levels remained significant ($p=0.030$), with $r=0.91$.

II. Analysis of NOS1AP Isoform Expression by Diagnosis:

Expression levels of both NOS1AP isoforms were determined by reverse-transcription real-time PCR for all 105 samples from the Stanley Array Collection. Expression levels were normalized to ACTB (beta-actin), and these normalized relative expression levels were used for all subsequent analyses. No significant correlations were detected between mRNA levels of either NOS1AP isoform and the potentially confounding variables of age at death, PMI, brain pH, brain weight, gender, hemisphere, smoking status at time of death, lifetime alcohol use, or lifetime substance abuse (Table 3). NOS1AP expression levels were found to be significantly ($p<0.001$) correlated with length of sample storage for both isoforms (Table 3). Therefore, for all subsequent analyses storage time was used as covariate.

TABLE 3

Correlations Between NOS1AP Isoform Expression and Possible Confounding Variables

| Variable | Full-Length | | Short-Form | |
|---|---|---|---|---|
| | Correlation | p-value[a] | Correlation | p-value[a] |
| Age[b] | −0.05 | 0.63 | −0.03 | 0.75 |
| Post-Mortem Interval[b] | 0.08 | 0.44 | 0.09 | 0.38 |
| Brain pH[b] | 0.16 | 0.11 | 0.07 | 0.49 |
| Brain Weight[b] | 0.03 | 0.74 | 0.04 | 0.68 |
| Storage Time[b] | 0.50 | <0.0001 | −0.33 | 0.0006 |
| Gender[c] | −0.03 | 0.98 | 0.11 | 0.39 |
| Hemisphere[c] | −0.003 | 0.62 | 0.02 | 0.81 |
| Smoking Status at Time of Death[c] | 0.004 | 0.96 | −0.04 | 0.60 |
| Lifetime Alcohol Use[c] | −0.01 | 0.34 | 0.06 | 0.50 |
| Lifetime Substance Abuse[c] | 0.07 | 0.89 | 0.12 | 0.21 |

[a]p-values from ANOVA.
[b]Pearson's product moment correlation shown for continuous variables.
[c]Kendall's rank correlation tau shown for ordinal variables.

The potential confounding effects of antipsychotic medication treatment on NOS1AP expression levels were also very important to examine, but since all of the patients with schizophrenia and none of the controls had been treated with such medications, the effects of treatment and diagnosis could not be separated by analyses that included these groups. Within the 35 individuals in the bipolar group, however, 18 individuals were on antipsychotic medication at the time of death, 11 individuals had never received antipsychotic medication, and six individuals were not on antipsychotic medication at time of death, but had been treated with these medications at some point in the past. NOS1AP levels were compared between antipsychotic-treated and untreated individuals with bipolar disorder. Neither a positive history of lifetime antipsychotic use nor antipsychotic use at time of death was significantly correlated with NOS1AP short-form (SEQ ID No. 3) expression within the bipolar group (Table 4). In contrast, expression of full-length NOS1AP (SEQ ID No. 1) was significantly correlated with treatment (Table 4), with a 40% decrease in mean expression in the patients ($n=24$) with bipolar disorder and a history of treatment with antipsychotics in the past or at time of death ($p=0.003$), and a 45% decrease in patients ($n=18$) receiving antipsychotics at time of death ($p=0.0007$), when compared to antipsychotic-untreated individuals ($n=11$) with bipolar disorder. An estimate of total lifetime antipsychotic medication was available for all but one individual in the bipolar and schizophrenia groups with a positive history of antipsychotic treatment ($n=58$). No significant correlations were found between levels of lifetime antipsychotic exposure and expression of either NOS1AP isoform (Table 4).

TABLE 4

Effect of Antipsychotic Treatment on NOS1AP Isoform Expression

| Variable | Group[a] | Full-Length Correlation[b] | p-value[c] | Short-Form Correlation[b] | p-value[c] |
|---|---|---|---|---|---|
| Any history of antipsychotic use[d] | BP | −0.38 | 0.0028 | −0.05 | 0.51 |
| Antipsychotic use at time of death[d] | BP | −0.52 | 0.0002 | −0.14 | 0.29 |
| Lifetime antipsychotic exposure[e] | BP | −0.19 | 0.26 | −0.05 | 0.79 |
| Lifetime antipsychotic exposure[e] | SCZ | 0.08 | 0.57 | −0.09 | 0.78 |
| Lifetime antipsychotic exposure[e] | BP + SCZ | 0.13 | 0.59 | −0.14 | 0.74 |

[a]BP = bipolar, SCZ = schizophrenia.
[b]Expression values for correlations controlled for length of storage.
[c]p-Values from ANOVA using storage time as a covariate.
[d]Correlation estimated with Kendall's rank correlation.
[e]Lifetime dose in fluphenazine milligram equivalents for patients with a positive history of neuroleptic exposure. Correlation estimated with Spearman's correlation; log of exposure used for ANOVA.

Figure 3:
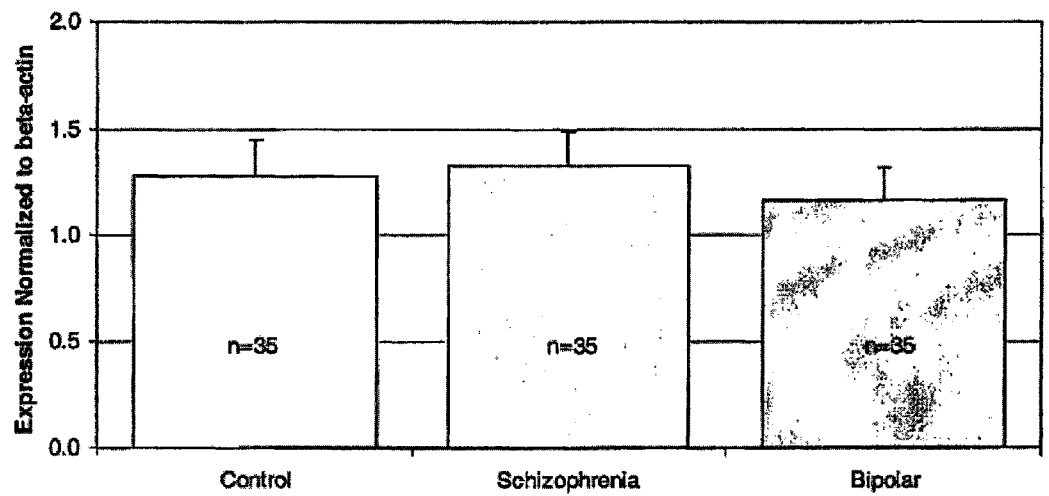
FIG. 3 is a graph showing the beta-actin normalized NOS1AP mRNA full-length expression by diagnosis. Expression levels are least squares means. Mean values per category are plotted with 95% confidence intervals. The number of subjects per sample is indicated within each bar. Level of expression does not differ significantly by diagnostic group. The mean (95% confidence interval lower bound, upper bound) for the control, schizophrenia, and bipolar groups are 1.28 (1.12, 1.45), 1.33 (1.17, 1.49), and 1.16 (0.99, 1.32), respectively

Overall, there was no significant difference in NOS1AP full-length mRNA expression across diagnostic categories (FIG. 3). Since treatment with antipsychotics may influence expression of the full-length isoform, expression of this transcript in antipsychotic-naive patients with bipolar disorder was examined. While mean NOS1AP full-length mRNA levels were increased by 24% in patients with bipolar disorder but no history of exposure to antipsychotic medication (n=11) as compared to normal controls, this increase did not reach statistical significance (p=0.11). Results were similar when comparing bipolar patients not receiving antipsychotic medication at time of death, regardless of past treatment history, (n=17) to normal controls, with a 18% increase in full-length NOS1AP levels (p=0.14).

Figure 4:
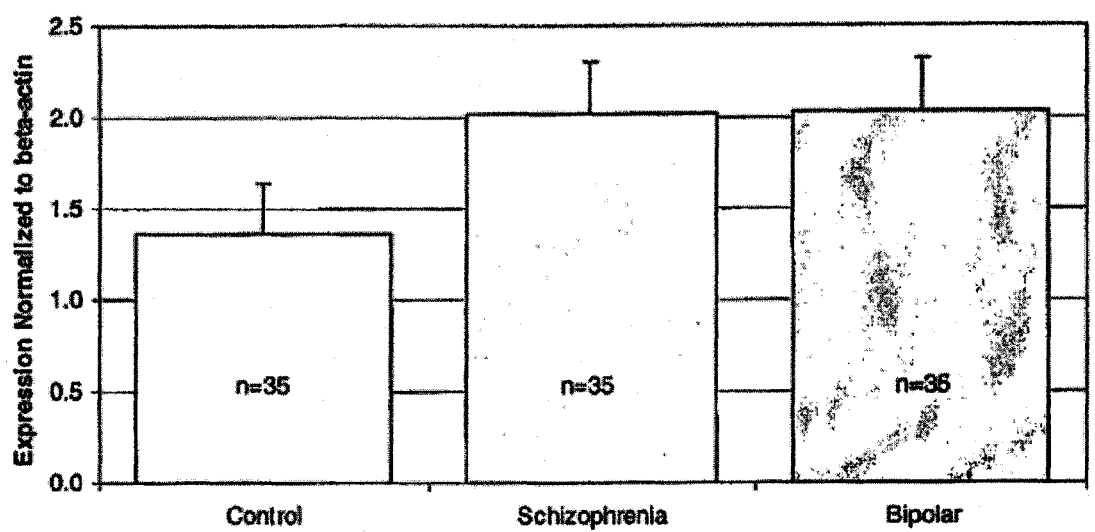
FIG. 4 is a graph showing the beta-actin normalized NOS1AP-S mRNA expression by diagnosis. Expression levels are least squares means. Mean values per category are plotted with 95% confidence intervals. The number of subjects per sample is indicated within each bar. Expression is significantly higher in subjects with schizophrenia (p=0.0013) and bipolar (p=0.0009) as compared to controls. The mean (95% confidence interval lower bound, upper bound) for the control, schizophrenia, and bipolar groups are 1.34 (1.05, 1.62), 2.02 (1.73, 2.30), and 2.05 (1.77, 2.34), respectively.

Mean NOS1AP-S mRNA levels were significantly increased by 48% in the schizophrenia group (p=0.0035) and 50% in the bipolar group (p=0.0002) as compared to the control group (FIG. 4). The schizophrenia and bipolar groups did not differ significantly from each other in NOS1AP-S expression (p=0.94). NOS1AP-S expression was significantly correlated with the age of onset in the schizophrenia group (Pearson's r=0.53, p=0.0008), but not in the bipolar group (r=−0.02, p=0.92). This significance (or lack thereof) is unchanged when age of death is included as a covariate. The majority of samples were from individuals of European decent (97%), with one African American individual with bipolar disorder, one Native American individual with bipolar disorder, and one Hispanic individual with schizophrenia. None of these individuals exhibited extreme values for expression of either NOS1AP isoform, and re-analysis with these patients excluded did not change which comparisons reached statistical significance.

III. Analysis of NOS1AP Isoform Expression by Genotype

Figure 5:
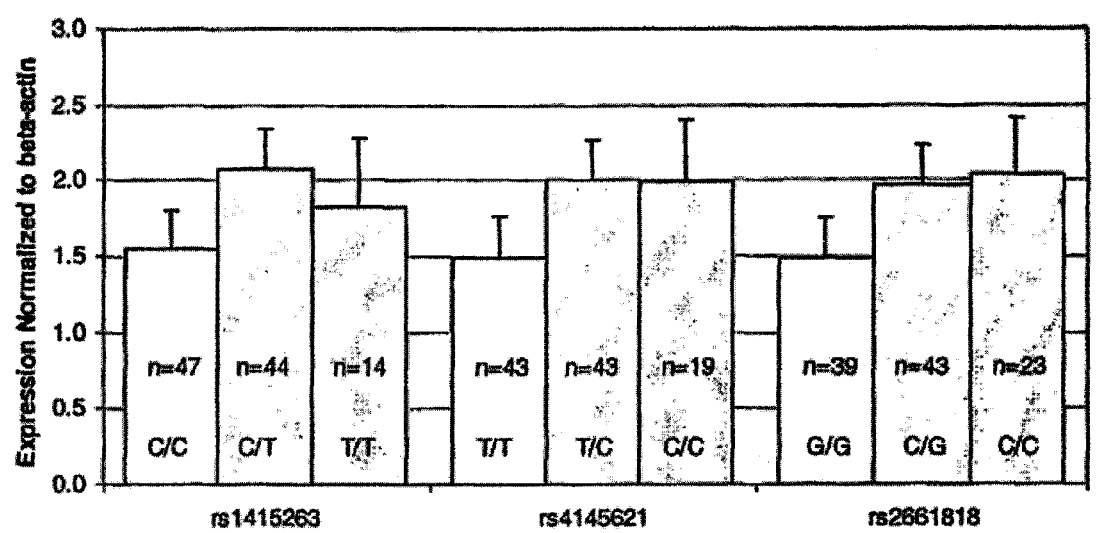
FIG. 5 is a graph showing the beta-actin normalized NOS1AP-S expression by genotype. Expression levels are least squares means. Individuals from all three diagnostic classifications are included, grouped only by genotype. Mean values per genotype for each SNP are plotted with 95% confidence intervals. The number of subjects per genotype is indicated within each bar. SNP alleles are given for forward strand sequence. All three SNPs exhibit significantly (p<0.05) different levels of NOS1AP expression by genotype, with a dominant effect. Higher levels of NOS1AP are seen in subjects with one or two copies of alleles previously identified as associated with schizophrenia (T for rs1415263, C for rs4145621, and C for rs2661818). The mean (95% confidence interval lower bound, upper bound) for the three genotypes for each SNP are for rs1415263, 1.54 (1.29, 1.80) for CC, 2.07 (1.81, 2.34) for CT, and 1.83 (1.36, 2.29) for TT; for rs4145621, 1.51 (1.25, 1.78) for TT, 2.01 (1.74, 2.27) for TC, and 2.01 (1.61, 2.41) for CC; and for rs2661818, 1.49 (1.21, 1.76) for GG, 1.96 (1.70, 2.23) for CG, and 2.04 (1.68, 2.41) for CC.

All individuals were genotyped at rs1415263, rs4145621, and rs2661818, the three SNPs within NOS1AP that were previously identified as being in significant linkage disequilibrium with schizophrenia (Brzustowicz et al. 2004). For each SNP, individuals with one or two copies of the previously identified associated allele were observed to have higher group mean NOS1AP-S (SEQ ID No. 3) expression than the group of individuals homozygous for the unassociated allele (FIG. 5). All three SNPs individually showed significant differences among means for NOS1AP-S expression (rs1415263, p=0.019; rs4145621, p=0.022; rs2661818, p=0.019), while none showed significantly different means for the full-length NOS1AP (SEQ ID No. 1) expression (rs1415263, p=0.67; rs4145621, p=0.52; rs2661818, p=0.50). Genotypes with one or two copies of the associated alleles had higher mean NOS1AP-S expression (rs1415263, 30%; rs4145621, 32%; rs2661818, 34%). None of the SNPs showed significant expression differences between individuals heterozygous or homozygous for the associated allele. Given that the prior demonstrated correlation between NOS1AP full-length expression and antipsychotic treatment could represent a medication treatment effect, the correlation analysis between NOS1AP full-length expression and genotype was rerun using only individuals not receiving antipsychotic medications at time of death (35 controls and 17 individuals with bipolar disorder). Again, there were no significant differences in mean NOS1AP full-length expression among genotypes for any of these SNPs (rs1415263, p=0.41; rs4145621, p=0.82; rs2661818, p=0.58).

Discussion

The screening of a human fetal total brain cDNA library resulted in the identification of two isoforms of NOS1AP mRNA corresponding to two forms of NOS1AP protein. The present screen used only primers from exon 10, so it would not be possible detect isoforms lacking this portion of the gene. One of the two identified transcripts encompasses ten exons and encodes a 501 amino acid protein (SEQ ID No. 2) containing two known functional domains, an amino-terminal phosphotyrosine-binding domain and a carboxyl-terminal PDZ-binding domain. This full-length form corresponds to transcripts previously identified in the rat and human (Jaffrey S R et al. 1998; Seki N et al. 1997). The second transcript contains the last two exons of NOS1AP and is predicted to produce a short form of the protein (SEQ ID No. 4), 211 amino acids long and containing the PDZ-binding domain. Prior work has demonstrated that the caboxy-terminal 125 amino acids of the full-length protein are sufficient to bind the PDZ-domain of nNOS and interfere with the binding between nNOS and PSD93 or PSD95. In addition to the ability of NOS1AP to bind to nNOS, the caboxy-terminal 125 amino acids also appear to be able to directly bind to the second PDZ domain of PSD95, the normal site of nNOS binding to PSD95. As the first 180 amino acids of NOS1AP have been previously demonstrated to contain the domain needed to bind to the amino-terminal targets Dexras1 and Synapsin, it would seem that only the full-length form of NOS1AP would be able to serve as an adaptor protein between nNOS and these targets. A physiological role of the short form would likely be limited to the competitive inhibition of binding of other ligands to the PDZ domains of nNOS and PSD93 or PSD95.

There are significant obstacles to the study of gene expression in the human brain. Obtaining high-quality postmortem samples suitable for RNA extraction is difficult and labor-intensive. Obtaining appropriate matched control groups is also a challenge. While it may be possible to collect samples with relative consistency across some variables, such as PMI or brain pH, many factors that may potentially affect gene expression, such as treatment history and substance use, are beyond the control of investigators. The rate of collection of individuals with too many clinical restrictions (e.g., treatment-naive individuals with schizophrenia and no history of substance abuse, alcohol use, or smoking) would be too slow to produce a useful number of samples. Added to these clinical variables is likely etiological heterogeneity, with only a subset of affected individuals expected to harbor a primary causative mutation in any given gene. All of these factors may lessen the chance that significant differences in gene expression can be demonstrated using a particular sample.

The present expression studies are conducted using the Stanley Array Collection, as this collection contains samples from more individuals than other postmortem collections, and the samples were collected in a standardized fashion with an emphasis on obtaining high-quality RNA for expression studies. Limitations of this collection include the facts that protein samples were not available for parallel analysis, and that only one brain region, the DLPFC, was available for study. However, this brain region has long been hypothesized to be involved in schizophrenia, implicated by evidence from neuropsychological, neuroimaging, histopathological, and neurochemical studies.

The results suggest that mRNA expression of NOS1AP-S (SEQ ID No. 3) is significantly ($p<0.005$) increased in patients with either schizophrenia or bipolar disorder. NOS1AP-S protein (SEQ ID No. 4) is capable of disrupting the binding of nNOS to PSD95 through competitive inhibition and removing nNOS from the NMDA receptor complex, thereby decoupling NO generation from NMDA receptor activation. This could produce a picture consistent with the NMDA receptor hypofunction hypothesis of schizophrenia. Based on the present data, expression of short-form mRNA does not appear sensitive to treatment with antipsychotic medication. Full-length NOS1AP mRNA expression, in contrast, appears to be highly influenced by treatment with antipsychotic medication, at least in bipolar disorder. Pre- and post-exposure expression studies in animals may be helpful in determining if the relationship between antipsychotic treatment and decreased NOS1AP mRNA expression is causal. While no significant group differences in expression levels between patients with schizophrenia or bipolar disorder and normal controls was found, it is possible that this is due to the normalization of full-length NOS1AP mRNA expression by antipsychotic treatment. Additional expression studies in individuals with schizophrenia not receiving antipsychotic medication would be of great interest to assess this possibility.

The Stanley Array Collection consists of samples collected from several locations within the United States, and therefore represents a sample that is independent from the Canadian familial schizophrenia collection used previously in Brzustowicz et al. 2004. Nonetheless, there is significant evidence for association between affection phenotypes and the same alleles at three different SNPs in both samples. Consistent with the hypothesis that NOS1AP short form overexpression is associated with schizophrenia, the alleles observed associated with schizophrenia in the Canadian sample are significantly ($p<0.05$) associated with higher short form expression in the Stanley Array Collection.

The three SNPs investigated span nearly 98 kb and are located in introns 2 and 3 of NOS1AP, the most proximal being 70 kb upstream from the short-form transcription start site. Although there is evidence for linkage disequilibrium (LD) spanning large regions within NOS1AP, it is unlikely that these SNPs are in tight disequilibrium with polymorphisms in the short-form basal promoter. Prior work on this gene revealed that the three SNPs used in this study are in significant ($p<0.0001$) linkage disequilibrium with each other (rs1415263 and rs4145621, $D'=0.748$; rs1415263 and rs2661818, $D'=0.801$; rs4145621 and rs2661818, $D'=0.491$), while being in much weaker LD ($D'$ values ranging from 0.074 to 0.432) with SNPs located in intron 8 (rs7521206) and exon 9 (rs348624). More probable is that the SNPs used in the present study are in LD with a mutation in an enhancer region that is located at some distance upstream of the short-form transcript. Enhancers can regulate gene expression from distances of up to 1 Mb, and mutations in enhancer sequences have been shown to be responsible for a number of human diseases.

Additional studies are needed to further examine the level of NOS1AP protein among individuals with different psychiatric diagnoses, in both the DLPFC and other regions of the brain. The implication that NOS1AP may influence susceptibility of neuropsychiatric disorders through disruption of NMDA receptor functioning adds to the list of candidate genes that may act at this receptor system, including Neuregulin 1, D-amino acid oxidase and G72, Dysbindin, and PPP3CC. Additional work on the interaction of these different candidates may also further the understanding of the genetic component of susceptibility of neuropsychiatric disorders, such as schizophrenia and bipolar disorders.

Example II

In this example, the effects of overexpression of NOS1AP protein in neurons were examined using primary cultures of hippocampal neurons. cDNAs encoding the full-length NOS1AP protein (SEQ ID No. 2) and NOS1AP-S protein (SEQ ID No. 4) were separately cloned into expression vectors and transfected along with GFP (to elucidate neuronal morphology) at 10 days in vitro, a time when dendrite outgrowth and branching is rapidly occurring. It was hypothesized that NOS1AP may affect dendrite number since the NMDA receptor has been implicated in playing a role in regulating dendrite number, and overexpression of NOS1AP is thought to disrupt NMDA receptor signaling. Two days after transfection, the neurons were fixed, and dedrites were counted as described in Akum et al., *Nat Neurosci* 2004 February; 7(2):145-52, 2004 and Chen et al., *Mol Biol Cell* 2005 November; 16(11):5103-14. As shown in FIG. 6, the neurons transfected with NOS1AP-L isoform exhibit significantly ($p<0.05$) decreasing primary and secondary dendrites by approximately 40% when compared to controls transfected only with GFP. Since dendrite morphology is crucial to interneuronal communication, the increases in short-form NOS1AP protein seen in patients suffering from neuropsychiatric disorders, such as schizophrenia and bipolar disorders, may result in altered dendrite morphology in the hippocampus, and perhaps the DLPFC.

The effects of treatment of transfected neurons with APV, a competitive antagonist of NMDA receptors has been tested. Treatment of control cells transfected with GFP alone with a dosage of APV expected to fully block NMDA receptor function results in an approximately 25% drop in primary dendrite branching, indicating the importance of the NMDA system in this developmental process. While transfection with NOS1AP-L results in an approximately 50% decrease in primary dendrite branching, treatment of NOS1AP-L transfected neurons with APV does not result in any additional decrease in dendrite branching. While not wishing to be bound by any theory, this data suggests that overexpression of NOS1AP-L may be acting through an additional mechanism to reduce dendrite branching, as the level of reduction is significantly greater than that obtained by NMDA receptor blockade alone. NOS1AP-L is also important in the targeting of nNOS to the pre-synaptic membrane through interactions with Synapsin, so there may be multiple mechanisms of action, at both the pre- and post-synaptic membrane, that modulate the effect of NOS1AP on dendrite branching. FIG. 7 shows the promoter sequence of the NOS1AP-L gene. FIG. 8 provides the nucleic and amino acid sequences of NOS1AP-L and NOS1AP-S respectively.

Example III

During neuronal development, two processes take place before proper communication between neurons can be created: 1) targeting of synaptic proteins to correct pre- and postsynaptic sites and 2) establishment of stereotypical dendritic arborization patterns for specific neurons (Vetter et al., 2001; Schaefer et al., 2003). On the other hand, various neurological disorders are associated with disturbed receptor signaling and dendritic branching. For example, dendritic field size is smaller in layer V pyramidal cortical neurons in schizophrenic patients (Black et al., 2004) and truncation of the protein encoded by Disrupted-in-Schizophrenia-1 results in decreased neurite outgrowth in PC12 cells (Miyoshi et al., 2003; Ozeki et al., 2003). Decreased dendrite number and/or branching is also seen in a number of developmental disorders such as autism, Rett Syndrome, Down Syndrome and unclassified mental retardation (Zoghbi, 2003). Despite significant progress in the field, understanding of the intracellular mechanisms regulating dendritic branching remains fragmentary. The mechanisms by which the branching of dendrites are regulated needs to be elucidated. It has previously found that synaptic proteins, such as PSD-95, and their partners, such as cypin and snapin, regulate dendrite patterning before and during synapse stabilization (Akum et al., 2004; Chen et al., 2005; Charych et al., 2006). Recently, study of the roles played by NOS1AP on the regulation of dendritic patterns has been performed.

NOS1AP was first identified as a binding protein of neuronal nitric oxide synthase (nNOS) (Jaffrey et al., 1998). It competes with PSD-95 for nNOS binding and reduces PSD-95 signaling. Later studies revealed that there are two alternately expressed forms of NOS1AP. Transcription of all NOS1AP exons gives rise to a cDNA that can be translated to a 501 amino acid (aa) protein, designated as NOS1AP-Long. When only the last two exons were transcribed, a protein of 125 aa designated as NOS1AP-Short is produced. Except for the first 12 aa, NOS1AP-Short is the same as the C-terminus of NOS1AP-Long.

The structure and binding partners of NOS1AP-Long have been studied preliminarily. NOS1AP-Long protein contains two distinct domains, a C-terminal PDZ-binding domain, responsible for the interaction of NOS1AP with nNOS, and a phosphotyrosine binding (PTB) domain. Two studies revealed that the PTB domain of NOS1AP-Long binds to DexRas1 and synapsin (Fang et al., 2000; Jaffrey et al., 2002). DexRas1 activity was found to be regulated by nNOS nitrosylation. Subsequent studies showed that DexRas1 regulate iron metabolization. NOS1AP mRNA levels (Xu et al., 2005) and protein levels are elevated in patients with schizophrenia and bipolar disorder. The mechanism by which alterations in NOS1AP expression affects brain function is not yet known. Efforts have been made to address how NOS1AP levels regulate hippocampal neuronal function. This form, termed NOS1AP-Long for long form, is decreased by 40% in mRNA expression in subjects treated with antipsychotics relative to untreated patients. (Xu et al., 2005). The short form of NOS1AP mRNA, noted as NOS1AP-Short, is unaffected by antipsychotic drugs. NOS1AP-Long also contains a glutamine repeat typically present in proteins that are involved in neurodegenerative diseases.

Another feature of the present invention relates to the discovery that amino acid residues 186-312 of the carboxyl-terminal PDZ ligand of neuronal nitric oxide synthase (NOS1AP or NOS1AP) are responsible for NOS1AP's activity in decreasing dendrite and spine number in cultured hippocampal neurons, and that such activity is mediated by carboxypeptidase E (CPE). Overexpression of NOS1AP-long results in such decreases and is associated with schizophrenia (Xu et al., 2005). Accordingly, applicants' discovery of this region of NOS1AP can be utilized to find agents useful for the treatment of schizophrenia and other adverse conditions. According to the present invention, this region of NOS1AP can be used to screen drugs for inhibitors of this activity of NOS1AP, and particularly those that block the association of NOS1AP and CPE. Moreover, this region may also be used to find partner proteins that can then be assessed to determine if they are susceptibility loci for schizophrenia and thus may be used as biomarkers.

Materials and Methods

I. Hippocampal Neuron Cultures:

Neuronal cultures were prepared from hippocampi of rat embryos at 18 day gestation as described previously (Firestein et al., 1999). The hippocampi were dissociated, and cells were plated on poly-D-lysine-coated glass coverslips (12 mm diameter) at a density of 1800 cells/mm$^2$. Cultures were maintained in Neurobasal media supplemented with B27, penicillin, streptomycin, and L-glutamine. Cells were grown for 5-21 days in vitro (DIV) and used for specific experiments as indicated below.

II. Transfection of Cultured Cells:

cDNAs encoding human NOS1AP and several mutant forms of human NOS1AP were cloned into the expression vector pCMV6-XL4 (Origene). These plasmids are referred to directly as NOS1AP (or NOS1AP mutants) without indicating the vector. In addition, the fusion proteins GFP-NOS1AP-L (GFP-NPL), GFP-NOS1AP-S (GFP-NPS), and GFP-NOS1AP-181-307 (GFP-NOS1AP-M, GFP-NPM) were constructed in the pEGFP-C1 vector (Clontech Inc.). Cultured hippocampal neurons were transfected with the appropriate cDNA constructs as follows. Neurons were transfected on DIV 10 using EFFECTENE following the manufacturer's protocol (Qiagen Inc.). Neurons were transfected on DIV 2, 5, or 7 using LIPOFECTAMINE-2000 following the manufacturer's protocol (Invitrogen Inc.). The Amaxa Nucleofector kit for Rat Neurons (Amaxa Inc., kit VPG-1003) was used to transfect newly dissected neurons (DIV 0) before plating.

III. Antibodies and Reagents:

Two different polyclonal NOS1AP antibodies from Santa Cruz Inc. were used. Rabbit anti-NOS1AP (R-300) recognizes the C terminus aa 304-501 of NOS1AP-L; goat anti-NOS1AP (S-17) recognizes the N-terminus of NOS1AP-L. Rat anti-green fluorescent protein (GFP) was a kind gift from Dr. Shu-Chan Hsu of Rutgers University. Mouse anti-microtubule-associated protein 2 (MAP2) was purchased from BD PharMingen (San Diego, Calif.). Cyanine (Cy) 2-, Cy3- and Cy5-conjugated secondary antibodies were purchased from Jackson ImmunoResearch (West Grove, Pa.). Monoclonal anti-HA antibody and nNOS inhibitor N(ω)-nitro-L-arginine-methyl ester (L-NAME) were purchased from Sigma (St. Louis, Mo.).

IV. Immunocytochemistry:

Neurons were fixed in 4% paraformaldehyde in PBS for 30 minutes and then incubated in blocking solution (PBS containing 0.1% Triton X-100, 2% normal goat serum, and 0.02% sodium azide) for 1 h. All antibodies used were diluted in blocking solution. For GFP and NOS1AP or GFP and HA double immunostaining, dilutions of 1:1000 for rat anti-GFP and 1:500 for rabbit anti-NOS1AP, or 1:500 for goat anti-NOS1AP, or 1:1000 for mouse anti-HA (CRP Inc.) were used. All incubations with primary antibodies were performed at 4° C. overnight. Neurons were then washed with PBS three times. Secondary antibody consisted of a 1:250 dilution of Cy2-conjugated anti-rat IgG and Cy3-conjugated donkey anti-rabbit, anti-goat, or anti-mouse IgG. Coverslips were then mounted onto frosted glass microscope slides using Fluoromount G (Southern Biotechnology, Birmingham, Ala.). Labeled cells were visualized by immunofluorescence on an Olympus Optical (Tokyo, Japan) IX50 microscope with a Cooke Sensicam charge-coupled device cooled camera fluorescence imaging system and Image Pro software (Media Cybernetics, Silver Spring, Md.).

V. Assessment of Dendrite Number:

Primary and secondary dendrite numbers were counted by hand with the experimenter blinded to the conditions (Akum et al., 2004). Pictures of neurons were contrast-enhanced and the numbers of primary and secondary dendrites for each neuron were recorded. Primary dendrites are processes longer than 3 μm and originate directly from the cell body. Secondary dendrites are branches of primary dendrites. n values indicate the number of neurons counted.

VI. RNA Interference:

Small interference RNA (siRNA) targeting the CPE transcript (5'-GTTTGTCCGTGACCTTCAA-3; SEQ ID NO: 23) and an unrelated sequence as a negative control (5'-GCTTGGTTACTCCTGGATT-3'; SEQ ID NO: 24) were designed. The siRNA was converted to shRNA and its DNA was subcloned into the pSuper-GFP vector (Oligoengine, Seattle, Wash.) according to the manufacturer's instructions. Oligonucleotides were synthesized and purchased from Bio-Synthesis (Lewisville, Tex.).

VII. Quantification of Fluorescence Intensity:

Hippocampal neurons were prepared, cultured, and transfected as above. The neurons were immunostained with monoclonal antibody against CPE (1:1000). Fluorescence intensities of CPE were measured using Image Pro software. Cell bodies for each neuron were traced, and intensities were measured as average pixel intensity within the selected region. Fluorescence was visualized using a 20× objective. To quantitate the fluorescence levels of tagged proteins, images of neurons were captured by CCD as above using a constant gain and exposure time for all samples. Images were corrected for coverslip fluorescence by subtracting a background image generated using an 11×11 erosion filter. The experimenter was blinded to the condition when taking images and assaying fluorescence intensities.

VIII. Immunoprecipitation and Western Blot:

One rat brain was homogenized in 10 ml of TEEN (25 mM Tris, 1 mM EGTA, 1 mM EDTA, 100 mM NaCl, pH 7.4)+1 mM PMSF. Triton X-100 was added to a final concentration of 1%, and proteins were extracted for 1 h at 4° C. The extract was centrifuged at 10,000×g to remove insoluble material. The supernatant was diluted 5-fold with TEEN and incubated with rabbit anti-NOS1AP (R-300) at 4° C. overnight. Protein A beads were added for one hour of incubation. Beads were washed three times with TEEN containing 0.2% Triton X-100. Immuno-precipitated proteins were eluted with protein loading buffer and subjected to Western blot analysis.

SDS-PAGE gels were used for Western blots. After electrophoresis, resolved proteins were transferred to PVDF membranes (Immobilon-P; Fisher Scientific). The blots were probed with the indicated antibodies. After blocking with 3% bovine serum albumin (BSA) in PBS, membranes were incubated with primary antibodies, monoclonal anti-CPE (1:500) or monoclonal anti-actin (Sigma-Aldrich, 1:2,000), overnight at 4° C. After washing, horseradish peroxidase linked secondary anti-mouse IgG was applied at 1:2,000 for one hour at RT. Immunoreactive bands were visualized using the enhanced chemiluminescence (ECL) system (Amersham Biosci.).

Results

I. NOS1AP-Long Reduced Dendrite Branching

Figure 9:
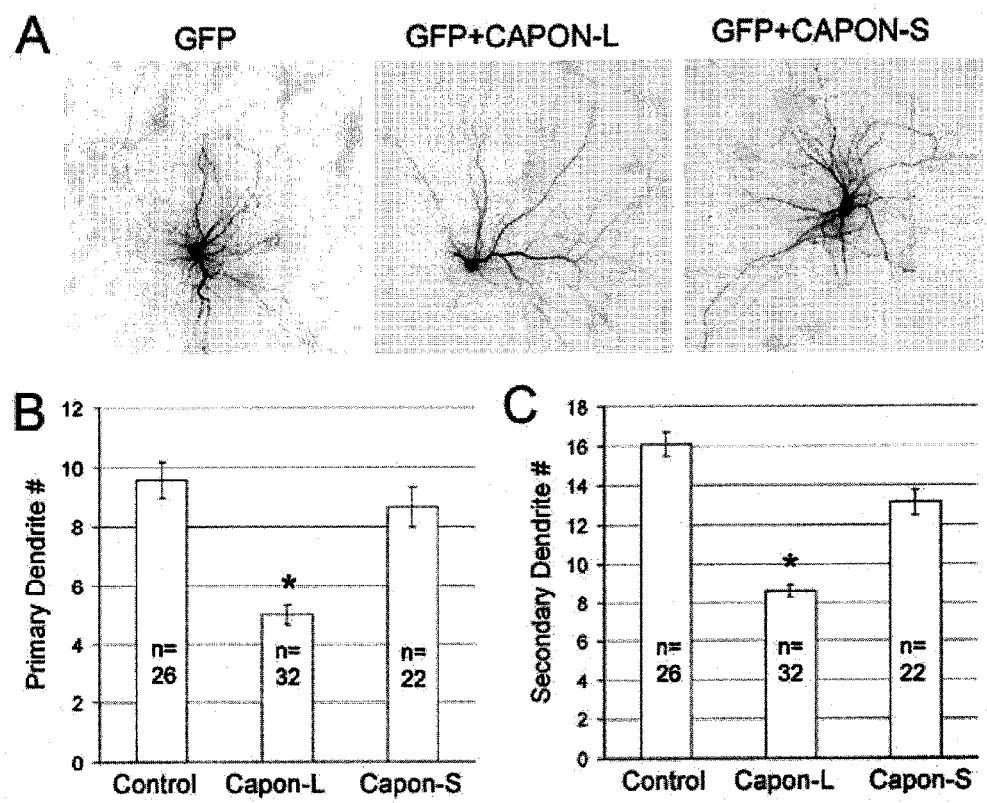
FIG. 9 shows that NOS1AP-Long reduces dendrite branching. DIV 10 hippocampal neurons were transfected with DNA constructs encoding GFP, or GFP with NOS1AP-Long (NOS1AP-L) or GFP with NOS1AP-Short (NOS1AP-S). Cells were fixed on DIV 12 and stained with GFP and NOS1AP antibodies. The numbers of primary and secondary branches of the transfected neurons were analyzed. (A), sample pictures illustrating GFP-positive neurons. (B and C), statistical analysis demonstrating the numbers of primary and secondary branches in the three groups. NOS1AP-Long was much more effective at reducing dendritic branching than NOS1AP-Short. * Significantly different from control, p<0.01.

Cultured hippocampal neurons were transfected with vectors containing GFP, or co-transfected with GFP and NOS1AP-Long, or GFP and NOS1AP-Short on Day in Vitro (DIV) 10. After 48 hours, cells were fixed and stained with GFP and NOS1AP antibodies. Primary and secondary dendrite numbers of GFP-positive neurons were analyzed. In the case of double-transfection, only neurons transfected with both GFP and NOS1AP (L or S) were monitored. While NOS1AP-Long reduced primary and secondary dendrite numbers, NOS1AP-Short did not significantly alter branching (FIG. 9). Since NOS1AP is a ligand for nNOS, next examinations of whether nNOS is regulating NOS1AP actions were performed.

Figure 10:
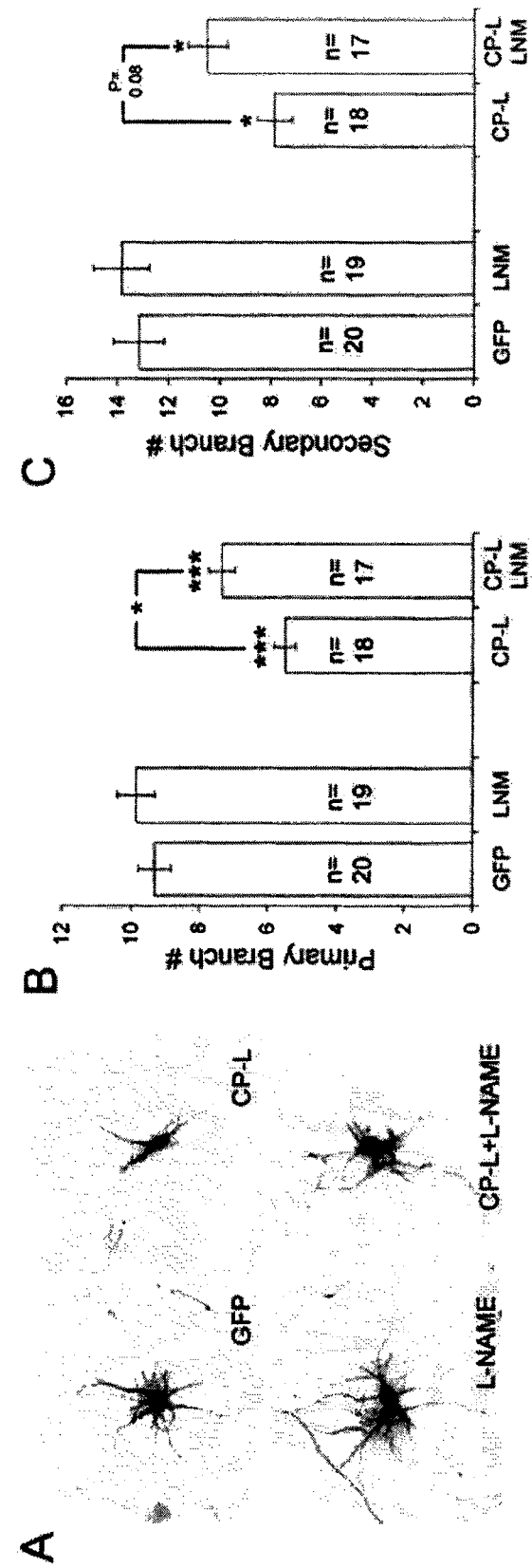
FIG. 10 shows that treatment of neurons with L-NAME (LNM) to inhibit nNOS activity reduced NOS1AP-Long (CP-L) activity. DIV 10 hippocampal neurons were transfected with GFP or GFP with NOS1AP-Long. Right after transfection, L-NAME was added to 500 nM. Cells were fixed on DIV 12 and stained. (A), Illustration of GFP stained neurons. (B and C), Number of primary and secondary dendrites were monitored. ***, significantly different from GFP, p<0.001. *, significantly different, p<0.05.

II. Blocking nNOS Activity Attenuated the Effects of NOS1AP on Dendrite Branching To manipulate the activity of nNOS, the inhibitor, L-NAME was used. Application of L-NAME right after transfection resulted in partial reduction of NOS1AP-Long effects. Although blocking nNOS with 500 μM of L-NAME did not fully inhibit the effects of NOS1AP-Long, it did elicit a significant difference in NOS1AP-Long induced primary dendrite number (FIG. 10B). The difference between secondary dendrite number of cells treated with NOS1AP-Long alone and with L-NAME was smaller, yet the distinction was still clear (FIG. 10C).

III. NOS1AP Mutants and their Effects on Dendrite Branching

NOS1AP binds to other proteins as well as nNOS. The PTB domain of NOS1AP has been shown to bind to DexRas1 and synapsin. Therefore, NOS1AP mutants were constructed to explore the possible involvement of these proteins in the effect of NOS1AP on dendritic branching. Five constructs encoding mutant forms of NOS1AP-Long were generated (FIG. 11A). NOS1AP HA-20-185 is the PTB domain tagged with HA. NOS1AP-ΔPDZ lacks the PDZ binding domain. NOS1AP 186-C lacks the N terminus and the PTB domain. NOS1AP 186-ΔPDZ lacks both PTB and PDZ binding domains. NOS1AP HA-186-312 is the HA tagged section of NOS1AP-Long without PTB domain and the C-terminus section that is identical with NOS1AP-Short.

Figure 11:
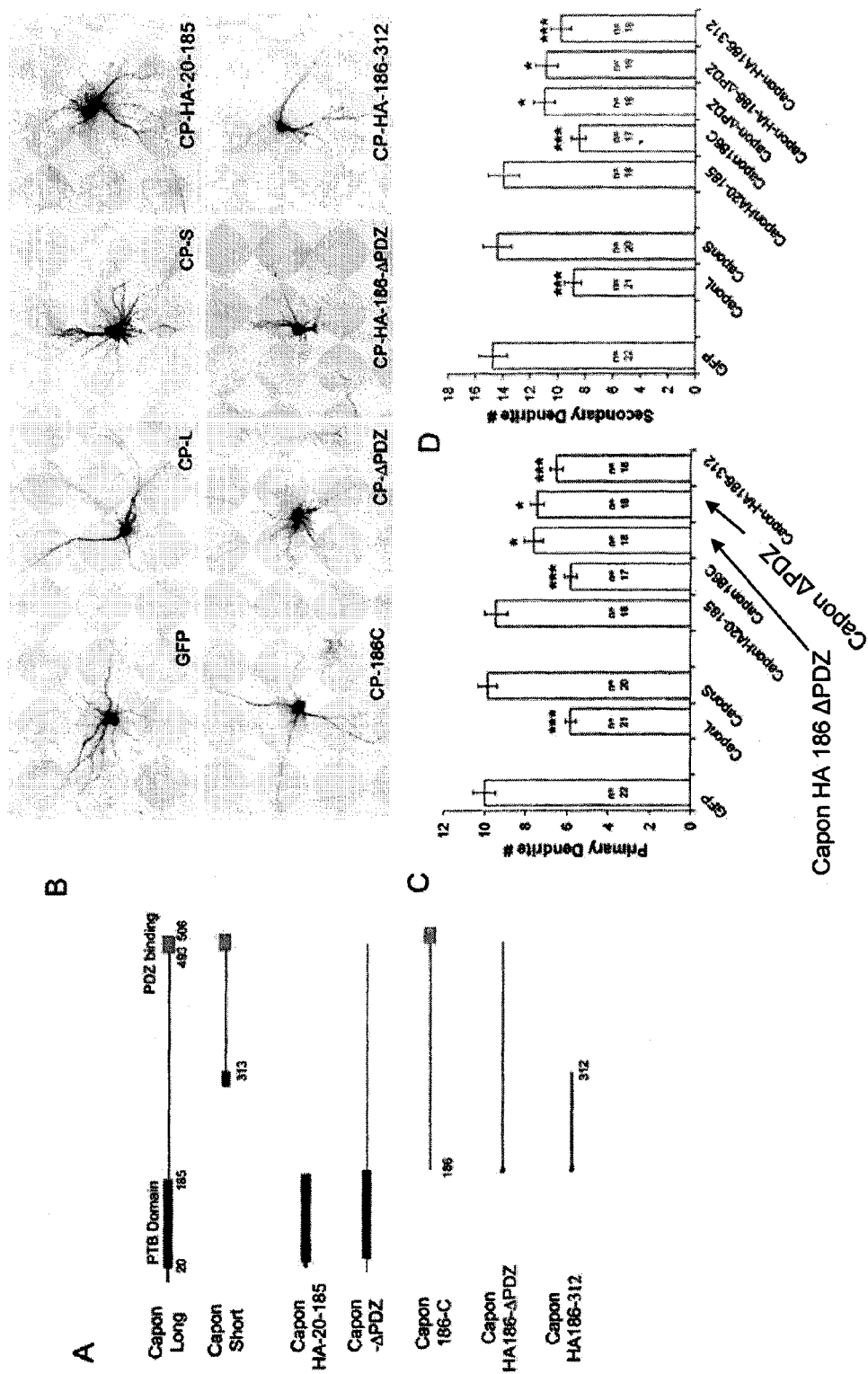
FIG. 11 shows mutant forms of NOS1AP and their effects on dendrite branching. (A) Illustration of NOS1AP-Long (CP-L), NOS1AP-Short (CP-S), and five mutant forms (i.e. subregions) of NOS1AP. (B), DIV 10 hippocampal neurons were transfected with GFP and the different forms of NOS1AP. Cells were fixed at DIV 12 and stained. GFP staining of hippocampal neurons expressing NOS1AP mutants were illustrated here. (C and D), Primary and secondary branches were monitored. ***, significantly different from GFP, p<0.001. *, significantly different from GFP, p<0.05.

Cultured hippocampal neurons were transfected with the NOS1AP mutant constructs and the cells were fixed and stained at DIV 12. NOS1AP HA-20-185 had no effect on dendrite numbers, indicating that neither DexRas1 nor synapsin is involved in mediating NOS1AP's activity on dendritic branching. In contrast, all mutants containing the middle portion of NOS1AP, amino acids 186-312, elicited a significant reduction of primary and secondary dendrite numbers (FIG. 11). Accordingly, neither the PDZ-binding domain nor the PTB domain is needed, and it is the middle region of NOS1AP, amino acids 186-312, which mediates the reduction in dendrite number.

IV. Identification of NOS1AP Binding Partners

Yeast-2-Hybrid techniques were adopted to explore those proteins which bind to the middle region (amino acids 186-312) of NOS1AP-Long (also known as NOS1AP-L). NOS1AP-186-312 was cloned into a bait vector and a cDNA library derived from rodent brain was screened. Several reactive proteins were identified. Among these was carboxypeptidase E (CPE), a member of the carboxypeptidase family that processes various proteins in the CNS. CPE has also been found to work as a sorting receptor for prohormones (Cool and Loh, 1998). A mutation of CPE in mice results in a reduction of CPE activity, lower expression, and early-onset obesity (Naggert et al., 1995).

The binding of NOS1AP and CPE was confirmed with biochemical studies. As shown in FIG. 12A, CPE was co-immunoprecipitated with NOS1AP from adult rat brain lysate, verifying that the two proteins are in the same complex. Moreover, a fusion protein containing GST and NOS1AP-186-312 pull down CPE protein, compared to minimal pull-down by NOS1AP-Short, confirming that the middle part of NOS1AP is responsible for this binding activity (FIG. 12B). These results, together with the Yeast-2-Hybrid data, suggest that NOS1AP binds directly to CPE.

V. Roles Played by CPE in Effects of NOS1AP to Reduce Dendrite Branching

Figure 13:
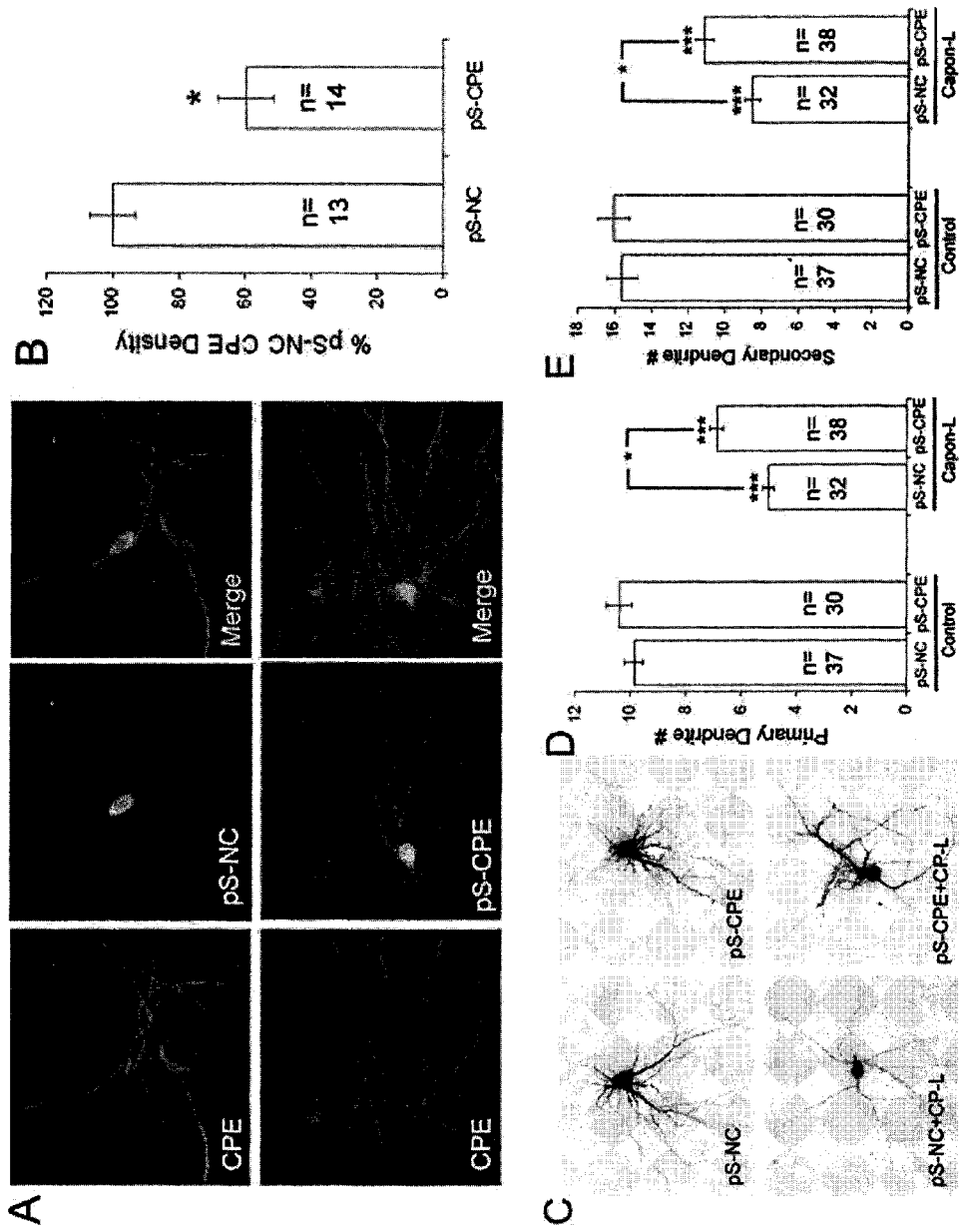
FIG. 13 shows knockdown of CPE reduced NOS1AP-Long (CP-L) effects. DIV 10 hippocampal neurons were transfected with pSuper-GFP-Negative-Control (pS-NC) or pSuper-GFP-CPE-Knock-Down (pS-CPE) along with a construct for NOS1AP-Long. Cells were fixed and stained on DIV 12. (A), Illustration of double-staining of GFP (Green) and CPE (Red). (B), CPE intensity in cells transfected with pS-NC or pS-CPE was monitored and compared. (C), Illustration of GFP staining of transfected neurons. (D and E), Number of primary and secondary dendrites was monitored. ***, significantly different from GFP, p<0.001. *, significantly different, p<0.05.

To determine whether CPE participates in NOS1AP's activity in reducing dendritic branching, CPE shRNA (pS-CPE) to knock down CPE protein levels were constructed. pS-CPE and an unrelated shRNA (negative-control, pS-NC) were cloned into the pSUPER-GFP RNAi vector. DIV 10 hippocampal neurons were transfected with pS-CPE and pS-NC. Cells were fixed 48 hours later and stained for CPE. By comparing the CPE intensity in neurons transfected with pS-CPE and pS-NC (FIG. 13A), it was determined that CPE shRNA attenuated CPE protein expression (FIG. 13B). The construction of pS-CPE provides us the tool to determine whether CPE is involved in NOS1AP actions. Co-expression of pS-CPE with CPL attenuated the effects of CPL to reduce primary and secondary dendrites (FIGS. 13C, D), indicating that CPE is mediating the activity of NOS1AP.

Example IV

Figure 14:
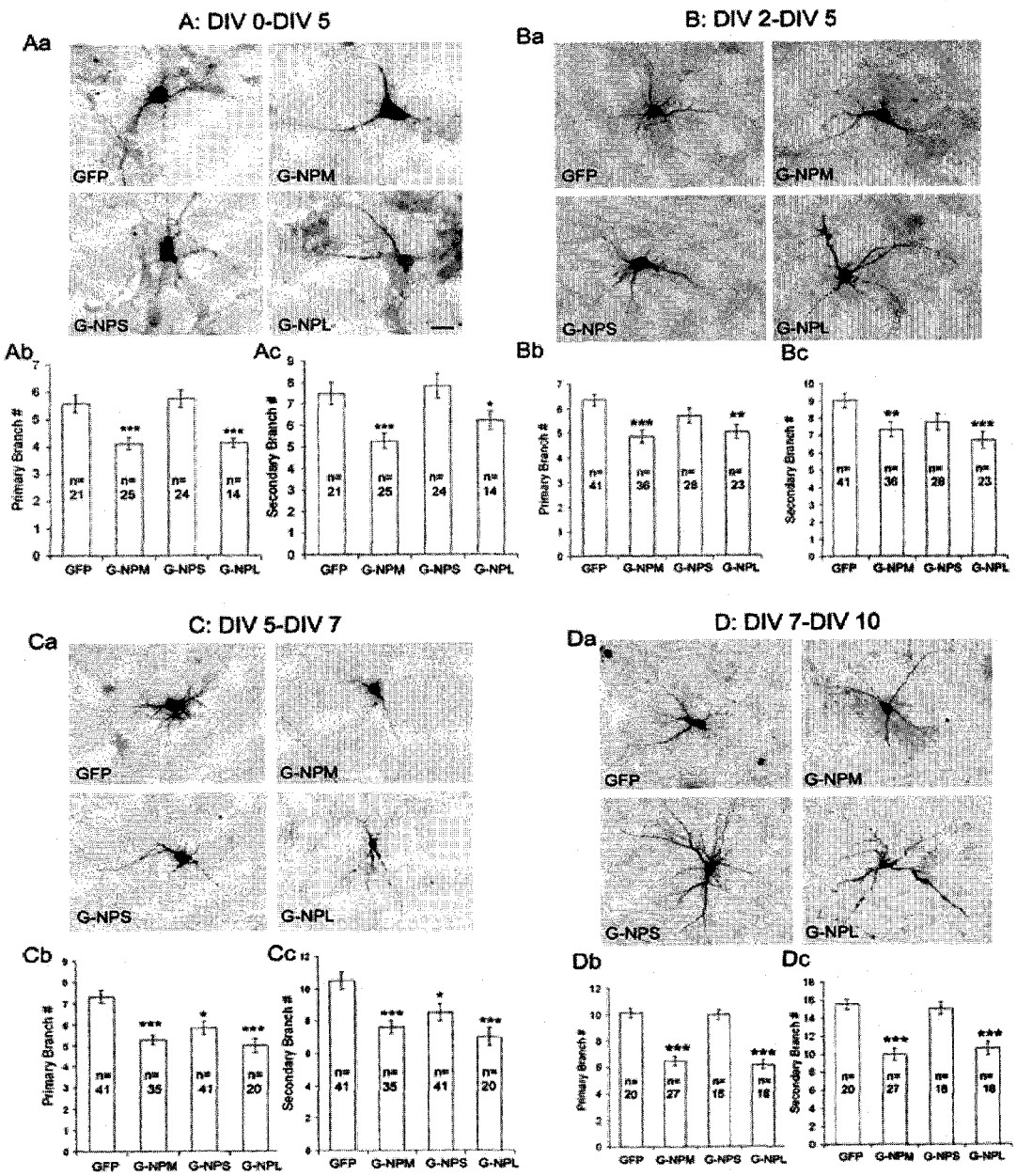
FIG. 14 shows that overexpression of NOS1AP alters dendrite number in young hippocampal neuron cultures. Cells were transfected with cDNA encoding GFP, GFP-NOS1AP-L (G-NPL), GFP-NOS1AP-S (G-NPS), or GFP-NOS1AP-M ("M", mutant form of NOS1AP-L, amino acids 181-307); (G-CPM) at the indicated dates (A, DIV 0; B, DIV 2; C, DIV 5, D, DIV 7). Neurons were fixed and immunostained for dendrite counting at DIV 5 (A), DIV 5 (B), DIV 7 (C) or DIV 10 (D). (Aa, Ba, Ca, Da), GFP images of representative neurons. (Ab, Bb, Cb, Db, Ac, Bc, Cc, Dc), Average number of primary and secondary dendrites in transfected neurons. Scale bar, 10 mm. *, p<0.05, , p<0.01, *, p<0.001, by nonparametric ANOVA followed by Dunn's analysis comparing G-NPL, G-NPS, and G-NPM groups with GFP.

I. The Effects of NOS1AP Isoforms on Reduction of Dendrite Branching in Earlier Cultures The time points examined (DIV 10-12) for the effects of NOS1AP were chosen since it is during this time period that active branching occurs (Charych et al., 2006). To assess whether NOS1AP affects the initiation or maintenance of dendrites, the effects of overexpression of NOS1AP were examined in younger hippocampal neuron cultures. To explore whether the initial branching of dendrites is regulated by NOS1AP, freshly dissected hippocampi were dissociated and transfected with plasmids encoding GFP or GFP-tagged NOS1AP-L, NOS1AP-M, or NOS1AP-S using the Amaxa Nucleofector kit for rat neurons. Neurons were fixed on DIV 5 and dendrite branching was examined. Over-expression of GFP-NOS1AP-L and GFP-NOS1AP-M reduced branching while GFP-NOS1AP-S had no significant effect (FIG. 14A). To further examine the roles played by NOS1AP in dendrite branching during neuron development, cultured hippocampal neurons were transfected on DIV2, DIV 5, and DIV 7 with GFP, GFP-NOS1AP-L, GFP-NOS1AP-S, and GFP-NOS1AP-M constructs and fixed on DIV 5, DIV 7, and DIV 10, respectively. Examination of dendrite morphology revealed a similar level of reduction resulting from overexpression of GFP-NOS1AP-L and GFP-NOS1AP-M (FIGS. 14B, C, D). These results indicate that NOS1AP-L can alter the dendritic development of hippocampal neurons at almost any early stage. In contrast, overexpression of GFP-NOS1AP-S reduced branching from DIV 5 to DIV 7 (FIG. 14B), suggesting a possible role of NOS1AP-S in earlier stages of neuronal development. Thus, the actions of NOS1AP-L on neurons at different developmental stages suggests that NOS1AP-L alters both dendrite initiation and maintenance, while the limited effect of NOSAP1-S at a single developmental time point suggests that NOS1AP-S may only influence a specific stage of dendrite outgrowth and branching.

II. Overexpression of NOS1AP Reduces Protrusion Formation

Figure 15:
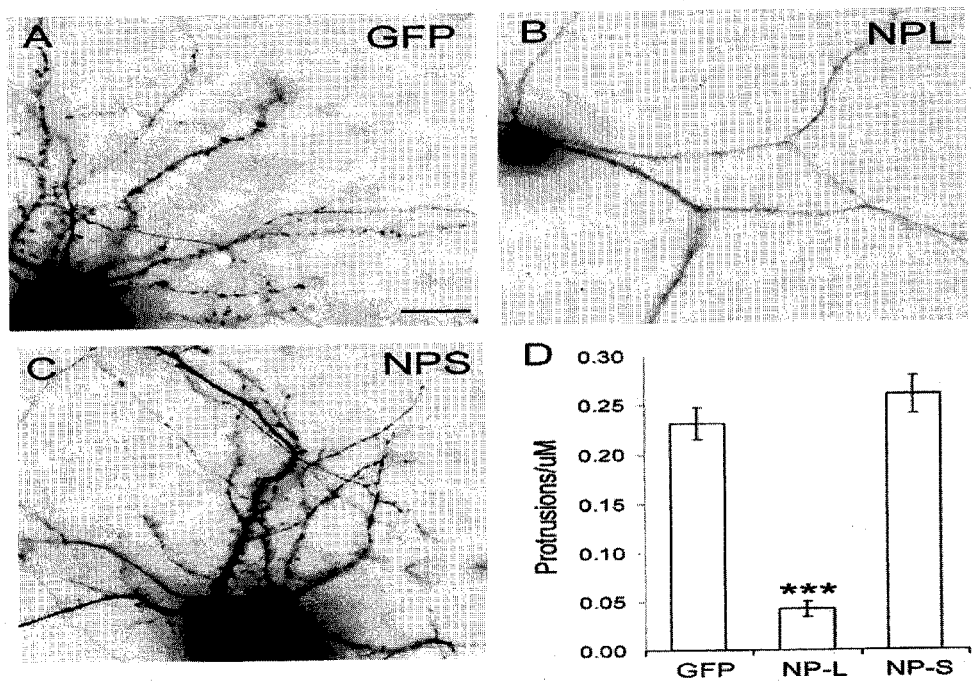
FIG. 15 shows that overexpression of NOS1AP-L reduces protrusion formation in mature hippocampal neurons. Hippocampal neurons were transfected on DIV 10 with cDNA constructs encoding GFP, GFP and NOS1AP-L (NP-L), or GFP and NOS1AP-S(NP-S). Neurons were fixed and immunostained for analysis of protrusion number at DIV 21. (A, B, C), GFP images of representative neurons. Scale bar, 5 mm. (D), The average number of protrusions per μm dendrite length for each condition. ***, p<0.001, by nonparametric ANOVA followed by Dunn's analysis comparing co-transfected groups with GFP.

NOS1AP-L influences dendrite branching in hippocampal neurons during dendrite initiation, outgrowth, and active branching (DIV 0 to DIV 12). Thus, it is also of interest to examine whether further maturation and differentiation of dendrites can be altered by NOS1AP. Hippocampal cultures were transfected on DIV 10 with cDNAs encoding GFP, GFP plus NOS1AP-L, or GFP plus NOS1AP-S. Cells were fixed at DIV 21 and the formation of dendritic spines and filopodia, crucial structures for the establishment of synapses, was monitored. As indicated in FIG. 15, the average number of protrusions per μm dendrite length was significantly reduced by presence of NOS1AP-L. However, as in the case for branching, NOS1AP-S does not alter protrusion number. Thus, the data suggest that NOS1AP may act to regulate dendritic spine development.

III. An shRNA Against NOS1AP Coding Sequence (Position 398) Knocks Down NOS1AP by Approximately 45%

Figure 16:
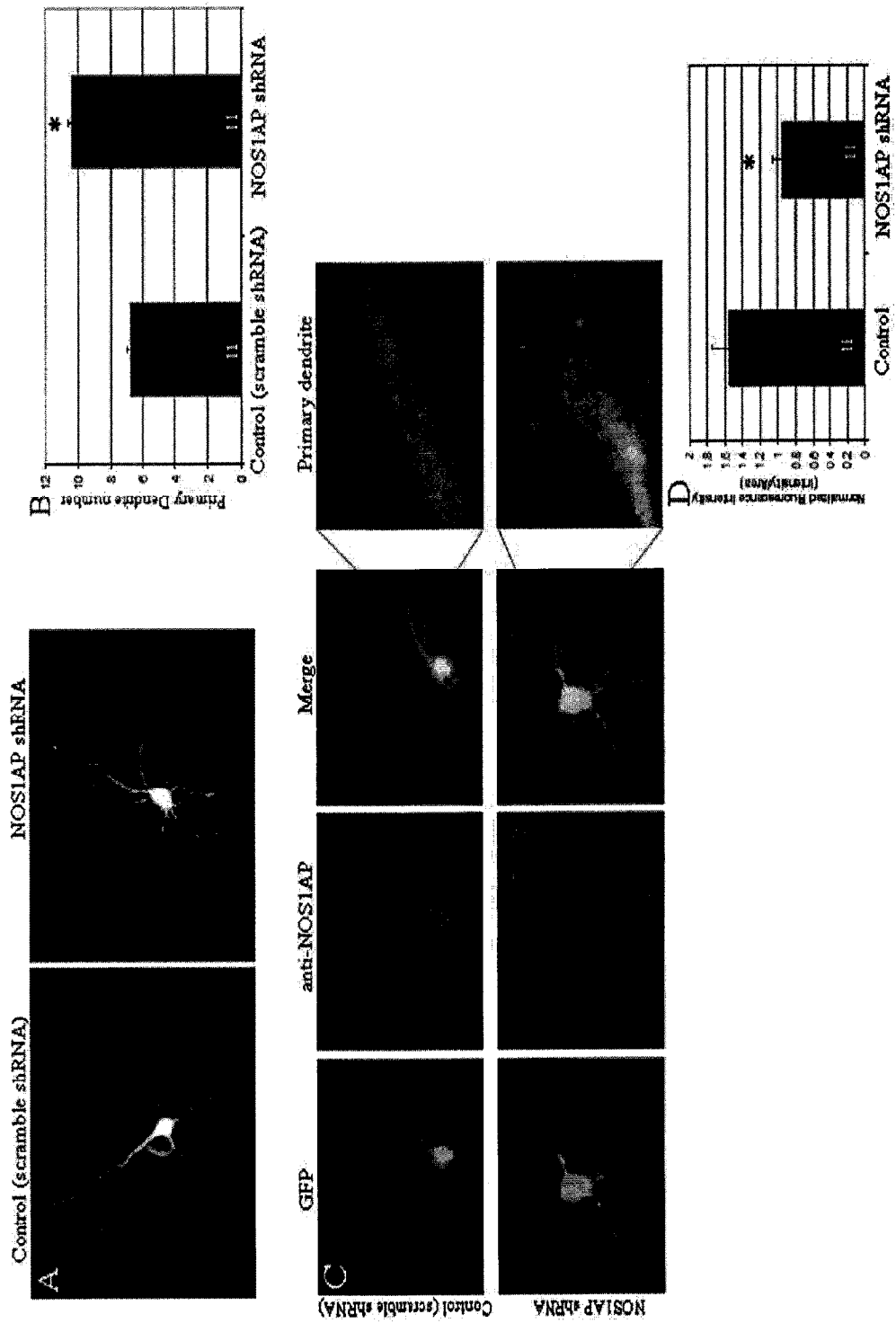
FIG. 16 shows that expression of an shRNA against NOS1AP-L results in a 40% decrease in NOS1AP expression and a 67% increase in primary dendrite number over 48 hours. A) Hippocampal neurons were transfected with either pSUPER-scramble shRNA or pSUPER-NOS1AP shRNA at DIV10 and fixed at DIV12. B) Quantification of primary dendrites shown. C) Hippocampal neurons transfected with the same vectors as in A at DIV10 and fixed and immunostained for NOS1AP at DIV12. Zoomed inset indicates a representative region of primary dendrite showing corresponding fluorescence intensities of anti-NOS1AP. D) Quantification of NOS1AP levels in primary dendrite regions, as represented by normalized (total intensity/area) fluorescence intensity levels. *p<0.05 by Student's t-test.

A shRNA was constructed to knock down NOS1AP-L with the sequence 5'-GCAATATCTTCAGATGCAA-3' (SEQ ID NO: 22; position 790 of NM_138922) using the pSUPER vector. The resulting siRNA is specific to the long isoform of NOS1AP. As shown in FIGS. 16C and D, expression of this shRNA knocks down endogenous NOS1AP protein by 40% after 48 hours (DIV 10-12). Importantly, primary dendrite number increases by 67% when NOS1AP is knocked down (FIGS. 16A and B). These results, taken with other findings 1) confirm that NOS1AP-L negatively regulates dendrite branching and 2) that knockdown of NOS1AP is feasible and that the level of knock down is sufficient to promote biological effects. Furthermore, the fact that knocking down NOS1AP results in an effect on dendrite number that is opposite to overexpression suggests that overexpression of NOS1AP-L or NOS1AP-M does not act in a dominant negative manner.

IV. Overexpression of NOS1AP in Utero Results in Altered Cortical Radial Migration Since the NMDA receptor signaling pathway has been reported to regulate cortical radial migration, it was hypothesized that NOS1AP plays a role in this developmental process. To test this hypothesis in utero electroporation (IUE) experiments were performed. Rat embryos at 16 days gestation were electroporated with cDNA encoding GFP or GFP-NOS1AP-M. These studies utilized NOS1AP-M due to the fact that it decreases dendrite number in the same manner as does NOS1AP-L. Constructs were allowed to express for 48 hours, and embryos were sacrificed at E18. Cortices from these rats were sectioned at 16 μm and imaged using epifluorescence microscopy. As shown in FIG. 17, overexpression of NOS1AP-M inhibits migration of cortical cells after 48 hours of expression.

V. eEF2 and Hippocalcin-Like 1 Co-Immunoprecipitate with NOS1AP

Figure 12:
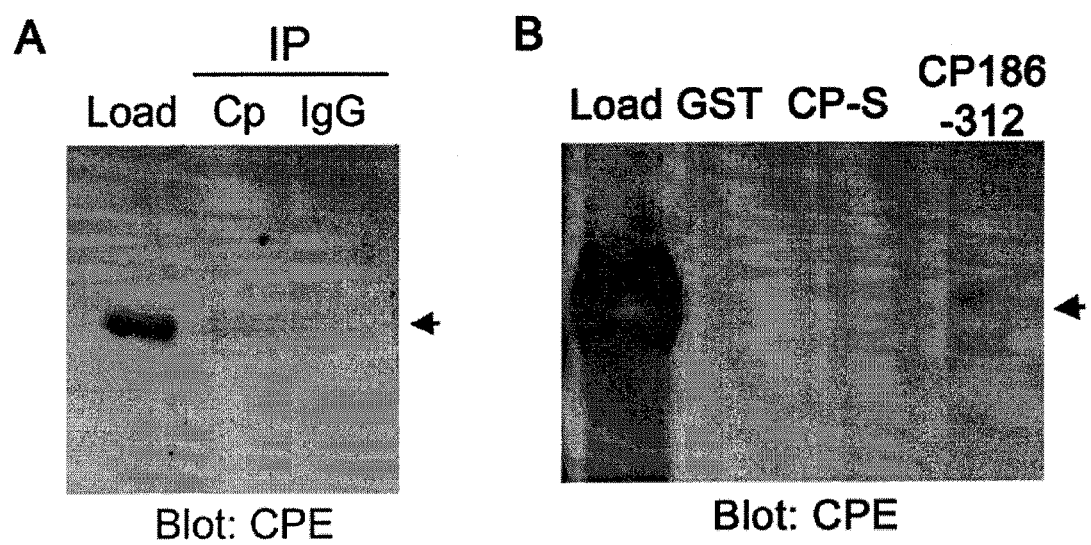
FIG. 12 shows that binding of CPE to NOS1AP was confirmed with immunoprecipitation and GST pull-down studies. (A), rat brain lysate was incubated with NOS1AP (CP) antibody and protein-A sepharose. The eluate was separated using polyacrylamide gel electrophoresis, transferred to PVDF membrane, and blotted with CPE antibody. (B), rat brain lysate was screened with GST or GST-fusion proteins. The eluted proteins were separated using polyacrylamide gel electrophoresis, transferred to PVDF membrane, and blotted with CPE antibody.
Figure 18:
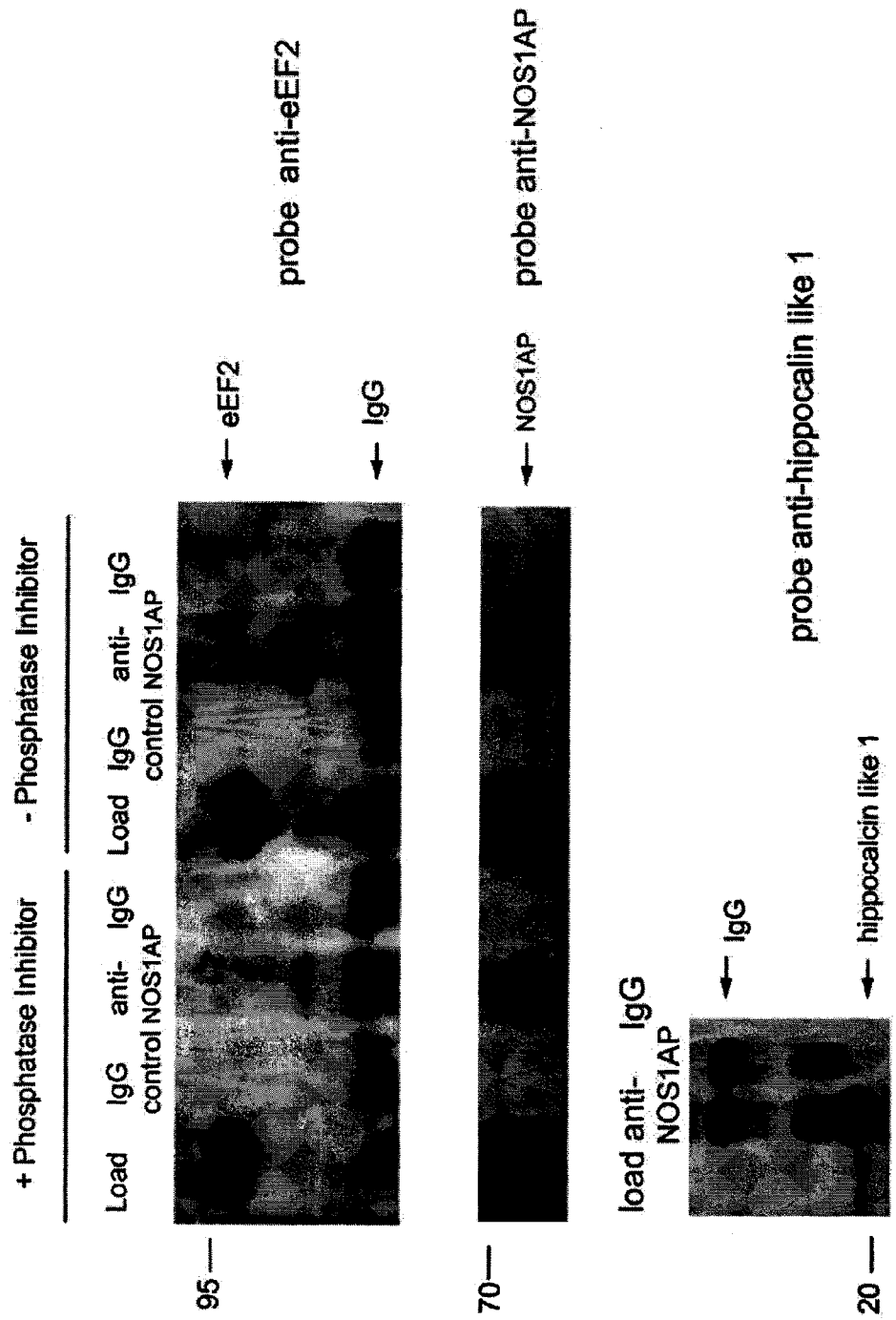
FIG. 18 shows eEF2 and hippocalcin-like 1 co-immunoprecipitate (co-IP) with NOS1AP. NOS1AP was immunoprecipitated from rat brain extract, and precipitates were subjected to SDS-PAGE and Western blotting. The top panel shows that eEF2 co-IPs with NOS1AP and that this interaction is enhanced by the absence of a phosphatase inhibitor cocktail. The middle panel shows that NOS1AP is immunoprecitated by the NOS1AP antibody. The bottom panel shows that hippocalcin-like 1 co-IPs with NOS1AP.

Nine putative interactors for NOS1AP aa 181-307 have been identified. The interactions between NOS1AP and each one of carboxypeptidase E (CPE), eukaryotic elongation factor 2 (eEF2), and hippocalcin-like 1 have been confirmed (FIGS. 12 and 18). NOS1AP binds directly to eEF2 and hippocalcin-like 1, and these proteins co-immunoprecipitate with NOS1AP from rat brain extracts (FIG. 18).

VI. BETA-ACTIN IS IN A COMPLEX WITH NOS1AP

Figure 19:
FIG. 19 shows that actin is found in a complex with NOS1AP. Rat brain extract was incubated with a polyclonal antibody to NOS1AP (CP) or rabbit IgG (negative control). Immunoprecipitates were run on SDS-PAGE, transferred to PDVF, and the blot was probed for actin.

Beta actin is known to interact with gamma actin, which maps to chromosome 17 under a significant schizophrenia linkage peak. Co-immunoprecipitation experiments demonstrate that beta actin is in a complex with NOS1AP (FIG. 19).

Figure 20:
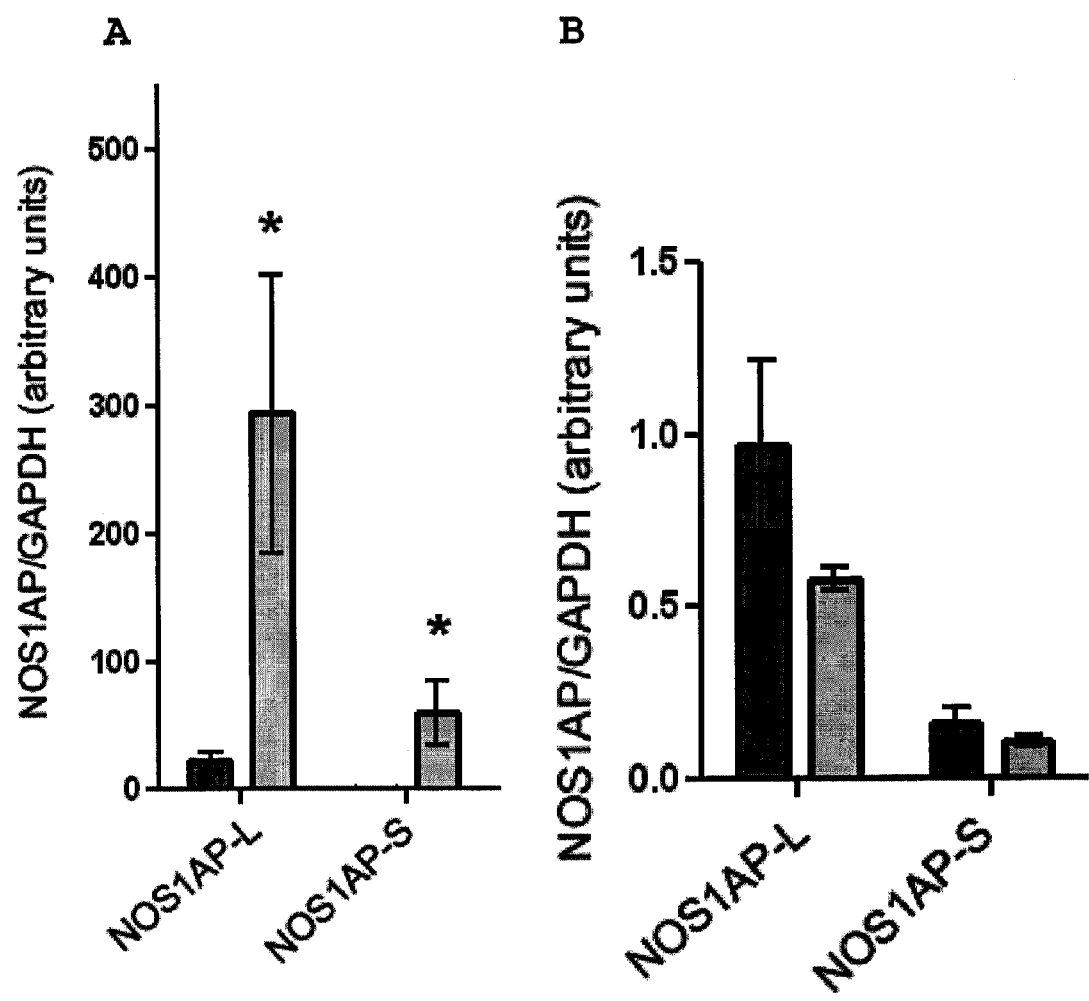
FIG. 20 shows expression of NOS1AP is increased in BA46 of schizophrenic patients in panel A. The graph represents the results of a Western blot of lysates from postmortem brains from control and schizophrenic patients. Dark bars represent the amount of NOS1AP in controls, and the light bars represent the amount of NOS1AP in schizophrenic patients. Panel B is a negative control from the olfactory lobe of the brain which is not involved in schizophrenia, and NOS1AP is not increased.

VII. Expression of NOS1AP (i.e., NOS1AP) is Increased in Brodmann's Area 46 (DLPFC) in Schizophrenic Patients FIG. 20 is a graph results from a western blot of brain extracts from Brodmann's Area 46 (PAGE followed by western blot probed with NOS1AP antibodies and GAPDH (control)). The results shown were normalized to GAPDH, and a student's t-test was used to assess data. FIG. 20A demonstrates that both NOS1AP long and short forms are increased in schizophrenic patients, while FIG. 20B represents data from the olfactory lobe of the brain which is not involved in schizophrenia, and neither form of NOS1AP is increased compared to the control.

In summary, the results presented herein provide the means to identify agents having efficacy for the treatment of schizophrenia, and identify patients having an increased risk for developing schizophrenia and other neurological disorders. The co-immunoprecipitation data also provide new targets which can be therapeutically modulated to beneficially impact the schizophrenic phenotype.

REFERENCES

AbdelMalik P, Husted J, Chow E W, Bassett A S (2003) Childhood head injury and expression of schizophrenia in multiply affected families. Arch Gen Psychiatry 60:231-236.

Akum B F, Chen M, Gunderson S I, Riefler G M, Scerri-Hansen M M, Firestein B L (2004) Cypin regulates dendrite patterning in hippocampal neurons by promoting microtubule assembly. Nat Neurosci 7:145-152.

Black J E, Kodish I M, Grossman A W, Klintsova A Y, Orlovskaya D, Vostrikov V, Uranova N, Greenough W T (2004) Pathology of layer V pyramidal neurons in the prefrontal cortex of patients with schizophrenia. Am J Psychiatry 161:742-744.

Bassett A S, Chow E W, Waterworth D M, Brzustowicz L (2001) Genetic insights into schizophrenia. Can J Psychiatry 46:131-137.

Brenman J E, Chao D S, Gee S H, McGee A W, Craven S E, Santillano D R, Wu Z, Huang F, Xia H, Peters M F, Froehner S C, Bredt D S (1996a) Interaction of nitric oxide synthase with the postsynaptic density protein PSD-95 and alpha1-syntrophin mediated by PDZ domains. Cell 84:757-767.

Brenman J E, Christopherson K S, Craven S E, McGee A W, Bredt D S (1996b) Cloning and characterization of postsynaptic density 93, a nitric oxide synthase interacting protein. J Neurosci 16:7407-7415.

Brzustowicz L M, Hayter J E, Hodgkinson K A, Chow E W, Bassett A S (2002) Fine mapping of the schizophrenia susceptibility locus on chromosome 1q22. Hum Hered 54:199-209.

Brzustowicz L M, Hodgkinson K A, Chow E W, Honer W G, Bassett A S (2000) Location of a major susceptibility locus for familial schizophrenia on chromosome 1q21-q22. Science 288:678-682.

Brzustowicz L M, Simone J, Mohseni P, Hayter J E, Hodgkinson K A, Chow E W, Bassett A S (2004) Linkage disequilibrium mapping of schizophrenia susceptibility to the CAPON region of chromosome 1q22. Am J Hum Genet 74:1057-1063. Epub 2004 April 1052.

Bunney W E, Bunney B G (2000) Evidence for a compromised dorsolateral prefrontal cortical parallel circuit in schizophrenia. Brain Res Brain Res Rev 31:138-146.

Charych E I, Akum B F, Goldberg J S, Jornsten R J, Rongo C, Zheng J Q, Firestein B L (2006) Activity-independent regulation of dendrite patterning by postsynaptic density protein PSD-95. J Neurosci 26:10164-10176.

Chen M, Lucas K G, Akum B F, Balasingam G, Stawicki T M, Provost J M, Riefler G M, Jornsten R J, Firestein B L (2005) A novel role for snapin in dendrite patterning: interaction with cypin. Mol Biol Cell 16:5103-5114.

Chumakov I, Blumenfeld M, Guerassimenko O, Cavarec L, Palicio M, Abderrahim H, Bougueleret L, et al. (2002) Genetic and physiological data implicating the new human gene G72 and the gene for D-amino acid oxidase in schizophrenia. PNAS:182412499.

Cool D R, Loh Y P (1998) Carboxypeptidase E is a sorting receptor for prohormones: binding and kinetic studies. Mol Cell Endocrinol 139:7-13.

Coyle J T, Tsai G, Goff D (2003) Converging evidence of NMDA receptor hypofunction in the pathophysiology of schizophrenia. Ann N Y Acad Sci 1003:318-327.

Fang M, Jaffrey S R, Sawa A, Ye K, Luo X, Snyder S H (2000) Dexras1: a G protein specifically coupled to neuronal nitric oxide synthase via CAPON. Neuron 28:183-193.

Gerber D J, Hall D, Miyakawa T, Demars S, Gogos J A, Karayiorgou M, Tonegawa S (2003) Evidence for association of schizophrenia with genetic variation in the 8p21.3 gene, PPP3CC, encoding the calcineurin gamma subunit. Proc Natl Acad Sci USA 100:8993-8998. Epub 2003 July 8908.

Gurling H M, Kalsi G, Brynjolfson J, Sigmundsson T, Sherrington R, Mankoo B S, Read T, Murphy P, Blaveri E, McQuillin A, Petursson H, Curtis D (2001) Genomewide Genetic Linkage Analysis Confirms the Presence of Susceptibility Loci for Schizophrenia, on Chromosomes 1q32.2, 5q33.2, and 8p21-22 and Provides Support for Linkage to Schizophrenia, on Chromosomes 11q23.3-24 and 20q12.1-11.23. Am J Hum Genet 68:661-673.

Harrison P J, Owen M J (2003) Genes for schizophrenia? Recent findings and their pathophysiological implications. Lancet 361:417-419.

Hwu H G, Liu C M, Fann C S, Ou-Yang W C, Lee S F (2003) Linkage of schizophrenia with chromosome 1q loci in Taiwanese families. Mol Psychiatry 8:445-452.

Jaffrey S R, Benfenati F, Snowman A M, Czernik A J, Snyder S H (2002) Neuronal nitric-oxide synthase localization mediated by a ternary complex with synapsin and CAPON. Proc Natl Acad Sci USA 99:3199-3204.

Jaffrey S R, Snowman A M, Eliasson M J, Cohen N A, Snyder S H (1998) CAPON: a protein associated with neuronal nitric oxide synthase that regulates its interactions with PSD95. Neuron 20:115-124.

Kikuno R, Nagase T, Nakayama M, Koga H, Okazaki N, Nakajima D, Ohara O (2004) HUGE: a database for human KIAA proteins, a 2004 update integrating HUGEppi and ROUGE. Nucleic Acids Res 32:D502-504.

Lewis C M, Levinson D F, Wise L H, DeLisi L E, Straub R E, Hovatta I, Williams N M, et al. (2003) Genome Scan Meta-Analysis of Schizophrenia and Bipolar Disorder, Part II: Schizophrenia. Am J Hum Genet 73:34-48.

McGuffin P, Asherson P, Owen M, Farmer A (1994) The strength of the genetic effect. Is there room for an environmental influence in the etiology of schizophrenia? Br J Psychiatry 164:593-599.

Miyoshi K, Honda A, Baba K, Taniguchi M, Oono K, Fujita T, Kuroda S, Katayama T, Tohyama M (2003) Disrupted-In-Schizophrenia 1, a candidate gene for schizophrenia, participates in neurite outgrowth. Mol Psychiatry 8:685-694.

Naggert J K, Fricker L D, Varlamov O, Nishina P M, Rouille Y, Steiner D F, Carroll R J, Paigen B J, Leiter E H (1995) Hyperproinsulinaemia in obese fat/fat mice associated with a carboxypeptidase E mutation which reduces enzyme activity. Nat Genet 10:135-142.

Ohara O, Nagase T, Ishikawa K, Nakajima D, Ohira M, Seki N, Nomura N (1997) Construction and characterization of human brain cDNA libraries suitable for analysis of cDNA clones encoding relatively large proteins. DNA Res 4:53-59.

Ozeki Y, Tomoda T, Kleiderlein J, Kamiya A, Bord L, Fujii K, Okawa M, Yamada N, Hatten M E, Snyder S H, Ross C A, Sawa A (2003) Disrupted-in-Schizophrenia-1 (DISC-1): mutant truncation prevents binding to NudE-like (NUDEL) and inhibits neurite outgrowth. Proc Natl Acad Sci USA 100:289-294.

Rosa A, Fañanás L, Cuesta M J, Peralta V, Sham P (2002) 1q21-q22 locus is associated with susceptibility to the reality-distortion syndrome of schizophrenia spectrum disorders. American Journal of Medical Genetics 114:516-518.

Schaefer A T, Larkum M E, Sakmann B, Roth A (2003) Coincidence detection in pyramidal neurons is tuned by their dendritic branching pattern. J Neurophysiol 89:3143-3154.

Seki N, Ohira M, Nagase T, Ishikawa K, Miyajima N, Nakajima D, Nomura N, Ohara O (1997) Characterization of cDNA clones in size-fractionated cDNA libraries from human brain. DNA Res 4:345-349.

Shaw S H, Kelly M, Smith A B, Shields G, Hopkins P J, Loftus J, Laval S H, Vita A, De Hert M, Cardon L R, Crow T J, Sherrington R, DeLisi L E (1998) A genome-wide search for schizophrenia susceptibility genes. Am J Med Genet 81:364-376.

Stefansson H, Sigurdsson E, Steinthorsdottir V, Bjornsdottir S, Sigmundsson T, Ghosh S, Brynjolfsson J, et al. (2002) Neuregulin 1 and susceptibility to schizophrenia. Am J Hum Genet 71:877-892.

Straub R E, Jiang Y, MacLean C J, Ma Y, Webb B T, Myakishev M V, Harris-Kerr C, Wormley B, Sadek H, Kadambi B, Cesare A J, Gibberman A, Wang X, O'Neill F A, Walsh D, Kendler K S (2002) Genetic variation in the 6p22.3 gene DTNBP1, the human ortholog of the mouse dysbindin gene, is associated with schizophrenia. Am J Hum Genet 71:337-348.

Tochio H, Hung F, Li M, Bredt D S, Zhang M (2000) Solution structure and backbone dynamics of the second PDZ domain of postsynaptic density-95. J Mol Biol 295:225-237.

Torrey E F, Webster M J, Knable M B, Johnston N, Yolken R H (2000) The Stanley Foundation Brain Collection and Neuropathology Consortium. Schizophrenia Research 44:151-155.

Vetter P, Roth A, Hausser M (2001) Propagation of action potentials in dendrites depends on dendritic morphology. J Neurophysiol 85:926-937.

Xu B, Wratten N, Charych E I, Buyske S, Firestein B L, Brzustowicz L M (2005) Increased expression in dorsolateral prefrontal cortex of CAPON in schizophrenia and bipolar disorder. PLOS Med 2(10): e263.

Zoghbi H Y (2003) Postnatal neurodevelopmental disorders: meeting at the synapse?, Science 302:826-830.

What is claimed is:

1. A method for identifying a compound which inhibits complex formation between nitric oxide synthetase 1 adaptor protein (NOS1AP) and NOS1AP binding protein(s), comprising:
   a) incubating said NOS1AP or functional fragment thereof and said NOS1AP binding protein in the presence and absence of said compound under conditions suitable for protein complex formation to occur, wherein said NOS1AP or functional fragment thereof is SEQ ID NO: 2, a fragment consisting of amino acids 181-307 of SEQ ID NO: 2, or a fragment consisting of amino acids 186-312 of SEQ ID NO: 2, and
   b) determining whether the complex formation is decreased in the presence of said compound when compared to complex formation in the absence of said compound,
   wherein said nitric oxide synthetase 1 adaptor protein (NOS1AP) binding protein is selected from the group consisting of carboxypeptidase E (CPE), eEF2, and hippocalcin-like-1, and
   wherein a decrease in NOS1AP-NOS1AP binding protein complex formation in the presence of said compound indicates that the compound is an inhibitor of NOS1AP-NOS1AP binding protein complex formation.

2. The method of claim 1 wherein said compound is a siRNA which down-modulates nitric oxide synthetase 1 adaptor protein (NOS1AP).

3. The method of claim 2, wherein said siRNA comprises SEQ ID NO: 22.

4. The method of claim 1, performed in a neuronal cell.

5. The method of claim 4, wherein said compound increases dendritic branching in said neuronal cell.

* * * * *

```
SEQUENCE LISTING

<160> NUMBER OF SEQ ID NOS: 25

<210> SEQ ID NO 1
<211> LENGTH: 2870
<212> TYPE: DNA
<213> ORGANISM: Homo Sapiens

<400> SEQUENCE: 1
ttcttcttcg tcccgggcgg tgcgttccac tgctctgggg ccggcgccgc gcccagtccc      60
gcttcgggcc gcaagcccca ccgctcccct ccccgggcag gggcgccgcg cagcccgctc     120
ccgccgccac ctcctcccct gccgccctcc tagccggcag gaattgcgcg accacagcgc     180
cgctcgcgtc gcccgcatca gctcagcccg ctgccgctcg gccctcggca ccgctccggg     240
tccggccgcc gcgcggccag ggctcccccct gcccagcgct cccaggcccc gccacgcgtc     300
gccgcgccca gctccagtct cccctccccg gggtctcgcc agcccctttcc tgcagccgcc     360 gcctccgaag gagcgggtcc gccgcgggta accatgccta gcaaaaccaa gtacaacctt     420
gtggacgatg ggcacgacct gcggatcccc ttgcacaacg aggacgcctt ccagcacggc     480
atctgctttg aggccaagta cgtaggaagc ctggacgtgc caaggcccaa cagcagggtg     540
```

| | |
|---|---|
| gagatcgtgg ctgccatgcg ccggatacgg tatgagttta aagccaagaa catcaagaag | 600 |
| aagaaagtga gcattatggt ttcagtggat ggagtgaaag tgattctgaa gaagaagaaa | 660 |
| aagaaaaagg aatggacgtg ggatgagagc aagatgctgg tgatgcagga ccccatctac | 720 |
| aggatcttct atgtctctca tgattcccaa gacttgaaga tcttcagcta tatcgctcga | 780 |
| gatggtgcca gcaatatctt caggtgtaac gtctttaaat ccaagaagaa gagccaagct | 840 |
| atgagaatcg ttcggacggt ggggcaggcc tttgaggtct gccacaagct gagcctgcag | 900 |
| cacacgcagc agaatgcaga tggccaggaa gatggagaga gtgagaggaa cagcaacagc | 960 |
| tcaggagacc caggccgcca gctcactgga gccgagaggg cctccacggc cactgcagag | 1020 |
| gagactgaca tcgatgcggt ggaggtccca cttccaggga atgatgtcct ggaattcagc | 1080 |
| cgaggtgtga ctgatctaga tgctgtaggg aaggaaggag gctctcacac aggctccaag | 1140 |
| gtttcgcacc cccaggagcc catgctgaca gcctcaccca ggatgctgct cccttcttct | 1200 |
| tcctcgaagc ctccaggcct gggcacagag acaccgctgt ccactcacca ccagatgcag | 1260 |
| ctcctccagc agctcctcca gcagcagcag cagcagacac aagtggctgt ggcccaggta | 1320 |
| cacttgctga aggaccagtt ggctgctgag gctgcggcgc ggctggaggc ccaggctcgc | 1380 |
| gtgcatcagc ttttgctgca gaacaaggac atgctccagc acatctccct gctggtcaag | 1440 |
| caggtgcaag agctggaact gaagctgtca ggacagaacg ccatgggctc ccaggacagc | 1500 |
| ttgctggaga tcaccttccg ctccggagcc ctgccgtgc tctgtgaccc cacgacccct | 1560 |
| aagccagagg acctgcattc gccgccgctg ggcgcgggct tggctgactt tgcccaccct | 1620 |
| gcgggcagcc ccttaggtag gcgcgactgc ttggtgaagc tggagtgctt tcgctttctt | 1680 |
| ccgcccgagg acaccccgcc cccagcgcag ggcgaggcgc tcctgggcgg tctggagctc | 1740 |
| atcaagttcc gagagtcagg catcgcctcg gagtacgagt ccaacacgga cgagagcgag | 1800 |
| gagcgcgact cgtggtccca ggaggagctg ccgcgcctgc tgaatgtcct gcagaggcag | 1860 |
| gaactgggcg acggcctgga tgatgagatc gccgtgtagg tgccgagggc gaggagatgg | 1920 |
| aggcggcggc gtggctggag gggccgtgtc tggctgctgc ccgggtaggg gatgcccagt | 1980 |
| gaatgtgcac tgccgaggag aatgccagcc agggcccggg agagtgtgag gtttcaggaa | 2040 |
| agtattgaga ttctgctttg gagggtaaag tggggaagaa atcggattcc cagaggtgaa | 2100 |
| tcagctcctc tcctacttgt gactagaggg tggtggaggt aaggccttcc agagcccatg | 2160 |
| gcttcaggag agggtctctc tccaggactg ccaggctgct ggaggacctg cccctacctg | 2220 |
| ctgcatcgtc aggctcccac gctttgtccg tgatgccccc ctaccccctc actctccccg | 2280 |
| tctccatggt cccgaccagg aagggaagcc atcggtacct tctcaggtac tttgtttctg | 2340 |
| gatatcacga tgctgcgagt tgcctaaccc tcccccctacc tttatgagag gaattccttc | 2400 |
| tccaggccct tgctgagatt gtagagattg agtgctctgg accgcaaaag ccaggctagt | 2460 |
| ccttgtaggg tgagcatgga attggaatgt gtcacagtgg ataagctttt agaggaactg | 2520 |
| aatccaaaca ttttctccag ccggacattg aatgttgcta caaagggagc cttgaagctt | 2580 |
| taacatggtt caggcccttg gtgtgagagc ccaggggag acagcttgt ctgctgctcc | 2640 |
| aaatcactta gatctgattc ctgttttgaa agtcctgccc tgccttcctc ctgcctgtag | 2700 |
| cccagcccat ctaaatggaa gctgggaatt gccctcacc tccctgtgt cctgtccagc | 2760 |
| tgaagctttt gcagcacttt acctctctga aagccccaga ggaccagagc cccagccttt | 2820 |
| acctctcaac ctgtccctc cactgggcag tggtggtcag ttttactgc | 2870 |

<210> SEQ ID NO 2

<211> LENGTH: 501
<212> TYPE: PRT
<213> ORGANISM: Homo Sapiens

<400> SEQUENCE: 2

```
Met Pro Ser Lys Thr Lys Tyr Asn Leu Val Asp Asp Gly His Asp Leu
  1               5                  10                  15

Arg Ile Pro Leu His Asn Glu Asp Ala Phe Gln His Gly Ile Cys Phe
             20                  25                  30

Glu Ala Lys Tyr Val Gly Ser Leu Asp Val Pro Arg Pro Asn Ser Arg
         35                  40                  45

Val Glu Ile Val Ala Ala Met Arg Arg Ile Arg Tyr Glu Phe Lys Ala
     50                  55                  60

Lys Asn Ile Lys Lys Lys Val Ser Ile Met Val Ser Val Asp Gly
 65                  70                  75                  80

Val Lys Val Ile Leu Lys Lys Lys Lys Lys Glu Trp Thr Trp
                 85                  90                  95

Asp Glu Ser Lys Met Leu Val Met Gln Asp Pro Ile Tyr Arg Ile Phe
            100                 105                 110

Tyr Val Ser His Asp Ser Gln Asp Leu Lys Ile Phe Ser Tyr Ile Ala
            115                 120                 125

Arg Asp Gly Ala Ser Asn Ile Phe Arg Cys Asn Val Phe Lys Ser Lys
    130                 135                 140

Lys Lys Ser Gln Ala Met Arg Ile Val Arg Thr Val Gly Gln Ala Phe
145                 150                 155                 160

Glu Val Cys His Lys Leu Ser Leu Gln His Thr Gln Gln Asn Ala Asp
                165                 170                 175

Gly Gln Glu Asp Gly Glu Ser Glu Arg Asn Ser Asn Ser Ser Gly Asp
            180                 185                 190

Pro Gly Arg Gln Leu Thr Gly Ala Glu Arg Ala Ser Thr Ala Thr Ala
        195                 200                 205

Glu Glu Thr Asp Ile Asp Ala Val Glu Val Pro Leu Pro Gly Asn Asp
    210                 215                 220

Val Leu Glu Phe Ser Arg Gly Val Thr Asp Leu Asp Ala Val Gly Lys
225                 230                 235                 240

Glu Gly Gly Ser His Thr Gly Ser Lys Val Ser His Pro Gln Glu Pro
                245                 250                 255

Met Leu Thr Ala Ser Pro Arg Met Leu Leu Pro Ser Ser Ser Lys
            260                 265                 270

Pro Pro Gly Leu Gly Thr Glu Thr Pro Leu Ser Thr His His Gln Met
        275                 280                 285

Gln Leu Leu Gln Gln Leu Leu Gln Gln Gln Gln Gln Thr Gln Val
    290                 295                 300

Ala Val Ala Gln Val His Leu Leu Lys Asp Gln Leu Ala Ala Glu Ala
305                 310                 315                 320

Ala Ala Arg Leu Glu Ala Gln Ala Arg Val His Gln Leu Leu Leu Gln
                325                 330                 335

Asn Lys Asp Met Leu Gln His Ile Ser Leu Leu Val Lys Gln Val Gln
            340                 345                 350

Glu Leu Glu Leu Lys Leu Ser Gly Gln Asn Ala Met Gly Ser Gln Asp
        355                 360                 365

Ser Leu Leu Glu Ile Thr Phe Arg Ser Gly Ala Leu Pro Val Leu Cys
    370                 375                 380

Asp Pro Thr Thr Pro Lys Pro Glu Asp Leu His Ser Pro Pro Leu Gly
385                 390                 395                 400
```

```
Ala Gly Leu Ala Asp Phe Ala His Pro Ala Gly Ser Pro Leu Gly Arg
            405                 410                 415

Arg Asp Cys Leu Val Lys Leu Glu Cys Phe Arg Phe Leu Pro Pro Glu
        420                 425                 430

Asp Thr Pro Pro Pro Ala Gln Gly Glu Ala Leu Leu Gly Gly Leu Glu
                435                 440                 445

Leu Ile Lys Phe Arg Glu Ser Gly Ile Ala Ser Glu Tyr Glu Ser Asn
    450                 455                 460

Thr Asp Glu Ser Glu Gly Arg Asp Ser Trp Ser Gln Glu Glu Leu Pro
465                 470                 475                 480

Arg Leu Leu Asn Val Leu Gln Arg Gln Glu Leu Gly Asp Gly Leu Asp
                485                 490                 495

Asp Glu Ile Ala Val
            500

<210> SEQ ID NO 3
<211> LENGTH: 5559
<212> TYPE: DNA
<213> ORGANISM: Homo Sapiens

<400> SEQUENCE: 3
ctatgaccaa atgtatgggg cttttttccca cacaccaagc aagcaagcag ttctgcagag    60
ggcacacagt gtcctctaac tcagtttgat tctgatacta tctacctgga aacagcatca   120
gatcccacag tttgagggct caatcccaca agactttccc ccatttcaga caccaatcac   180
aagtaatagt ttgtcaccta cacctctgac caagtggcta taaattggtg ttcccactac   240
cctctccttg gactcaactg atttgctaga gcaactgaca gaactcagga aaacacctac   300
atttactggt ttattttaaa ggatattata agggatacca atgaacacca gatggaagag   360
atgcataggg cagggtctgt gggaagggtg gcagagctcc catgccctcc caacgtgcac   420
caccctccag gaacctctaa atgttcagct gcccggcagc tccccacacc cagtcctttt   480
gagtttttaa tggaggcttt attatgtagg catgattgat tacatcattg gccactggtg   540
attagtttaa cttttagccc ctcatctcct ggaggttggg gcgtgggact gaaaaatcct   600
atcctctaat catacctttgg tctgtcctgt gagcagcccc catcccgaag cttccagggg   660 ttcccccaacc actaatcatc taataagcat acaaaaaaca ctcttaccac tctggagatc   720
tcaagggttt ggggagctat atgtcaggaa acagggatga agaccaaaca tgtatttcac   780
tgtatcacac ctgttctcac ccctccccag atcttctctc aattaatatg agacaaaaaa   840
atgagtctga cttcttgacc aaaatatcag ttctgtcctt agcagcttta tggaggacag   900
atttagttta aattccttag gcattatgcc cctgtggctc cactcaatca gaaatagggt   960
caacggcaag gtcagggcct ccaatctggg caagagggag gcagccacgg tatccacaag  1020
tgtaattctc tgagtgctgg ttgctgggag gggcacaccc tgggccagca agtcacttgg  1080
ccaagggtgg ccaactgtga ggtagcactg ccctttactc cctaaaaaaa tgtgaatctc  1140
tttggagcaa actcctcttc agaaatttga gcacttgttt tctgagcaag ggaatcagct  1200
aatgcttttg actccccatc catcttcctg catcctcgtc ccacctctcc tgccccact  1260 cacctggctc tgtctttacc cacaccatgg ttttggtaca agaacaccct ttcccata  1320 agctacattg gtccaggcca taaaaattca ttagttccct ttcttcaggg gccttctgaa  1380
atgctccctg gagaactctt tattcacttc tttgcacaag aatcacatat gtgtgaacac  1440
tggtattggc cttctaactc agtttcttca aaccagggtc ctggtctggt tgcccctgtc  1500
```

-continued

```
tcctcccact gagttttatc tccacataag tattgctcac caagaacaga gctgttgaca   1560
ccactgggcc tcaagcatgc tgaatgcatt gctgccaact gctctgcctt aagaaggttg   1620
gaaactgatg agggtgccac aaattgttca cctcagccct tctgggctgg ttggaggagg   1680
ccctctcatg aatcagtcag caaatgtttg accoctacca ggtggtcctg gtaatatgtg   1740
gtatgaatca tggtcctaga tgtctgccat agcaaataaa aaaggaagac agggaaagaa   1800
gctgtcgcct acagagtggc ttgatgacag ctgcctcact aatttaaaaa gccatgtgta   1860
gtgcttccta tttctcacta tgtttgggtg agtgggagag ggagaaagat tatatgggct   1920
tcgttgtgac actgttctta gccagtgggt caatagatga gttttggttt tgttttttag   1980
aagacaggat gagaagagag tgccccttc cacctccaac atggcatgcc atgctaggtg   2040
ctgaaggagt tctctaagca gggatggagc accgtgcgtg tgtgtgtgta tatgtgcacg   2100
tgtgtgtgta cgtgtgtgtg tgtggcaggt ctagagggtc gatggctctt tcctgcctct   2160
tgcccttggt atgggtacct tagtgatgca tcatggccct cccttaggac acacagcttc   2220
gcagtgccag tgaacccact ccttttggct cctcctctgg aatgataagc ccagatgccc   2280
atgctgcccg tgaagggctt cttcttgaac tgaatgtgga gggcatctct ggtcccggcc   2340
atctgccagt gactctcatg tgcattcatg tccctctctt ctctctgtcc tgtcttctct   2400
gccgctgcct cttctctgca ggtacacttg ctgaaggacc agttggctgc tgaggctgcg   2460
gcgcggctgg aggcccaggc tcgcgtgcat cagcttttgc tgcagaacaa ggacatgctc   2520
cagcacatct ccctgctggt caagcaggtg caagagctgg aactgaagct gtcaggacag   2580
aacgccatgg ctcccagga cagcttgctg gagatcacct tccgctccgg agccctgccc   2640
gtgctctgtg accccacgac ccctaagcca gaggacctgc attcgccgcc gctgggcgcg   2700
ggcttggctg actttgccca ccctgcgggc agccccttag gtaggcgcga ctgcttggtg   2760
aagctggagt gctttcgctt tcttccgccc gaggacaccc cgcccccagc gcagggcgag   2820
gcgctcctgg gcggtctgga gctcatcaag ttccgagagt caggcatcgc ctcggagtac   2880
gagtccaaca cggacgagag cgaggagcgc gactcgtggt cccaggagga gctgccgcgc   2940
ctgctgaatg tcctgcagag gcaggaactg gcgacggcc tggatgatga gatcgccgtg   3000
taggtgccga gggcgaggag atggaggcgg cggcgtggct ggaggggccg tgtctggctg   3060
ctgcccgggt aggggatgcc cagtgaatgt gcactgccga ggagaatgcc agccagggcc   3120
cgggagagtg tgaggtttca ggaaagtatt gagattctgc tttggagggt aaagtgggga   3180
agaaatcgga ttcccagagg tgaatcagct cctctcctac ttgtgactag agggtggtgg   3240
aggtaaggcc ttccagagcc catggcttca ggagagggtc tctctccagg actgccaggc   3300
tgctggagga cctgccccta cctgctgcat cgtcaggctc ccacgctttg tccgtgatgc   3360
cccctaccc cctcactctc cccgtctcca tggtcccgac caggaaggga agccatcggt   3420
accttctcag gtactttgtt tctggatatc acgatgctgc gagttgccta accctccccc   3480
taccttatg agaggaattc cttctccagg cccttgctga gattgtagag attgagtgct   3540
ctggaccgca aaagccaggc tagtccttgt agggtgagca tggaattgga atgtgtcaca   3600
gtggataagc ttttagagga actgaatcca aacattttct ccagccggac attgaatgtt   3660
gctacaaagg gagccttgaa gctttaacat ggttcaggcc cttggtgtga gagcccaggg   3720
ggaggacagc ttgtctgctg ctccaaatca cttagatctg attcctgttt tgaaagtcct   3780
gccctgcctt cctcctgcct gtagcccagc ccatctaaat ggaagctggg aattgccccc   3840
cacctcccct gtgtcctgtc cagctgaagc ttttgcagca ctttacctct ctgaaagccc   3900
```

```
cagaggacca gagcccccag ccttacctct caacctgtcc cctccactgg gcagtggtgg   3960
tcagttttta ctgcaaaaaa aaaaaagaa aaagagaaa gaaaaaaaag aatgaatgca    4020
agctgatagc tgagactgtg agactgtttt tgtccactct tctgaatcac tgccacttgg   4080
gtcagggacc acagccattg ccaccttgg cccatctctc tgcgtgcgtg ccttgagcac    4140
acatataaaa agtgccatgt gcaattgtct tatcttttat gatctaggct ttgcctaggg   4200
atcactactc cttaacgggc tggctggggc gatgaggaaa agctcctttg ctcctgtaag   4260
gccataagtg gctgttaaca gattttcaaa tgcctgaaga gattgctgag acctgctaga   4320
gtcatatgtt cggggaatta agtctttatc ctagacaaca aggtacagat gcaaactgca   4380
gtgttattgg agggtcaatc ggcaaggata tgattatccc aaaatggagt tcatcgaccc   4440
tagctttcct ttagattata tataaataaa agtgcagtcc tcttctaatg ccacagttg    4500 gttttcttgt agcccagaaa gtccaaatta aggaaataa attcagtttt atgttagcct    4560
tccttggtgc atcagggtgt cagtggaaat aggatcaggt ggtgtgtgtg tgtgtgtttt   4620
gtgtgtgtgt gtacacatgt gtttatatat acatgtgtga gggaaagtgt gtacatatat   4680
gtaggattgt aaccagacgg aaaagaatga ggatctccag ggtgtttgaa tcagcaacag   4740
atttgtgttt tctaacatgc atttagttgg agaggcatgg ttctgtttgt tttgttttga   4800
tctaatttgc cattggaaat aggtacagtt acacagagaa ggaagaacca ggaaagtgag   4860
atccatgaaa ctaaatgagc agctgtcaga atccagtgtg gctgagccta cctagcttat   4920
gaaatctaac ccagggttcc ctgagtccaa gaccacttag attattaaga ttttgaacgt   4980
ccagaggagt gaaaagtctg ttttctgacg taagccggag ctgaggataa agccagaggc   5040
cagtggatta ggtgtatgga atgtggatgg agagggcttg tgtgggatgt ggccagggag   5100
tgggtgagga aggccgcttc taaatggcct gtaaaaactt gagattggat agacgaaagg   5160
aaatggagaa attaaagaat tggagaaact agttatctgt gttgctgact ttgggaccca   5220
tccaagactc ctgcctttgg ggtgttccat ggtggtttct tcctgcctgg gcgccaccct   5280
ttccccagtt caggccctcc ctggaggact agttttgtgta ttggcatcct ccccagtgga   5340
cccaaaccag cgcatacttg gtgtgtggag atgggagaca aaggacagat ctaggagcct   5400
tgaaggatca ccagccaccg accctccatc agggccaact gggcaggaaa gggaacattg   5460
cagacctgat ttcccgacga tgtcaccctg tcctccctcc ttgcttcttg ctctgctaac   5520
tcaactctgc cttcctcttt ttcattcttc tactctgcc                         5559
```

<210> SEQ ID NO 4
<211> LENGTH: 211
<212> TYPE: PRT
<213> ORGANISM: Homo Sapiens

<400> SEQUENCE: 4

```
Met Ser Leu Ser Ser Leu Cys Pro Val Phe Ser Ala Ala Ala Ser Ser
 1               5                  10                  15

Leu Gln Val His Leu Leu Lys Asp Gln Leu Ala Ala Glu Ala Ala Ala
            20                  25                  30

Arg Leu Glu Ala Gln Ala Arg Val His Gln Leu Leu Gln Asn Lys
        35                  40                  45

Asp Met Leu Gln His Ile Ser Leu Leu Val Lys Gln Val Gln Glu Leu
    50                  55                  60

Glu Leu Lys Leu Ser Gly Gln Asn Ala Met Gly Ser Gln Asp Ser Leu
65                  70                  75                  80

Leu Glu Ile Thr Phe Arg Ser Gly Ala Leu Pro Val Leu Cys Asp Pro
```

```
                    85                  90                  95
Thr Thr Pro Lys Pro Glu Asp Leu His Ser Pro Pro Leu Gly Ala Gly
            100                 105                 110

Leu Ala Asp Phe Ala His Pro Ala Gly Ser Pro Leu Gly Arg Arg Asp
        115                 120                 125

Cys Leu Val Lys Leu Glu Cys Phe Arg Phe Leu Pro Pro Glu Asp Thr
    130                 135                 140

Pro Pro Pro Ala Gln Gly Glu Ala Leu Leu Gly Gly Leu Glu Leu Ile
145                 150                 155                 160

Lys Phe Arg Glu Ser Gly Ile Ala Ser Glu Tyr Glu Ser Asn Thr Asp
                165                 170                 175

Glu Ser Glu Glu Arg Asp Ser Trp Ser Gln Glu Leu Pro Arg Leu
            180                 185                 190

Leu Asn Val Leu Gln Arg Gln Glu Leu Gly Asp Gly Leu Asp Asp Glu
            195                 200                 205

Ile Ala Val
    210

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
aaatcaacaa ccttgcctaa cg                                          22

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gaaagcactc cagcttcacc                                             20

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gaaggcgtcc tcgttgtgca agg                                         23

<210> SEQ ID NO 8
<211> LENGTH: 24
<212> TYPE: DNA
<213> ORGANISM: Artificial Sequence
<220> FEATURE:
<223> OTHER INFORMATION: primer

<400> SEQUENCE: 8
ttgtgcaagg ggatccgcag gtcg                                        24

<210> SEQ ID NO 9
<211> LENGTH: 24
<212> TYPE: DNA
<213> ORGANISM: Artificial Sequence
<220> FEATURE:
```

<223> OTHER INFORMATION: primer

<400> SEQUENCE: 9
ttagaggttc ctggagggtg gtgc                                              24

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
ttgagtccaa ggagagggta gtgg                                              24

<210> SEQ ID NO 11
<211> LENGTH: 28
<212> TYPE: DNA
<213> ORGANISM: Artificial Sequence
<220> FEATURE:
<223> OTHER INFORMATION: primer

<400> SEQUENCE: 11
aatgaatgca agctgatagc tgagactg                                          28

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
tgaatcactg ccacttgggt cagg                                              24

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
agaaggaaga accaggaaag tgagatcc                                          28

<210> SEQ ID NO 14
<211> LENGTH: 26
<212> TYPE: DNA
<213> ORGANISM: Artificial Sequence
<220> FEATURE:
<223> OTHER INFORMATION: primer

<400> SEQUENCE: 14
atccagtgtg gctgagccta cctagc                                            26

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
atgtggatgg agagggcttg t                                                 21

<210> SEQ ID NO 16

```
<211> LENGTH: 22
<212> TYPE: DNA
<213> ORGANISM: Artificial Sequence
<220> FEATURE:
<223> OTHER INFORMATION: primer

<400> SEQUENCE: 16
gtgaggaagg ccgcttctaa at                                             22

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
cattcatgtc cctctcttct ctc                                            23

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
aatgcaggtc ctctggctta g                                              21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
catcctcacc ctgaagtacc c                                              21

<210> SEQ ID NO 20
<211> LENGTH: 23
<212> TYPE: DNA
<213> ORGANISM: Artificial Sequence
<220> FEATURE:
<223> OTHER INFORMATION: primer

<400> SEQUENCE: 20
gagaagatga cccagatcat gtt                                            23

<210> SEQ ID NO 21
<211> LENGTH: 5
<212> TYPE: PRT
<213> ORGANISM: Homo Sapiens

<400> SEQUENCE: 21

Glu Leu Leu Leu Leu
1               5

<210> SEQ ID NO 22
<211> LENGTH: 19
<212> TYPE: DNA
<213> ORGANISM: Artificial Sequence
<220> FEATURE:
<223> OTHER INFORMATION: primer

<400> SEQUENCE: 22
gcaatatctt cagatgcaa                                                 19
```

<210> SEQ ID NO 23
<211> LENGTH: 19
<212> TYPE: DNA
<213> ORGANISM: Artificial Sequence
<220> FEATURE:
<223> OTHER INFORMATION: primer

<400> SEQUENCE: 23
gtttgtccgt gaccttcaa					19

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gcttggttac tcctggatt					19

<210> SEQ ID NO 25
<211> LENGTH: 1359
<212> TYPE: DNA
<213> ORGANISM: Homo Sapiens

<400> SEQUENCE: 25

```
tggctttgac actggcttga ctggttactt tccgagattt tggagttagc catgtatata      60
acagctgtcc tgcagctcta cctatggtgt tttcacagat actgaatact tggtcacgaa     120
ctcctcctat agctccttta tttgcatatc ttgcaccgtt cagaaactga acacatagga     180
cacaacccct tccattaccc g atatctgcca agatggagat aattaggcaa ctttt ctcca     240 aaactgttga tgtaaaggag aaaagtgact aggccccttc ttarcaatag gcaaattgag     300
ctccagcatt tactaagatg ggaaccataa tacgctggcc ggaaataact cggaagctca     360
ttttgtccat acccagttgt agacagtcaa gaatataaaa atgttctgga ttctcttgtc     420
cttagtactc ctttctgcct tccccatttc tacaaggctg atggcttta aatgttaaaa     480 ccctccctaa aggcacccca taagccctat tacacaagtc acatacgaac aaaaagcgcc     540
taagatagtc ctccatttgg gcgcagtctt gccttctgag aaaggggact ctgagaatta     600
atgagggccc agatctggga tatctgggac aagacttggg ccttcctggt aaaacacgaa     660
aacaaaacaa taaacacggc ccctccccccc tctccaaaaa caaaaacaaa aacttcaagg     720
ccatgccgcc gcggccatca gtagctccgg ctcagaattt gaccgttaaa aaaaggaaac     780
taggctgagc tagggcacct cagatcccgg cagtctgggg ccggggcgaa gttgccggcg     840
tcgcgcggcc gggggcgcgg gcagggccgg gcgcgactct cccggggact ttcacctgct     900
ckgctggcag cgcggggcagc gcgggggcgg accggcggc gggcggggcc ttcttcttcg     960
tcccgggcgg tgcgttccac tgctctgggg ccggcgccgc gcccagtccc gcttcgggcc    1020
gcaagcccca ccgctcccct ccccgggcag gggcgccgcg cagcccgctc ccgccgccac    1080
ctcctcccct gccgccctcc tagccggcag gaattgcgcg accacagcgc cgctcgcgtc    1140
gcccgcatca gctcagcccg ctgccgctcg gccctcggca ccgctccggg tccggccgcc    1200
gcgcggccag ggctcccccct gcccagcgct cccaggcccc gccacgcgtc gccgcgccca    1260
gctccagtct ccctcccccg gggtctcgcc agcccttcc tgcagccgcc gcctccgaag    1320
gagcgggtcc gccgcgggta accatgccta gcaaaacca                           1359
```